US009164103B2

United States Patent
Gougeon et al.

(10) Patent No.: US 9,164,103 B2
(45) Date of Patent: Oct. 20, 2015

(54) MONITORING AND INHIBITING HUMAN IMMUNODEFICIENCY VIRUS INFECTION BY MODULATING HMGB1 DEPENDENT TRIGGERING OF HIV-1 REPLICATION AND PERSISTENCE

(71) Applicant: INSTITUT PASTEUR, Paris (FR)

(72) Inventors: Marie-Lise Gougeon, Clamart (FR); Hela Saidi, Paris (FR); Marie-Therese Melki, Paris (FR); Beatrice Poirier-Beaudoin, Beynes (FR); Valerie Seffer, Brunoy (FR)

(73) Assignee: INSTITUT PASTEUR, Paris (FR)

( * ) Notice: Subject to any disclaimer, the term of this patent is extended or adjusted under 35 U.S.C. 154(b) by 43 days.

(21) Appl. No.: 14/073,112

(22) Filed: Nov. 6, 2013

(65) Prior Publication Data

US 2014/0120525 A1    May 1, 2014

Related U.S. Application Data

(63) Continuation of application No. 13/063,400, filed as application No. PCT/EP2009/061828 on Sep. 11, 2009, now Pat. No. 8,603,766.

(60) Provisional application No. 61/096,135, filed on Sep. 11, 2008.

(51) Int. Cl.
| | |
|---|---|
| *G01N 33/569* | (2006.01) |
| *G01N 33/68* | (2006.01) |
| *A61K 31/00* | (2006.01) |
| *A61K 31/704* | (2006.01) |

(52) U.S. Cl.
CPC ............ *G01N 33/6875* (2013.01); *A61K 31/00* (2013.01); *A61K 31/704* (2013.01); *G01N 33/56988* (2013.01); *C12N 2740/16011* (2013.01); *G01N 2333/16* (2013.01); *G01N 2333/4703* (2013.01); *G01N 2800/52* (2013.01)

(58) Field of Classification Search
None
See application file for complete search history.

(56) References Cited

U.S. PATENT DOCUMENTS

| 8,450,076 | B2 | 5/2013 | Gougeon et al. |
| 2005/0152903 | A1 | 7/2005 | Newman et al. |
| 2010/0158912 | A1 | 6/2010 | Gougeon et al. |
| 2011/0229474 | A1 | 9/2011 | Gougeon et al. |
| 2013/0065221 | A1 | 3/2013 | Gougeon et al. |

OTHER PUBLICATIONS

Bianchi et al., The DNA binding site of HMG1 protein is composed of two similar segments (HMG boxes), both of which have counterparts in other eukaryotic regulatory proteins, The EMBO Journal 11:1055-1063 (1992).
Nowak et al., Elevated plasma levels of high mobility group box protein 1 in patients with HIV-1 infection. AIDS, Apr. 23, 2007, vol. 21, No. 7, pp. 869-871.
Pokriefka et al., Increased Detection of Human Immunodeficiency Virus Antigenemia after Dissociation of Immune Complexes at Low pH. Journal of Clinical Microbiology, 1993, vol. 31, No. 6, p. 1656-1658.
Urbonaviciute et al., Factors masking HMGB1 in human serum and plasma. Jouranl of Leukocyte Biology, Jan. 2007, vol. 81, p. 67-74.
Hazenberg et al., T-cell division in human immunodeficiency virus HIV-1 infection is mainly due to immune activation: a longitudinal analysis in patients before and during highly active antiretroviral therapy. Blood 2000, vol. 95, p. 249-255.
Gaillard et al., A High-Sensitivity Method for Detection and Measurement of HMGB1 Protein Concentration by High-Affinity Binding to DNA Hemicatenanes.
Mateu et al., Non-additive effects of multiple amino acid substitutions on antigen-antibody recognition. European Journal of Immunology 1992, vol. 22, pp. 1385-1389.
Greenspan et al, Defining epitopes: It's not as easy as it seems. Nature Biotechnology, Oct. 1999, vol. 17, pp. 936-937.
Bustin et al., Antigenic Determinants of High Mobility Group Chromosomal Proteins 1 and 2, Biochemistry 21:6773-6777 (1982).
Wisniewski et al., Region of Insect High Mobility Group (HMG) 1 Protein Homologous to Helix 2 of the Rat HMG1-B Box Is in Close Contact with DNA, The Journal of Biochemistry, 369:29261-29264 (1994).
Goodnow et al., Balancing immunity and tolerance: Deleting and tuning lymphocyte repertoires, Proc. Natl. Acad. Sci. USA, vol. 93, pp. 2264-2271, Mar. 1996.
EPO, International Search Report dated Jan. 27, 2010 for International Application No. PCT/EP2009/061828.
Lillo et al., "Improved Detection of Serum HIV p24 Antigen After Acid Dissociation of Immune Complexes," AIDS, vol. 7, No. 10, 1993, pp. 1331-1336.
Mollica et al., "Glycyrrhizin Binds to High-Mobility Group Box 1 Protein and Inhibits Its Cytokine Activities," Chemistry & Biology, vol. 14, Apr. 2007, pp. 431-441.
Saidi et al., "HMGB1-Dependent Triggering of HIV-1 Replication and Persistence in Dendritic Cells as a Consequence of NK-DC Cross-Talk," PLoS ONE, vol. 3, Issue 10, e3601, Oct. 2008, pp. 1-13.
Thierry et al., "High-mobility Group Box 1 Protein Induces HIV-1 Expression from Persistently Infected Cells," AIDS, vol. 21, No. 3, 2007, pp. 283-292.

*Primary Examiner* — Louise W Humphrey
(74) *Attorney, Agent, or Firm* — Law Office of Salvatore Arrigo and Scott Lee, LLP

(57) ABSTRACT

Compositions and methods for modulating human immunodeficiency virus (HIV) infection involving substances that inhibit the ability of high mobility box 1 (HMGB1) protein to interact with natural killer (NK) cells. Therapeutic compositions comprising antibodies and drugs, such as glycyrrhizin, which bind to HMGB1. Methods of detecting or monitoring HIV infection involving detection or quantitation of HMGB1 or antibodies specific for HMGB1 in a biological sample.

19 Claims, 55 Drawing Sheets

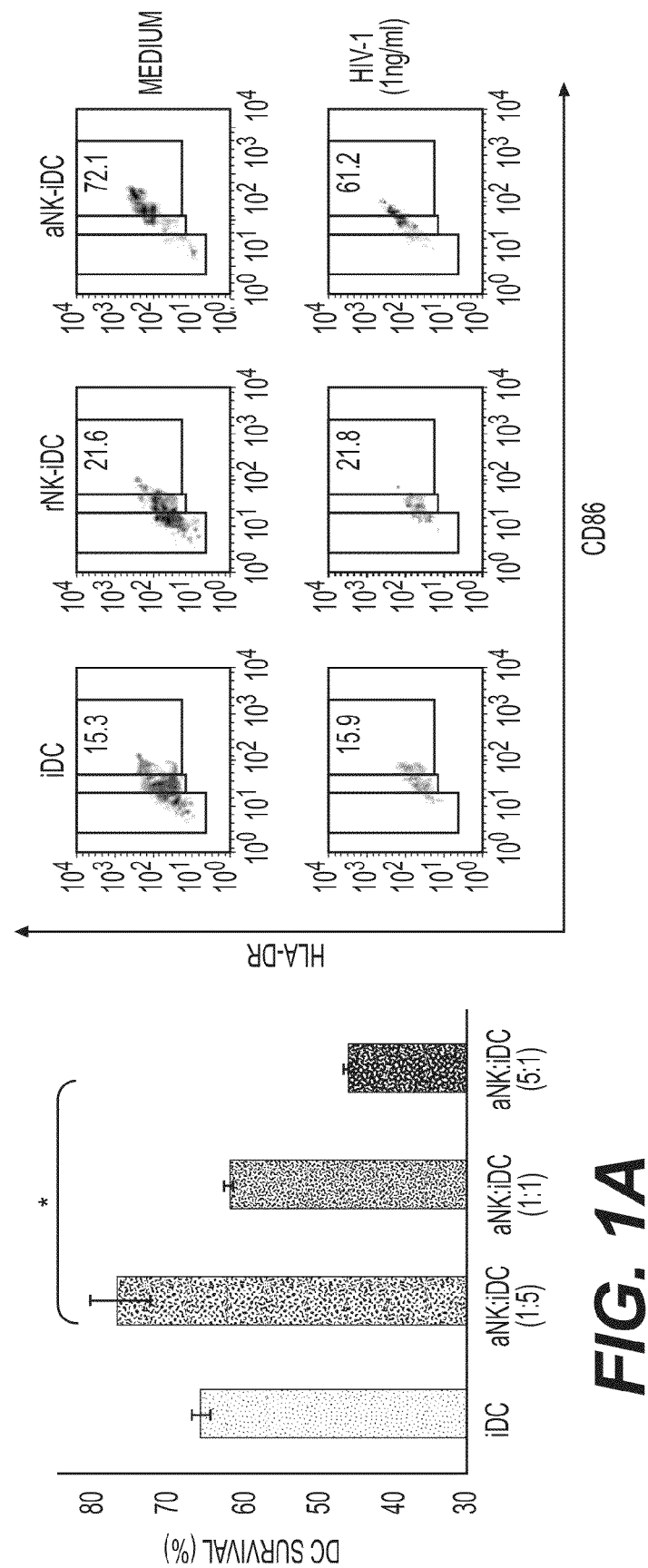

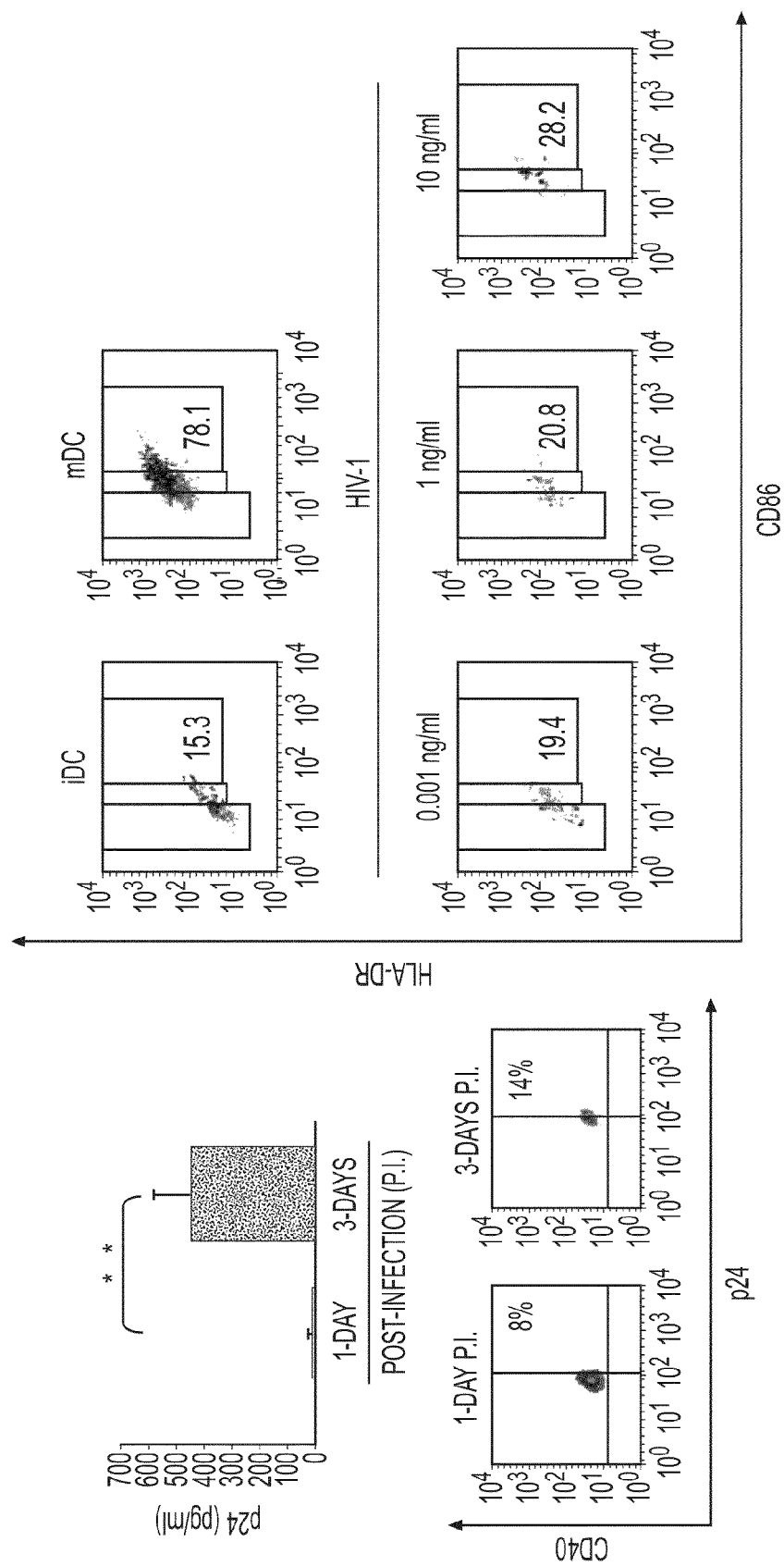

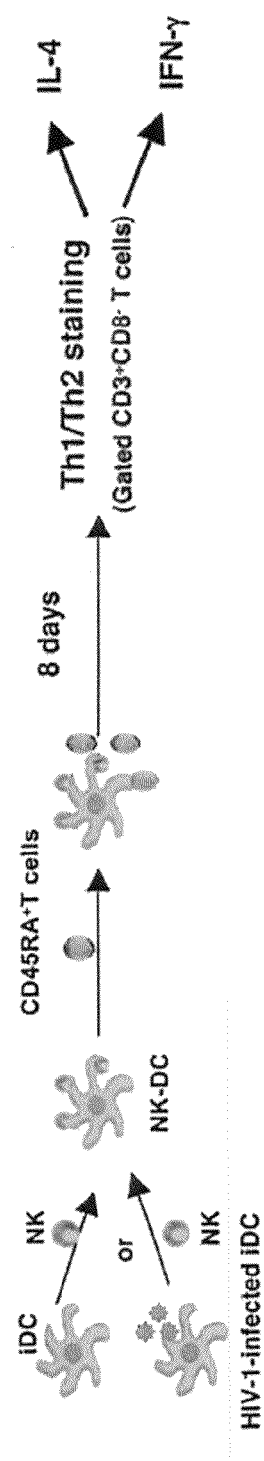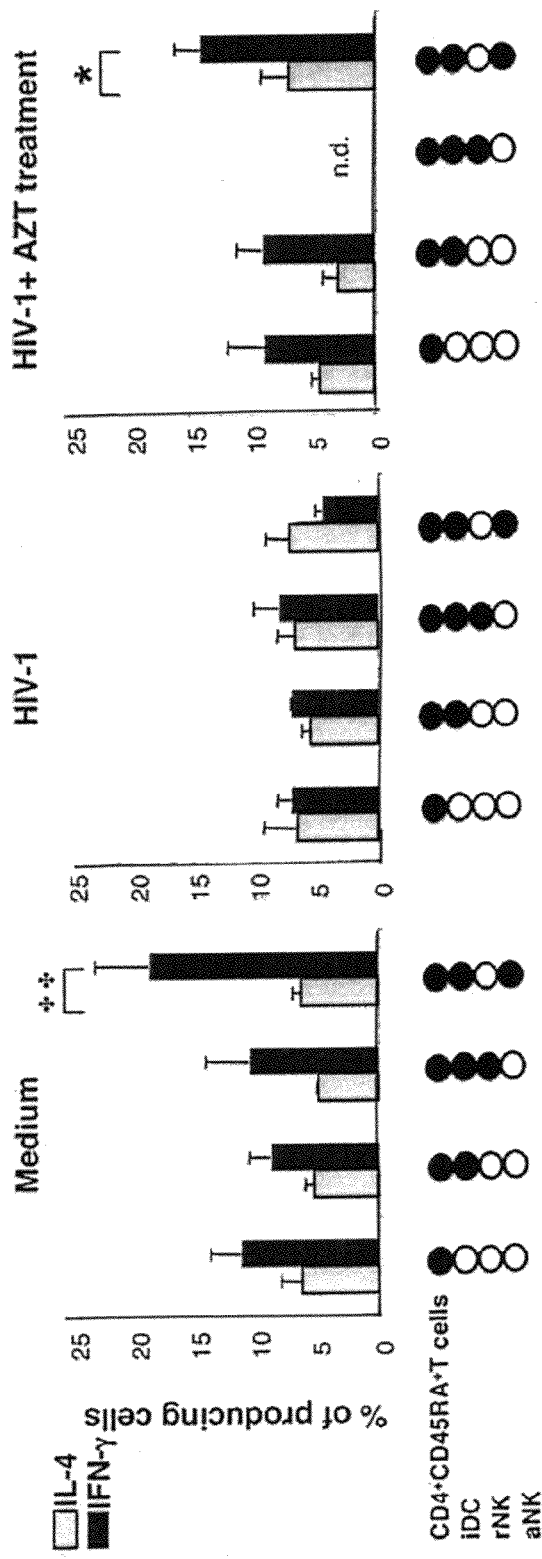
Fig. 4a
Fig. 4b
Fig. 4c
Fig. 4d

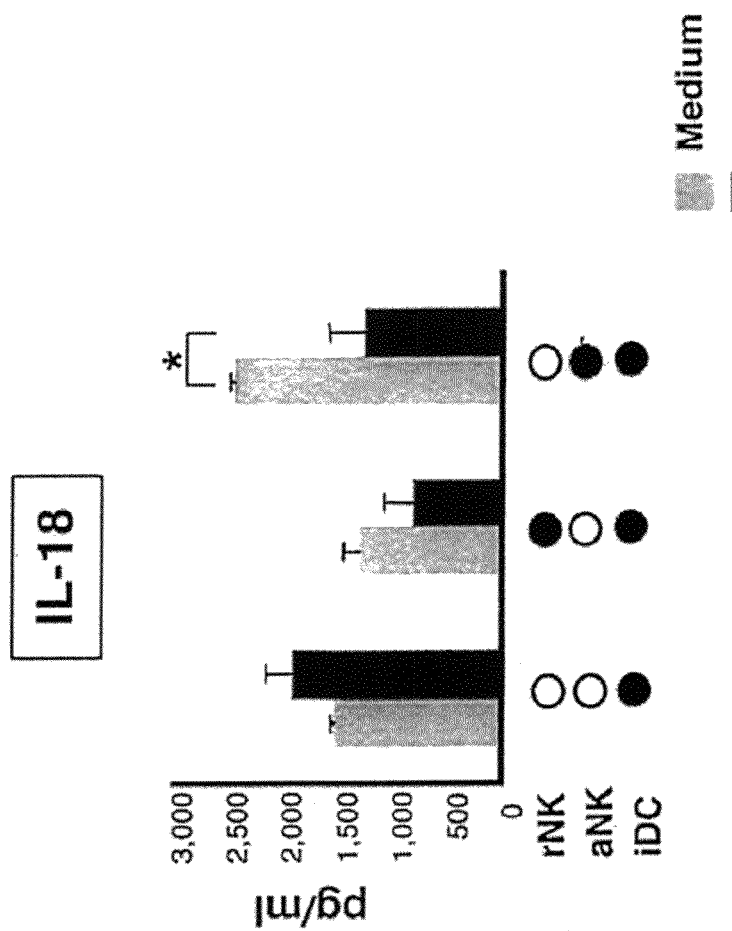
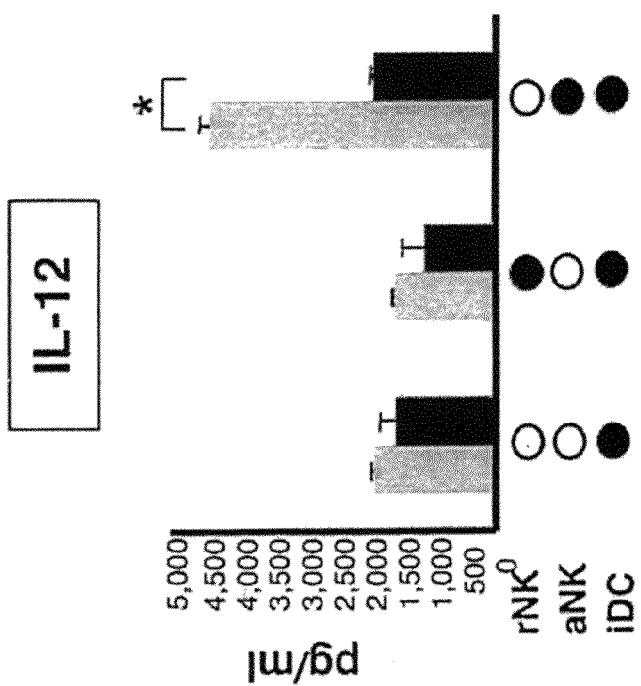

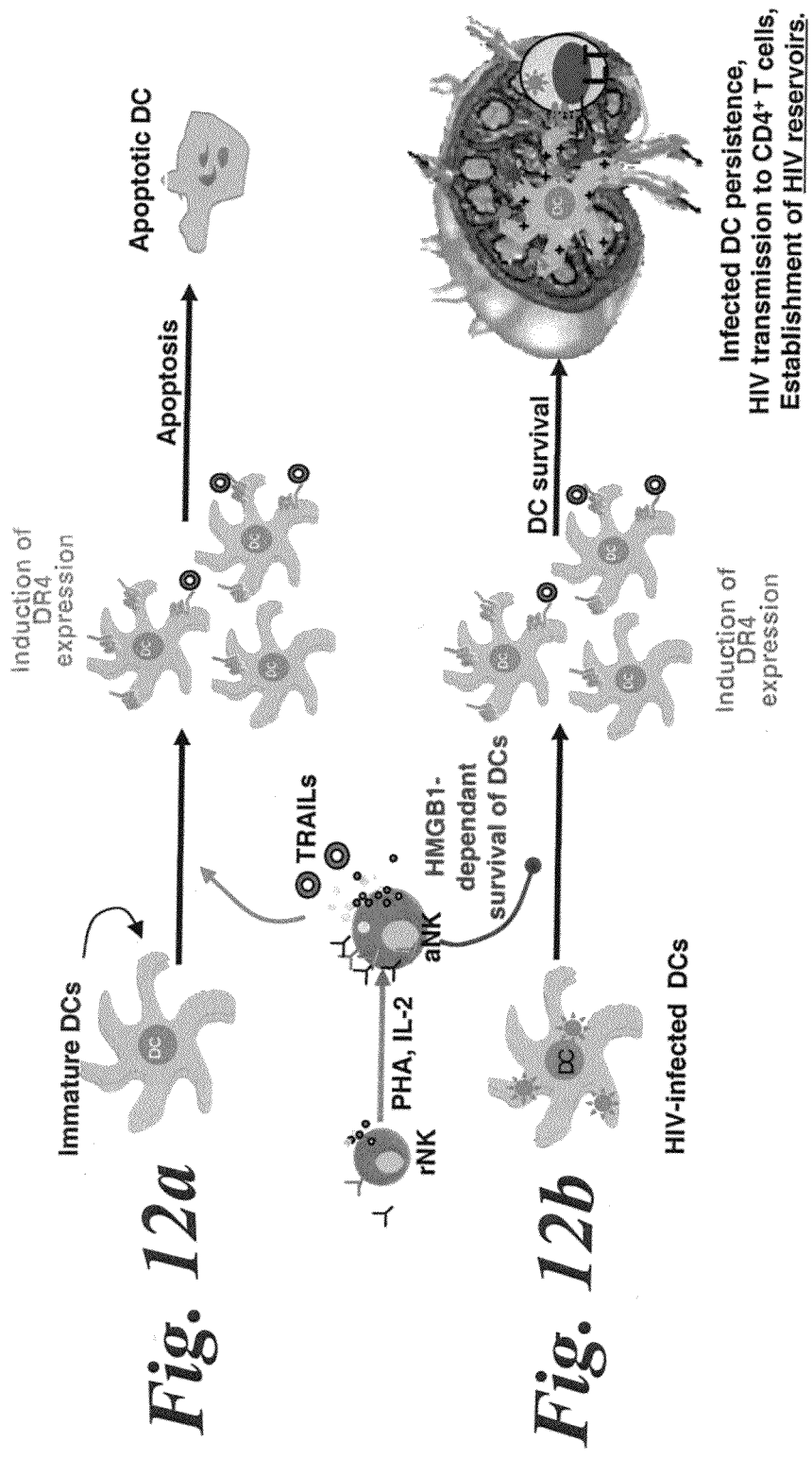

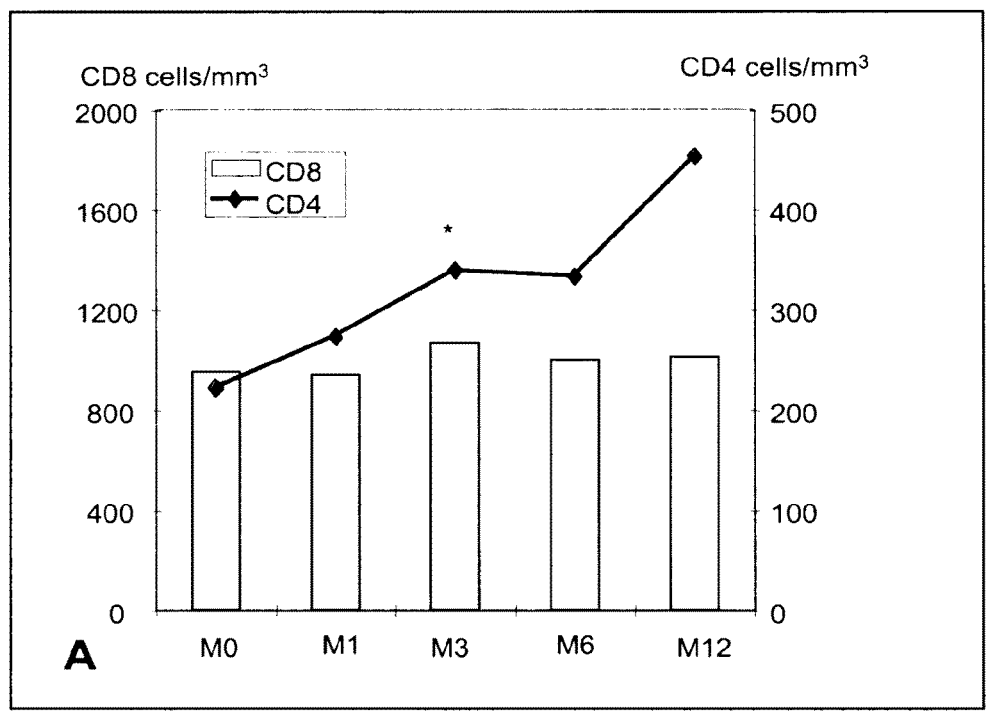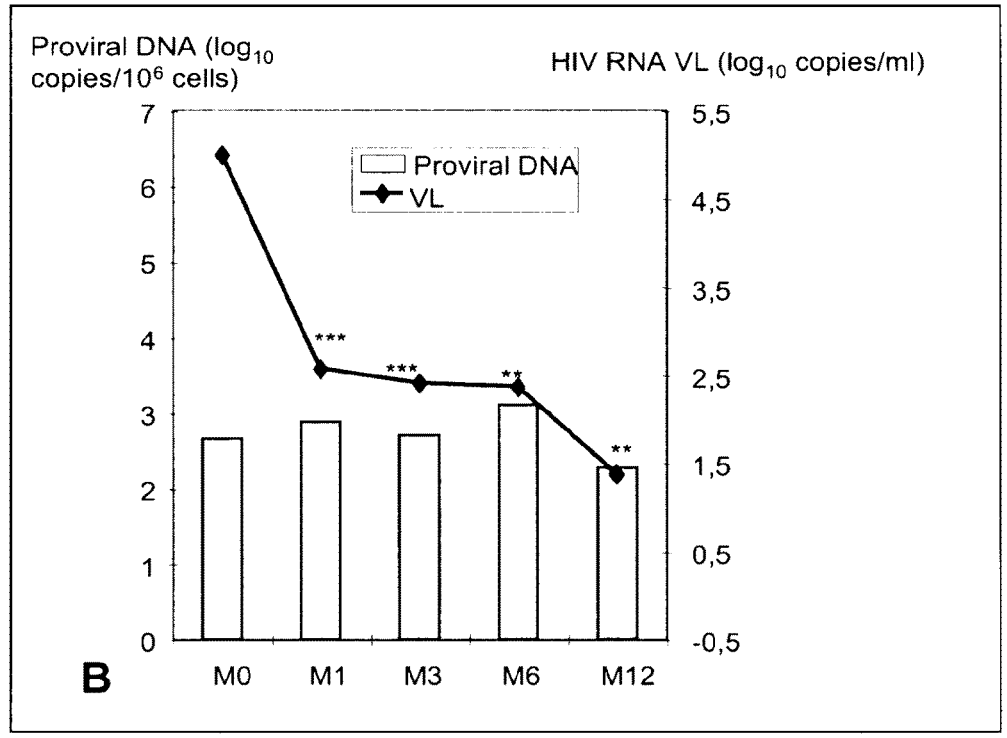
FIG. 17

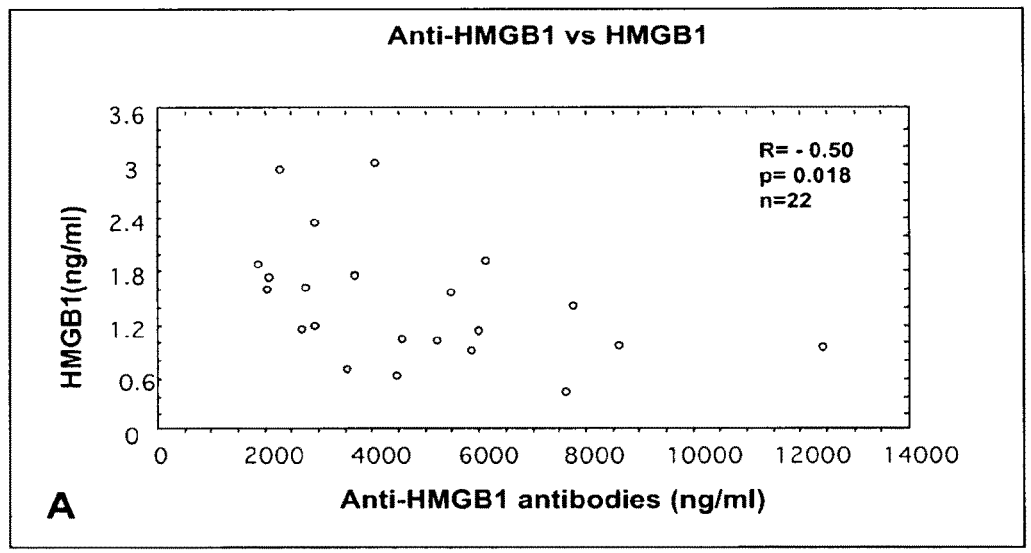
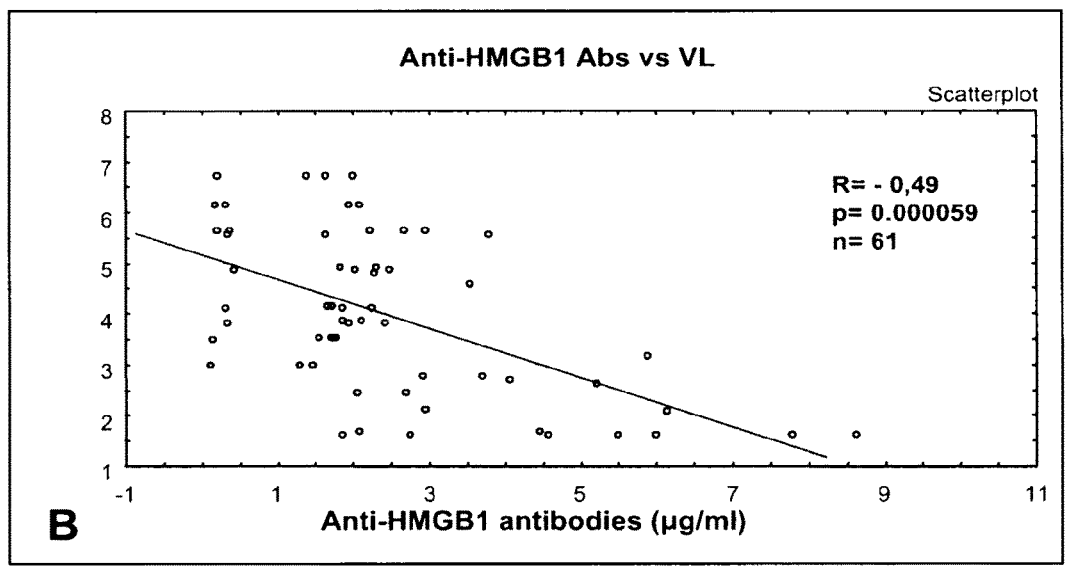
FIG. 20

MONITORING AND INHIBITING HUMAN IMMUNODEFICIENCY VIRUS INFECTION BY MODULATING HMGB1 DEPENDENT TRIGGERING OF HIV-1 REPLICATION AND PERSISTENCE

CROSS REFERENCE TO RELATED APPLICATIONS

This application is a continuation of U.S. application Ser. No. 13/063,400, which is the U.S. National Stage of International Application PCT/EP2009/061828, filed Sep. 11, 2009, which claims priority to U.S. Provisional Application 61/096,135, filed Sep. 11, 2008, all of which are incorporated by reference.

BACKGROUND OF THE INVENTION

1. Field of the Invention

Diagnostic and prognostic methods involving measuring HMGB1 levels and/or antibodies specifically raised against HMGB1. Antibody- and drug-based methods for treating or reducing the severity of human immunodeficiency infection by modulating the activity of HMGB1.

2. Description of the Related Art

Early stages of HIV-1 infection are associated with local recruitment and activation of important effectors of innate immunity, NK cells and DCs. In the first hours and days of mucosal infection, HIV-1 crosses the epithelial barrier and infects CCR5-expressing DCs, macrophages and T cells in the mucosal tissues to initiate infection[1,2]. DCs express CD4, CCR5, DC-SIGNS and other C-type lectin receptors (CLRs) that facilitate capture and dissemination of HIV-1[4,5]. Immature DCs (iDCs) capture HIV-1 through CLRs[6] and captured virus can be internalized and rapidly transmitted to nearby CD4 T cells, in the form of an infectious synapse[7,8]. DC-T cell conjugates facilitate productive infection in CD4 T cells[9], and dissemination of the infection to the draining lymph nodes and subsequent other lymphoid tissue compartments is ensured by virus-carrying DCs together with infected macrophages and CD4 T cells[10].

Migration of iDC to T cell area of secondary lymphoid tissues after virus uptake is associated to a maturation process that allows the resulting mature DC (mDC) to prime an antigen-specific response[11]. Recently, the fate of DCs has been found to be extremely dependent on autologous NK cells[12]. NK-iDC interaction results in activation of NK cells that, in turn, induces DC maturation or killing, depending on their respective density[13,14,15]. DC undergoing maturation secrete several cytokines, such as IL-12 and IL-18, that act as potent inducers of NK cell activation and cytotoxicity[16,17,18,19,20]. In turn, once activated, NK cells produce IFN-γ and TNF-α, capable of inducing DC maturation. This phenomenon is dependent on the engagement of NKp30 by ligands expressed on iDc[17,21], and the down-regulation on iDC of HLA-E, the ligand for CD94/NKG2A inhibitory receptor[22]. Another mechanism was proposed suggesting that NK cells, activated by IL-18 released by iDC at the synaptic cleft, secrete HMGB1, which induces DC maturation and protects DCs from lysis[20]. HMGB1 is a nuclear protein that is present in almost all eukaryotic cells, and it functions to stabilize nucleosome formation, and acts as a transcription-factor-like protein that regulates the expression of several genes[23,24]. HMGB1 is released from necrotic cells, but it can also be secreted by activated macrophages[25] and activated NK cells[20] in response to inflammatory stimuli, and it is one of the main prototypes of the damage-associated molecular pattern molecules (DAMPs)[26]. It was recently discovered to be a crucial cytokine in the immune system, facilitating the trafficking of inflammatory leukocytes, and being critical for DCs to mature, reach the lymph nodes and sustain the proliferation of antigen-specific T cells, and to promote their polarization towards a T-helper 1 phenotype[27,28].

The mechanisms involved in NK-DC interaction during viral infections are poorly understood. It was recently reported in murine CMV (MCMV) infection that MCMV-infected DCs were capable of activating syngeneic NK cells in vitro and also capable of enhancing NK-cell dependent clearance in vivo[29], demonstrating the crucial role of NK-DC cross-talk in controlling viral replication. In HIV infection, NK-DC interaction was found defective in HIV-1-infected viremic, but not aviremic patients, characterized by abnormalities in the process of reciprocal NK-DC activation and maturation, as well as a defect in NK-cell elimination of iDCs[30]. The role of NK-DC cross-talk on maturation, function, and susceptibility to viral replication of HIV-1-infected iDCs was evaluated. It was discovered that maturation of HIV-1-infected DCs could be triggered by activated NK cells, but it was associated with a strong impairment of mature infected DCs to induce Th1 polarization following their crosstalk with NK cells. In addition, the cross-talk between NK cells and HIV-1-infected iDCs resulted in a dramatic increase in viral replication and proviral DNA expression in DCs. This process was mainly triggered by HMGB1, released both by NK cells and DCs, as a consequence of NK-DC cross-talk.

HIV-1 has evolved ways to exploit DCs, thereby facilitating viral dissemination and allowing evasion of antiviral immunity. The fate of DCs is dependent on NK cells. Below, the inventors detail the impact of NK-DC crosstalk on the fate of HIV-1-infected DCs. Activated NK cells efficiently triggered maturation of infected DCs, but this was associated with a strong impairment of mature DCs to induce Th1 polarization. Moreover, the crosstalk between NK cells and infected DCs resulted in a dramatic increase in viral replication and HIV-DNA in DCs. HMGB1 was crucial in this process, and inhibition of HMGB1 activity by glycyrrhizin or specific antibodies abrogated HIV-1 replication in DCs. The inventors describe how their new insights about how HIV 'hijacks' DCs to promote efficiently viral dissemination can provide new ways to inhibit HIV infection, new ways to diagnose and monitor HIV infection, new ways to monitor HIV infection, the viral load and the efficiency of treatment directed against HIV infection and new ways to carry out the prognosis of the state of progression of AIDS or towards AIDS.

DESCRIPTION OF THE INVENTION

Aspects of the invention include the following therapeutic, prognostic and diagnostic applications.

Blocking HMGB1 in patients can help suppress HIV replication, decrease HIV reservoirs in DCs and slow down disease progression. Thus, one aspect of the invention involves a method for modulating human immunodeficiency virus (HIV) infection comprising contacting a subject infected by HIV with an agent that binds to HMGB1, in particular an antibody that binds to High mobility group box 1 protein (HMGB1) or an HMGB1-binding antibody fragment, glycyrrhizin or the isolated RAGE or a fragment of RAGE able to bind HMGB1. The invention also concerns an agent that binds to HMGB1, in particular an antibody that binds to High mobility group box 1 protein (HMGB1) or an HMGB1-binding antibody fragment, glycyrrhizin or the isolated RAGE or a fragment of RAGE able to bind HMGB1, for use as a drug to treat HIV infection in a subject infected by HIV. A particular agent that may be used in therapy is an antibody specifically blocking HMGB1 or a fragment of such antibody, in particular an antibody fragment which retains said ability to specifically block HMGB1. Examples of fragments are a single-chain antibody, or a Fab, Fv and $Fab_2$ fragment. In a particular embodiment, said antibody is a monoclonal antibody, or said fragment is a part of a monoclonal antibody. In another particular embodiment, said antibody or fragment is preferably human or humanized. By "specifically blocking", it is meant that the antibody or fragment thereof has the ability to bind the HMGB1 protein and prevents or decreases its activity, in particular to prevent its binding on at least one of its receptors, in particular the RAGE receptor. In a particular embodiment, the occurrence of the blocking behavior of the antibodies of the invention or their fragments may be tested either by assaying the binding of HMGB1 on at least one of its receptors, and/or by assaying the activity of HMGB1 on dendritic cell (DC) maturation (whether HIV-infected or not), on HIV replication in DC and/or on HIV DNA expression in DC. An antibody or fragment thereof is considered to specifically block the HMGB1 protein, when the decrease of the binding of HMGB1 on one of its receptors (in particular RAGE) or the decrease of the activity of HMGB1 as defined above is more than 50%, more than 60%, more than 70%, more than 80% or more than 90%.

In the context of the invention, the term "specifically" or "specific" means that the antibodies or their fragments are able to recognize and to bind the HMGB1 protein, preferably to other cellular proteins and in particular do not significantly recognize and bind other cellular proteins involved in the immune system, in particular in the context of the NK-DC cross-talk or do not significantly recognize and bind other cellular proteins. In the present application, unless otherwise stated, description relating to antibodies applies to their fragments as disclosed above.

While not being bound to a particular mechanism of action, this method may operate by reducing viral replication and replenishment of viral reservoirs in dendritic cells. Thus, the invention also relates to an agent that binds to HMGB1 as mentioned above for use as a drug to decrease the HIV-reservoir cells, in a subject infected by HIV. The HIV-reservoir cells may be any cell that is sensitive to the HIV and/or can be infected by the HIV. In a particular embodiment, the HIV reservoir cells harbor the proviral DNA. The HIV reservoir cells originate from biological tissues such as blood, solid tissues or mucosa, and in particular from brain, liver, spleen, tonsils, nodes or gut-associated lymphoid tissue (GALT). In a particular embodiment, these cells are peripheral blood cells, lymphoid lineage cells such as T cells especially T CD4 cells, or are monocyte-derived cells such as macrophages or dendritic cells.

Human immunodeficiency virus includes both HIV-1 and HIV-2 strains as well as other variants of this virus, including HIV strains adapted to simians and other mammals.

The invention also applies to treatment, diagnosis and monitoring of infections caused by other retroviruses, including HIV-2 and simian immunodeficiency virus (SIV). Subjects or patients infected by retroviruses like HIV include humans, monkeys and other simians, and other mammals used models of HIV infection. Specific HIV-1 strains include the R5 HIV-1 strain and the X4 HIV-1 strain.

HMGB1 is a well-known protein appearing in the nucleus and is also known to be a cytokine. Physical and functional characteristics of HMGB1 are disclosed by and incorporated by reference to Lotze, et al., Nature Reviews, Immunology 5:351 (2005).

Antibodies which bind to HMGB1 are known and can be produced by methods well-known in the art. An example of commercially available anti-HMGB1 antibodies are Rabbit primary polyclonal antibodies to human HMGB1 (Abcam ref. 18256) which are directed against a KLH-conjugated synthetic peptide derived from residues 150 to C-terminus of human HMGB1. These methods include those which produce polyclonal antibodies to HMGB1 and monoclonal antibodies to HMGB1 or to specific fragments of HMGB1. Antibodies used in therapeutic applications have the characteristic to be blocking, e.g., especially they interfere with HMGB1-induced HIV replication in infected dendritic cells. These antibodies are preferably derived from the same species as the subject to which they are administered and recognize or are induced to the HMGB1 of the same species to which they will be administered. These antibodies may have different isotypes, such as IgA, IgG or IgM isotypes. Antibody fragments which bind HMGB1 may also be employed, including Fab, $Fab_2$, and single chain antibodies or their fragments.

Humanized anti-HMGB1 monoclonal antibodies may also be employed therapeutically in human. These may be produced by methods well-known in the art. Injection of these antibodies to HIV infected patients with high viral load and elevated levels of HMGB1 can be used to reduce virus replication and limit the number of reservoir cells. Such humanized antibodies, can be used as salvage or alternative therapy, or combined with antiretrovirals.

Antibodies or their fragments as defined herein that bind to HMGB1 may be administered to a subject to bind to HMGB1 and modulate HIV replication or infection in the subject. Modes of administration include, but are not limited to, intravenous (i.v.), intradermal, subcutaneous (s.c.), intracerebral, transmucosal, transdermal, by inhalation (e.g., intratracheal, intrapulmonary, or intrabroncial), intransal, oral, subuccal, transdermal, and rectal administration.

Targeting HMGB1 production or release, or preventing its interaction with its receptor(s), in particular RAGE on DCs, may be employed to treat chronic viral infections, considering its impact on the inflammatory response and maturation and survival of infected DCs. Thus, agents, such as antibodies or antibody fragments, which bind to HMGB1 receptor, (e.g. RAGE) and inhibit its interaction with HMGB1 or soluble HMGB1 receptor proteins (e.g. soluble RAGE proteins or fragment able to bind HMGB1) that inhibit functional interaction of HMGB1 receptor (e.g. RAGE) on DCs and HMGB1 may be employed. Portions of HMGB1 that bind to RAGE on DC's and inhibit the functional interaction of HMGB1 with DCs are also contemplated.

The inventors have shown that glycyrrhizin is able to inhibit HMGB1-dependent HIV replication in DCs. Glycyrrhizin therapy has few side effects and it has been recently used successfully in vivo to prevent hepatocellular carcinogenesis in patients with IFN-resistant active chronic hepatitis C. This therapy may be used in chronically HIV-infected patients with detectable viral load and increased levels of HMGB1, either as salvage therapy because of multi-drug resistance virus, as an alternative therapy (less toxic and acting on the inflammatory microenvironment rather than on the virus itself) to the use of HIV-specific anti-retrovirals, or a combined therapy with anti-retrovirals in case of incomplete success of these drugs.

Therefore, yet a further aspect of the invention is a method for modulating human immunodeficiency virus (HIV) infection, including HIV-1 infection, comprising contacting a cell or a subject infected by HIV with an amount of an agent that binds to High mobility group box 1 protein (HMGB1), in particular which inhibits natural killer (NK) cell dependent triggering of HIV replication in a dendritic cell (DC). The invention also concerns an agent that binds to High mobility group box 1 protein (HMGB1), in particular which inhibits natural killer (NK) cell dependent triggering of HIV replication in a dendritic cell (DC), for use in the modulation of human immunodeficiency virus (HIV) infection (including HIV-1 infection) in a cell or a patient infected by HIV.

Glycyrrhizin is one such agent and modes and concentrations of glycyrrhizin useful for providing binding to HMGB1 are disclosed and incorporated by reference to Mollica, et al., Chem. Biol. 14:431 (2007). Other agents or compounds, besides glycyrrhizin, that bind to HMGB1 may also be employed. Soluble ligands or segments of natural ligands to which HMGB1 binds may be employed. Such ligands may be obtained from leukocytes or antigen-presenting cells to which HMGB1 binds.

Human patients infected with, or at risk of, HIV infection may be treated with the antibodies, antibody fragments, and other HMGB1-binding agents disclosed herein in order to maintain the immune system of the patients including with an antibody specifically blocking HMGB1 or a fragment which retains said ability to specifically block HMGB1. Since glycyrrhizin is nontoxic while many antiretroviral drugs cause substantial toxicity, the treatments of the invention can reduce detrimental side-effects of conventional anti-HIV therapy. Antibody-based products recognizing HMGB1 also lack the toxicity of many anti-HIV drugs and can also be employed to reduce the side-effects of HIV treatment. Similarly, advanced treatment of human patients who are resistant, or have developed multiple resistances to conventional retroviral drug treatments can be treated with the methods of the invention, including antibody products and other agents that bind to HMGB1. Combined therapy with glycyrrhizin (or humanized blocking anti-HMGB1 antibodies) and anti-retroviral drugs at lower doses that when used alone is also contemplated.

These HMGB1 binding agents or compounds may be used alone or in combination with at least one further active compound against HIV infection, or be administered in combination with other agents, such as drugs and pharmaceutical agents, used to treat HIV infection. Examples of such drugs and pharmaceutical agents include two nucleoside analogue reverse transcriptase inhibitors (NARTIs or NRTIs), protease inhibitors, and non-nucleoside reverse transcriptase inhibitors (NNRTIs), including AZT and Indinavir.

The invention also includes sterile compositions, suitable for administration to human subjects comprising an isolated antibody or antibody fragment that binds to High mobility group box I (HMGB1) protein, other HMGB1 binding agents, and/or glycyrrhizin; and a pharmaceutically acceptable carrier, excipient, or diluent. These compositions may contain other drugs or pharmaceutical agent other than said antibody, antibody fragment and/or glycyrrhizin, used to treat human immunodeficiency virus infection, such as those mentioned above. Generally, antibodies used as therapeutic tool for HIV-infected human patients should be human or humanized antibodies which block the activity of HMGB1.

Other aspects of the invention include glycyrrhizin for use as a drug to treat HIV infection in human, use of glycyrrhizin for the manufacture of a medicament for therapeutic application in HIV infections, and use of an isolated humanized blocking HMGB1-specific antibody or antibody fragment for the manufacture of a medicament for the therapeutic application in HIV infections.

The invention also concerns an in vitro method for quantitating total antibodies specific for HMGB1 contained in a biological sample obtained from a subject, comprising (a) treating the sample by an acid treatment to dissociate the immune complexes involving HMGB1 found in the sample, preferably with glycine 1.5M at a low pH; (b) contacting said treated biological sample with native HMGB1 protein or derivatives thereof; and (c) quantitating the total antibodies specific for HMGB1.

In a preferred embodiment, the acid treatment consists to put in contact the sample with an acidic dissociation solution, having a low pH, preferably between pH 1 and 3, chosen to separate the HMGB1 protein from antibodies to which it is immunologically bound in the sample, without altering binding ability of this antibody. In a particular embodiment, the acidic dissociation solution is glycine (e.g. 1.5M) at a low pH, preferably between pH 1 and 3 (e.g. 1.85). The acid treatment is then stopped with a neutralization buffer (such as Tris, for example 1.5M Tris, pH9). In another preferred embodiment, in combination with the previous one or not, the incubation with the acidic dissociation solution is carried out at a temperature between 20 and 37° C., preferably at 25° C., and/or the neutralization step takes place in ice.

In the present application, the term "quantitating" encompasses the term "quantifying" and any suitable informative determination of the HMGB1 protein or specific antibodies.

The invention also relates to an in vitro method for monitoring the HIV infection, in a biological sample obtained from a subject who is known to be infected with HIV, comprising quantitating the antibodies specific for High mobility group box I (HMGB1) contained in a biological sample obtained from this patient, wherein the antibodies targeted for quantitation are either the total antibodies specific for HMGB1 or their circulating fraction (circulating antibodies) or their immunological complexed fraction.

The methods for monitoring the HIV infection, the viral load or the efficacy of a treatment and the prognostic method disclosed herein, may be implemented based on either the quantitation of the circulating (residual) antibodies specific for HMGB1, or on the quantitation of the total antibodies specific for HMGB1 or on the quantitation of the fraction of immunological HMGB1/specific antibodies complex.

In a particular embodiment, all these methods are based on either the quantitation of circulating specific antibodies or total specific antibodies.

The quantitation of the total antibodies specific for HMGB1 may be preferred when the level of circulating antibodies specific for HMGB1 is low.

When the quantitation is based on the total antibodies specific for HMGB1, the methods of the invention also comprise a step suitable for dissociation of immunological complexes formed with HMGB1-specific antibodies, and for example the methods of the invention use or include the quantitation method based on the acidic treatment as disclosed above and illustrated in the examples.

In a particular embodiment, said quantitation of the antibodies specific for HMGB1 is carried out by contacting a biological sample (obtained from a subject) with the High mobility group box I (HMGB1) protein or derivatives thereof. The contact of the sample with said antibody as well as the quantification of the formed complex are carried out in vitro.

The invention also concerns a method for monitoring the HIV viral load in a biological sample obtained from subject, who is known to be infected with HIV, comprising carrying out the method of quantitation of the total antibodies specific for HMGB1 or the method of monitoring based on the antibodies specific for HMGB1 mentioned herewith, wherein the more the antibodies specific for HMGB1, the less the viral load.

By "viral load", it is meant either the HIV RNA (which is derived from viral particles and present in plasma) or the HIV DNA (which is integrated in the cell genome and present in cells). In a particular embodiment, the methods of the invention based on the quantitation of antibodies specific for HMGB1 are suitable to monitor the HIV RNA viral load.

It is understood that for the quantitation method and the methods of monitoring the HIV infection, of the viral load or of the efficacy of a treatment and the prognostic method of the invention, it is possible to use the sequence of the full length HMGB1 protein (mammalian origin, preferably human origin) or any peptide (10 to 30 amino acid residues) or polypeptide (30 to 215 amino acid residues, preferably 30 to 50, or 30 to 100, or 30 to 150 residues) derived from HMGB1 (HMGB1 protein derivatives) as long as these derivatives bind to antibodies specific for HMGB1 and/or enable to quantitate the anti-HGB1 antibodies. Such derivatives are selected in the group consisting of a recombinant HMGB1 (e.g. HMG biotech, HM-115), an immunologically reactive part of HMGB1, an immunologically reactive part of HMGB1 whose sequence is common to HMGB1 proteins of various origins. Such an example is the recombinant BOXB from HMGB1 corresponding to the sequence common to human and mouse of HMGB1 (HMGbiotech HM-051).

These methods are carried out on a biological sample obtained from a subject infected with HIV, such as blood, plasma, serum, saliva, or any body fluid or tissue.

By "monitoring the HIV infection", it means the comparison of the progression of the HIV infection, i.e. the decrease, the increase or the stability, as compared to a previous assay. The progression of the HIV infection reflects the HIV replication and/or the integration of the HIV genome into the genome of target cells.

The invention also relates to an in vitro method for monitoring the efficacy of a treatment directed against HIV infection, in a subject infected with HIV comprising carrying out the method of quantitation of the total antibodies specific for HMGB1 or the method of monitoring based on the antibodies specific for HMGB1 mentioned herewith, on samples obtained from said subject at different times during the treatment, and determining the efficacy of the treatment given to the subject.

In this method of the invention, the quantity of antibodies specific for HMGB1 in a HIV infected patient may be compared with the quantity of antibodies specific for HMGB1 in a non-infected (i.e. non-HIV infected) patient.

Moreover, the quantity of antibodies specific for HMGB1 may be compared with the quantity obtained from the same subject at a different time, such as prior to infection, during primary, acute or chronic infection, or prior to the initiation of the treatment, for example before the treatment and each month during the treatment.

Administration of substance(s) is providing "treatment" according to the invention, either when the quantity of total antibodies specific for HMGB1 is decreased, preferably from a factor of at least 1.5, at M6 (6 months after the initiation of the treatment) or from a factor of at least 2 or at least 3 at M12, as compared to the quantity of total antibodies specific for HMGB1 in the same patient before treatment. The term "treatment" more generally refers to any means used to reduce the HIV infection, i.e. the HIV RNA and/or the HIV DNA. Treatment according to the invention encompasses recourse to conventional treatments using antiretroviral drugs such as Nucleoside/Nucleotide Reverse Transcriptase Inhibitors (NRTIs), Non-Nucleoside Reverse Transcriptase Inhibitors (NNRTIs), Protease Inhibitors (PIs), Fusion or Entry Inhibitors, Integrase Inhibitors or any combination thereof.

The invention is also directed to an in vitro prognostic method of either the state of progression of Acquired immune deficiency syndrome (AIDS) or the state of progression toward AIDS, in a patient infected with HIV, comprising carrying out the quantitation method or the method for monitoring HIV infection disclosed above in a sample obtained from a patient after infection, and preferably during primary or acute infection, or during chronic infection and wherein the more the level of antibodies specific for HMGB1, the more the risk to develop AIDS or an advanced state of AIDS.

The term "prognostic" refers to the possibility to evaluate, at the time the quantitation of the total antibodies specific for HMGB1 is carried out from a sample obtained from a patient, the risk for the patient to develop AIDS or to progress toward AIDS. The expression "state of progression" refers to the various stages met in the progression of AIDS or toward AIDS, and in particular refers to the WHO Disease Staging System for HIV Infection and Disease produced and updated by the World Health Organisation, which is summarized hereinafter. Stage I: HIV disease is asymptomatic and not categorized as AIDS; Stage II includes minor mucocutaneous manifestations and recurrent upper respiratory tract infections; Stage III includes unexplained chronic diarrhea for longer than a month, severe bacterial infections and pulmonary tuberculosis; and Stage IV includes toxoplasmosis of the brain, candidiasis of the oesophagus, trachea, bronchi or lungs and Kaposi's sarcoma.

Any of the in vitro methods disclosed above involving the quantitation of the antibodies specific for HMGB1 may be carried out by implementing ELISA, or other immunological detection methods, using the High mobility group box I (HMGB1) protein or derivatives thereof coated on a solid support, and optionally using secondary antibodies able to detect the HMGB1 specific antibodies.

Based on the results shown below, the inventors have found that HMGB1 triggers in vivo HIV replication in HIV-1-infected patients. Consequently, yet another aspect of the invention involves detection of an increased concentration of HMGB1 in biological samples, such as sera, from HIV-infected subjects. A positive correlation between the viral load and HMGB1 concentration may also be used to monitor HIV infection. Increased HMGB1 levels may be correlated with disease progression or associated with a worse prognosis. HMGB1 concentration in biological samples may be quantified with well-known diagnostic tests, such as ELISA tests. Recombinant hHMGB1, anti-hHMGB1 mAbs and rabbit anti-hHMGB1 serum are commercially available and may used in such diagnostic tests. Such a test is used to quantifying HMGB1 concentration in patients' samples, to identify HMGB1 as a prognostic marker of evolution of HIV infection, and to monitor the in vivo effect of humanized anti-HMGB 1 antibodies.

The invention also relates to an in vitro method for monitoring HIV infection in a subject infected with HIV comprising quantitating High mobility group box I (HMGB1) protein contained in a biological sample obtained from said subject, in particular by contacting the biological sample from said subject infected with HIV, with antibodies that immunologically bind to High mobility group box I (HMGB1), wherein the HMGB1 protein targeted for quantitation is either the total HMGB1 protein or its circulating fraction (circulating HMGB1) or its immunological complexed fraction.

The methods for monitoring the HIV infection, the viral load or the efficacy of a treatment and the prognostic method disclosed herein, may be implemented based on the quantitation of the circulating (residual) HMGB1, based on the quantitation of the total HMGB1 or based on the quantitation of the fraction of immunological HMGB1/specific antibodies complex.

In a particular embodiment, all these methods are based on either the quantitation of circulating HMGB1 or total HMGB1. The quantitation of the total HMGB1 may be preferred when the level of circulating HMGB1 is low. When the quantitation is based on the total HMGB1, the methods of the invention also comprise a step suitable for dissociation of immunological complexes formed with HMGB1-specific antibodies, and for example the methods of the invention use or include an acidic treatment of the sample.

A suitable acidic treatment comprises contacting the sample with an acidic dissociation solution, having a low pH, preferably between pH 1 and 3, chosen to separate the HMGB1 protein from the specific antibody without altering the HMGB1 protein and its recognition capacity by specific antibodies. In a particular embodiment, the acidic dissociation solution is glycine (e.g. 1.5M) at a low pH, preferably between pH 1 and 3 (e.g. 1.85). The acid treatment is then stopped with a neutralization buffer (such as Tris, for example 1.5M Tris, pH9). In another preferred embodiment, in combination with the previous one or not, the incubation with the acidic dissociation solution is carried out at a temperature between 20 and 37° C., preferably at 25° C., and/or the neutralization step takes place in ice.

The quantitation of the HMGB1 protein may be compared to the amount of HMGB1 from a biological sample obtained from a subject not infected with HIV, or to the amount of HMGB1 from a biological sample obtained from the same subject at a different time.

The invention also concerns a method for monitoring the HIV viral load in a biological sample obtained from a subject, which is known to be infected with HIV, comprising carrying out the quantitation of the HMGB1 protein, wherein the more the HMGB1 protein, the more the viral load. By "viral load", it is meant either the HIV RNA (which is derived from viral particles and present in plasma) or the HIV DNA (which is integrated in the cell genome and present in cells). In a particular embodiment, the methods of the invention based on the quantitation of HMGB1 are suitable to monitor the HIV RNA viral load.

The invention also relates to an in vitro method for monitoring the efficacy of a treatment directed against HIV infection in a subject infected with HIV, comprising carrying out the method of monitoring the HIV infection based on the HMGB1 protein disclosed above, on samples obtained from said subject at different times during the treatment, and determining the efficacy of the treatment given to the subject, and optionally comparing these results obtained in a sample of the same subject prior to the initiation of the treatment. Administration of substance(s) is providing "treatment" according to the invention either when the quantity of cellular HMGB1 protein is either decreased, preferably from a factor of at least 1.5 at M1 (1 month after the initiation of the treatment) or from a factor of at least 2 at M3, as compared to the quantity of HMGB1 in the same patient before treatment, or reached the value obtained in samples of healthy donors (less than 500 pg/ml). A treatment may also be considered efficient when the quantity of total HMGB1 protein reached the value obtained in samples of healthy donors. The term "treatment" more generally refers to any means used to reduce the HIV infection, i.e., the HIV RNA and/or the HIV DNA.

The invention also relates to an in vitro prognostic method of either the state of progression of Acquired immune deficiency syndrome (AIDS) or the state of progression toward AIDS, in a patient infected with HIV, comprising quantitating HMGB1 by any method disclosed above, in a sample obtained from a patient after infection, and preferably during primary or acute infection, or during chronic infection and wherein the more the level of total HMGB1, the more the risk to develop AIDS or an advanced state of AIDS. The definitions given above, regarding the prognostic method based on the antibodies specific for the HMGB1 protein, also apply here.

Another aspect of the invention concerns a kit to quantitate the total antibodies specific for the High mobility group box 1 protein (HMGB1) in a sample, comprising: a) native HMGB1 protein or derivatives thereof as defined above, and b) an acidic dissociation solution suitable to dissociate immunological HMGB1/anti-HMGB1 antibody complexes found in the sample when taken from the patient, such as defined above.

The invention also relates to a kit to quantitate the total High mobility group box 1 protein (HMGB1) in a sample, comprising a) an antibody specific for the HMGB1 protein, or a fragment thereof able to bind the HMGB1 protein, as defined above and b) an acidic dissociation solution suitable to dissociate immunological HMGB1/anti-HMGB1 antibody complexes found in the sample when taken from the patient, such as defined above. Optionally, these kits may also contain a neutralization buffer, for example as defined above and/or secondary antibodies binding to and/or revealing the formation of the HMGB1/specific antibodies complex.

Thus, yet another aspect of the invention is the diagnosis, including differential diagnosis, of immunodeficiency virus (HIV) infection or the assessment of the risk of HIV infection in a subject. This diagnostic method involves contacting a biological sample, such as blood, plasma, serum, saliva, or other body fluids, obtained from a subject suspected of being infected with HIV with an antibody that immunologically binds to High mobility group box 1 protein (HMGB1) and detecting complex formation between any HMGB1 in said sample and the antibody or antibody fragment that binds to HMGB1. The contact of the sample with said antibody as well as the detection of the formed complex are carried out in vitro. Diagnosis or an indication of the risk of being infected by HIV may be determined based on increased formation of antibody-HMGB1 complexes compared to complex formation in a control subject not infected with HIV, or compared to complex formation in said subject prior to HIV infection, such as HIV-1 infection. One example of such a diagnostic method is the use of ELISA to detect HMGB1 protein using a monoclonal antibody coated on a solid support and polyclonal antibody to detect HMGB1 bound to coated mAb.

Other diagnostic tests to exclude or control for acute and/or chronic inflammation in said subject or to indicate the presence or titer of HIV in a test subject may also be performed as part of the overall diagnostic process of human or non-human subjects.

Similarly, a subject who is known to be infected with HIV or previously infected by HIV may be monitored by contacting a biological sample from the subject with an antibody or antibody fragment that binds to High mobility group box I (HMGB1) protein and quantifying complex formation between HMGB1 in said sample and said antibody. The contact of the sample with said antibody as well as the quantification of the formed complex are carried out in vitro. Here, the quantity of complexes is indicative of the degree of NK-dependent triggering of HIV replication in said subject and thus a measure of the severity or progression of HIV infection. Complex formation may be compared to the amount of complex formation with complex formation in a biological sample obtained from a subject not infected with HIV or with complex formation obtained from the same subject at a different time, such as prior to infection or during a prior acute or chronic infection. This method may also involve other diagnostic tests to exclude or control for acute and/or chronic inflammation attributable of HMGB1 not associated with HIV infection in the subject and may be accompanied by other diagnostic tests for the presence of or HIV viral load in the subject.

Prior to performance of a diagnostic assay according to the invention, the biological sample, such as serum or plasma, may be treated with acid to separate HMGB1 from other proteins that bind to HMGB1, see Gaillard, et al., PLOS One 3(8) e2855, pages 1-9 (2008) which is specifically incorporated by reference as teaching high-sensitivity methods for detection and measurement of HMGB1 protein, including acid treatment. Such treatment increases the number of HMGB1 epitopes available for recognition by antibodies. Acid treatment is optional, since some antibodies to HMGB1 bind regions of the protein not blocked by the binding of other proteins.

Antibodies used for diagnostic applications need not block the activity of HMGB1 and may be polyclonal or monoclonal antibodies or antibody fragments that bind to HMGB1. Such antibodies may be derived by known methods from animals such as mice, rats and rabbits or produced by other methods well-known in the art. Antibodies or other HMGB1 binding agents used for diagnostic or monitoring HMGB1 levels may be formulated into kits which include written or electronic instructions regarding how to perform the assay, buffers, preservatives, negative and/or position control samples, solid supports, and containers or packaging materials.

BRIEF DESCRIPTION OF THE DRAWINGS

FIGS. 12(a)-(b): (a) aNK cells induce apoptosis of uninfected iDCs by upregulating TRAIL receptor (DR4) expression at iDCs surface, increasing thus DC's sensitivity to TRAIL-dependent apoptosis. (b) HIV-1-infected DCs are resistant to aNK-induced apoptosis by an HMGB1-dependant mechanism. Consequently, aNK cells participate to the persistence of infected DC, DC-dependent HIV transmission to CD4 T cells and establishment of HIV reservoirs.

FIG. 17 (A)-(B). Impact of HAART on T cell subsets (A) and HIV viral load (B) measured at different times (in months) following the HAART. *: $p<0.001$ and : $p<0.05$.

FIG. 20 (A)-(B). Study of correlation between serum HMGB1 and anti-HMGB1 antibody concentrations (A), and between anti-HMGB1 antibodies and HIV-RNA viral load (B). Spearman's correlation test. The correlation coefficient r, probability of correlation (p) and number of samples analyzed (n) are indicated.

EXAMPLES

Figure 1E:
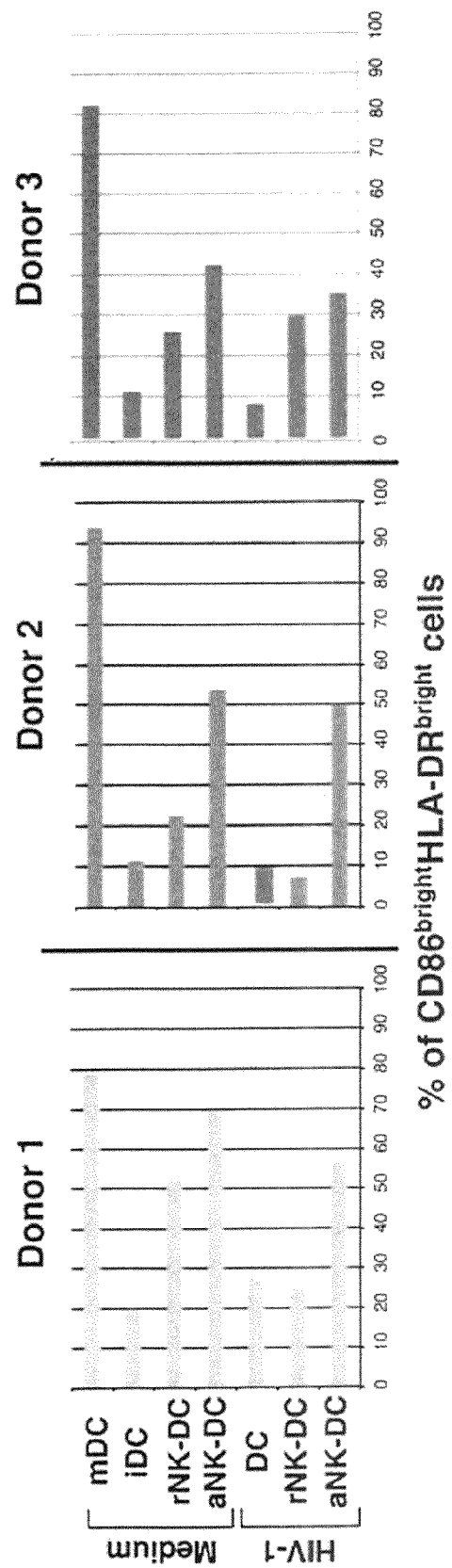
FIG. 1 (a)-(e). aNK cells induce the maturation of primary immature HIV-1-infected DCs. (a) iDCs, generated from purified $CD14^+$ monocytes in the presence of IL-4 and GM-CSF, were cocultured during 24 h with aNK cells at different ratios. DC survival was determined by flow cytometry with the 7-AAD assay. Surviving DCs were identified as $7AAD^-$ $CD56^-$ cells. Data represent three independent experiments and values are means±sd. (b) aNK cells induce the maturation of iDCs. Flow cytometry analysis of iDCs, which were either infected with R5-HIV-1 BaL (1 ng/ml of p24) for 3 h or uninfected, were incubated with rNK cells or aNK cells at a ratio of 1:5. Co-staining with HLA-DR and CD86 specific antibodies allowed the identification of mature DCs ($CD86^{bright}HLA-DR^{bright}$). Data from a representative experiment out of three independent experiments are shown. (c) The conditions of infection used in this study were those of a productive infection of iDCs, as shown at day 3 by a significant p24 detection in culture supernatant of infected iDCs and intracellular detection by flow cytometry of p24 in DC targeted by CD40 expression. Experiments were performed on DCs from three independent donors, and values are means±sd (d) HIV-1 infection does not induce by itself the maturation of iDC, as shown by CD86/HLA-DR dual staining of iDCs infected with 0.001 to 10 ng/ml p24 HIV-1. The proportion of mDCs induced by LPS (DC0) (78.1% $CD86^{bright}HLA-DR^{bright}$) is shown as a positive control. (e) The proportion of mature $CD86^{bright}HLA-DR^{bright}$ DCs induced in the indicated cocultures of infected or uninfected iDCs with either rNK or aNK cells are shown. These experiments have been performed on primary cells from a number of donors, and representative data from three of them are shown. When indicated, statistical analyses were made with the non parametric Mann-Whitney test. * p<0.05, ** p=0.02.

HMGB1 is a nuclear protein that is present in almost all eukaryotic cells, and it functions to stabilize nucleosome formation and acts as a transcription-factor-like protein that regulates the expression of several genes. It is also a cytokine, secreted by activated macrophages, mature dendritic cells (DCs) and natural killer (NK) cells in response to injury, infection or other inflammatory stimuli.

Early stages of viral infections are associated with local recruitment and activation of effectors of innate immunity, i.e. NK cells and DCs. DCs are essential for both antigen-presentation and activation of naive CD4$^+$ T cells, and further Th I polarization. DCs also constitute early targets for HIV and contribute to HIV persistence by integrating proviral DNA. DC maturation and homeostasis is controlled by a crosstalk between DC and NK cells. The contribution of this cross talk to susceptibility of DCs to HIV replication was previously unknown.

Activated NK cells (aNK) provide a source of HMGB1, which is released during the contact between NK cells and immature DCs (iDCs) and promotes the maturation of iDCs and the induction of IL-12-dependent T-helper-1 responses. Following infection of iDCs with HIV-1, DCs were no more susceptible to NK-dependent IL-12 polarization, and thus no more able to induce a Th1 response. In addition, NK-dependent DC maturation and survival was associated with an increased production of HIV-1 p24 and an increased expression of proviral DNA by DCs. NK-dependent increased replication of HIV-1 in DCs was inhibited by antibodies specific for HMGB1 and by glycyrrhizin, known to interact specifically with HMGB1, suggesting an important role for this cytokine in this process. As a corollary, rh-HMGB1 had a direct effect on infected DCs, enhancing dramatically the production of p24 in culture supernatants. A strong stimulating effect of HMGB1 on HIV replication in DCs was also observed in aNK: iDC cocultures. The addition of HMGB1-specific neutralizing antibodies or glycyrrhizin abrogated HIV-1 production by infected DCs cultivated alone or in the presence of aNK cells. Altogether, these results indicate that HMGB1 triggers HIV-1 replication and increases HIV-DNA in infected DCs, whether added as a recombinant human protein on infected DCs or produced by aNK cells during NK:DC cross talk.

Although direct infection of DCs is less efficient than infection of CD4+ T cells[40, 41] an increasing amount of evidence indicates that long-term HIV transmission that is mediated by DCs depends on viral production by the DCs[42, 43, 44], and HIV-infected DCs in vivo might function as viral reservoirs during migration to the lymphoid tissues, thereby helping to spread viral infection.

The inventors have shown for the first time that activated NK cells contribute to the establishment of viral reservoirs in HIV-1-infected DCs. The inventors shown herein NK-cell activating capacity of HIV-1-infected iDCs and the crucial involvement of HMGB1, produced during aNK-iDC crosstalk, in the stimulation of HIV-1 replication and proviral DNA expression in DCs. A strong impairment of mature infected DCs to induce Th1 polarization following their cross-talk with NK cells has also been demonstrated. These observations led to novel therapies to inhibit the ability of HIV to efficiently promote its dissemination and escape the host immune system.

Interaction of NK cells with autologous iDCs results in reciprocal activation, and this interaction appears crucial in the initiation/amplification of the early phases of an immune response, before T cells are generated[11]. NK cells trigger iDCs to mature, and this occurs through an HMGB1-dependent mechanism[20]. NK-dependent maturation of iDCs has been reported to involve a functional polarization of DCs, with increase in intracellular free $Ca^{2+}$ concentration, cytoskeleton rearrangement, accumulation of secretory lysosomes at the NK/DC synapse, and regulated expression of IL-18 toward the interacting NK cells. In turn, NK cells secrete large amounts of HMGB1, which induces maturation of DCs[20]. The inventors have substantiated the involvement of HMGB1 in NK-dependent DC maturation during NK-DC contact, as shown by the inhibitory effect of anti-HMGB1 antibodies or glycyrrhizin, known to interact specifically with HMGB1[31]. Confocal microscopy analyses and HMGB1 detection in cell-free culture supernatants demonstrated that HMGB1 was not only expressed and secreted by primary NK cells, as reported[20], but it was also produced by isolated DCs, the level of HMGB1 release being linked to their maturation stage. An extremely high level of HMGB1 was detected when iDCs where put in contact with aNK cells, similar to the one released by mature DCs. Interestingly, confocal microscopy analysis of NK-DC conjugates showed that both cells expressed the cytokine. HMGB1 receptor, RAGE, was found rapidly induced following DC interaction with aNK cells, and was further down-regulated, compatible with the implication of HMGB1 in NK-dependent DC maturation. In addition to contributing to DC maturation, HMGB1 has been shown to act as a chemoattractant on iDCs[45], and to be also required for migration of mature DCs in response to CCR7 and CCR4 ligands[46], both activities being mediated by RAGE[46,46]. Thus HMGB1 acts as an alarmin, having activating and chemotactic effects on DCs, and stimulating then the migration of DCs from inflamed tissues to the draining lymph nodes[45]. These properties of HMGB1 have to be taken into consideration in the context of an uncontrolled viral infection, such as that induced by HIV.

Productive infection of iDCs with HIV-1 preserved NK-dependent phenotypic DC maturation, as shown by the frequency of $CD86^{bright}HLA-DR^{bright}$ DCs, while HIV itself didn't induce DC maturation in the range of p24 concentrations used (0.001 to 10 ng/ml). However, the consequence of aNK-DC interaction was a significant enhancement of HIV-1 infection in iDCs. This was shown by several means, indicating an increased frequency of p24+ DC, associated with a significant enhancement of p24 release in NK-DC culture supernatant, and this was confirmed by immunofluorescence at the single cell level. Moreover, NK-DC cross-talk resulted in a dramatic increase in proviral HIV-1 DNA expression in DCs. Considering the crucial role of HMGB1 during the reciprocal activation of DCs and NK cells, its contribution to the triggering of HIV-1 replication in iDCs with blocking anti-HMGB1 antibodies or glycyrrhizin was evaluated. The strong blocking effect of these inhibitors on p24 release indicates the involvement of HMGB1 in the process. It is noteworthy that both inhibitors also decreased significantly HIV-1 replication in 24 h cultures of infected iDCs, in the absence of NK cells. This is likely due to the spontaneous release of HMGB1 by iDC, shown here and previously reported[46], which was preserved following their infection with HIV-1. These observations reveal a pivotal role for HMGB1 in controlling HIV-1 replication in DCs. As a corollary, it was demonstrated that rh-HMGB1 significantly increased p24 release in culture supernatants of infected DCs and of aNK-infected DC cocultures. These data may have important implications in the understanding of HIV pathogenesis, since plasma HMGB1 levels were found elevated in chronically HIV-1-infected patients, with the highest concentrations in patients with clinical complications[47]. Moreover, exogenous HMGB1 was reported to induce in vitro the reactivation of HIV-1 in PBMCs from HIV-1-infected patients under antiretroviral therapy[39].

Secreted HMGB1 is necessary for proliferation, survival, and polarization of naïve CD4 T cells after activation by allogeneic DCs, and these effects involve RAGE expressed by DCs[48]. Here, it was shown that, in syngeneic conditions, HMGB1 was not able by itself to induce Th1 polarization. Indeed, no Th1 response was induced in the presence of HIV-1-infected DCs, though they continued to produce normal levels of HMGB1, while being inhibited in the release of IL-12 and IL-18. Recent studies highlighted the essential role of NK cells in the modulation of Th1 polarization, suggesting that they trigger IL-12 and IL-18 release by DCs, promoting the production of IFN-γ by NK cells that in turn trigger the differentiation of T cells towards Th1 cells[49,50]. The essential role of IL-12 and IL-18 on Th1 differentiation is confirmed here, since the defect of HIV-1 infected DCs to produce increased amount of IL-12 and IL-18 in response to NK cell activation was associated with a defective Th1 polarization. This defect was directly linked to HIV-1 replication in DCs, as shown by the positive effect of the HIV inhibitor AZT. These observations suggest that some of the functional alterations reported in DCs from HIV-infected patients[51,52], such as a decreased secretion of several cytokines, including IL-12, and an impaired ability to prime autologous CD4 T cells, may be linked to a defective NK-DC cross-talk, as suggested recently[30].

The inventors show that activation of HIV-1 replication and the establishment of viral reservoirs in HIV-1-infected DCs is dependent on a cross-talk between aNK cells and autologous DCs, and have identified the pivotal role of HMGB1 in this process, produced both by NK cells and DCs during their cross-talk, and showed that NK-dependent triggering of HIV replication in DCs is completely abrogated by glycyrrhizin, which binds specifically to HMGB1, or by blocking with anti-HMGB1 antibodies. In addition, a strong impairment of the ability of HIV-1-infected DCs to induce Th1 polarization following their cross-talk with NK cells has been demonstrated. Methods of treating and monitoring HIV infection are described based on the role of NK-DC cross-talk in promoting viral dissemination, and on in vivo involvement of HMGB1 in the triggering of viral replication and replenishment of viral reservoirs.

Example 1

Activated NK Cells Induce the Maturation of Autologous Primary Immature Dendritic Cells Infected with HIV-1

The role of NK cells on DC maturation was investigated by generating monocyte-derived DCs from isolated monocytes and coculturing them with NK cells purified from the same donor. NK cells were either resting (rNK) or activated by a combination of PHA and IL-2 (aNK). 24 h of coculture of aNK cells with autologous immature DC (iDC) induced either the survival or apoptosis of iDCs, dependent on NK-DC ratio, consistent with previous reports[14]. Indeed, aNK-DC ratio of 5:1 induced DC apoptosis, while 1:5 ratio induced DC survival. (FIG. 1a). iDCs survival at a NK-DC ratio of 1:5 was associated with their maturation, as shown by the increased coexpression of the maturation markers CD86 and HLA-DR (72.1% of $CD86^{bright}HLA-DR^{bright}$ DCs were induced by aNK cells compared to 15.3% at baseline) (FIG. 1b), a feature of mature DCs. Under the same experimental conditions, rNK cells had a weaker effect on DC maturation, as judged by the proportion of $CD86^{bright}HLA-DR^{bright}$ DCs (FIG. 1b,e). Following infection of iDC with HIV-1, NK-dependent maturation of iDCs was not altered (FIG. 1b), under conditions of productive infection of iDCs, measured at day 3 by p24 release in culture supernatant and intracellular staining of iDC for p24 (FIG. 1c).

The direct effect of HIV on DC maturation was found at concentrations ranging from 0.001 to 10 ng/ml, where HIV was unable to increase the expression of the maturation markers CD86 and HLA-DR, in contrast to LPS, used as a positive control as a strong inducer of DC maturation (FIG. 1b,d). Data from three representative donors, shown in FIG. 1e, confirm the high impact of aNK cells on maturation of iDC after 24 h of coculture, whatever the infected or uninfected status of iDC. These data show that productively HIV1-infected iDCs maintain a normal susceptibility to maturation induced by NK cells during the NK-DC cross-talk.

Example 2 aNK-DC Cross-Talk Triggers HMGB1 Expression in Both NK Cells and DCs

Figure 2A:
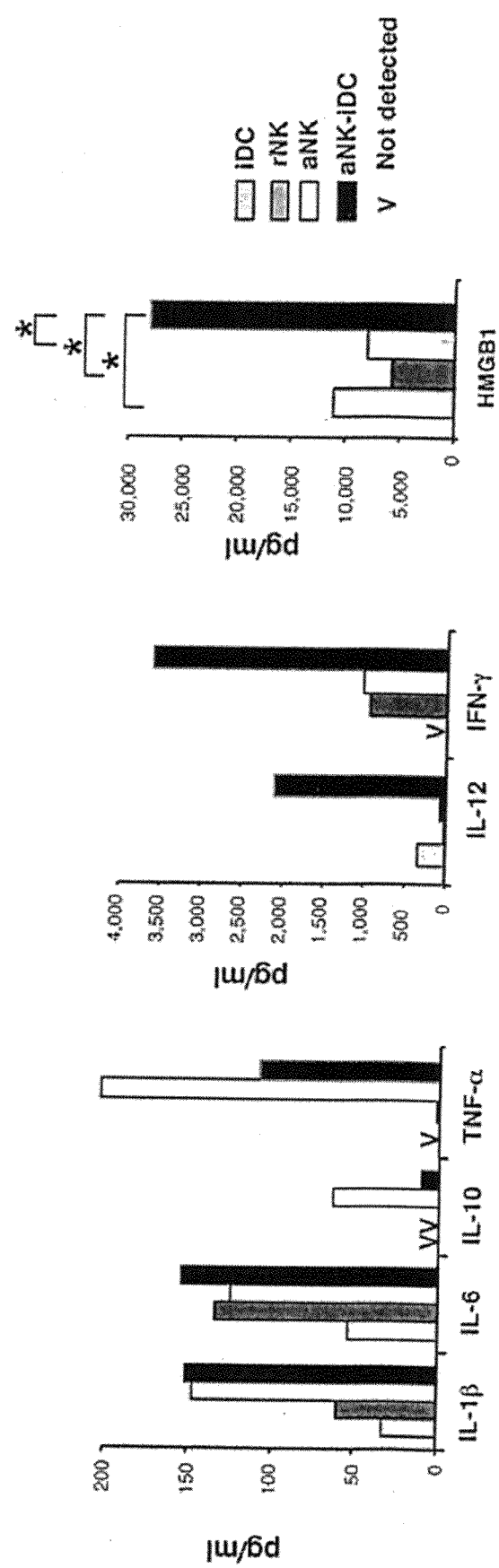
FIG. 2 (a)-(g). aNK-DC cross-talk triggers HMGB1 expression in both aNK cells and DCs. (a) 24 h cell-free culture supernatants of iDCs, rNK cells, aNK cells ($10^6$/ml), or cocultures of aNK cells and iDCs (ratio 1:5) were tested for cytokine content. MAP technology was used to quantify IL-1β, IL-6, IL-10, TNF-α, IL-12 and IFN-γ, whereas HMGB1 was quantified by ELISA. * p<0.05 (non-parametric Mann-Whitney test). (b) HMGB1 expression was detected by immunofluorescence (in red) in freshly sorted blood NK cells. Counterstaining with DAPI (in blue) showed the nuclear localization of HMGB1. (c) Incubation of aNK cells with HIV-1 inhibits HMGB1 secretion. Left panel: aNK cells ($10^6$ cells/ml) were incubated in medium or with R5-HIV-1Ba-L (1 ng/ml of p24) for 3 h and tested for HMGB1 production 21 h later. Data represent three independent experiments and values are means±sd. Right panel: immunofluorescence analysis of HMGB1 expression in the same preparations of aNK cells. (d) HMGB1 production during aNK-iDC cross-talk is not inhibited by HIV-1 infection of iDCs. iDCs were incubated for 3 h in medium or with HIV-1 BaL (1 ng/ml of p24) and further cocultured for 21 h with aNK cells (aNK:iDC ratio 1:5). HMGB1 concentration was then measured in culture supernatants. Data represent the mean±sd of three independent experiments. (e) Immunofluorescence confocal analysis of HMGB1 expression in uninfected or HIV-1-infected iDCs. Upper panel: non infected iDCs; middle panel: HIV-1-infected and replicating iDCs, as shown by intracellular p24 staining; lower panel: iDCs incubated with HIV-1 but negative for intracellular p24 expression. (f) Mature DCs were generated by 48 h stimulation of iDCs with LPS (DC0), soluble CD40L (DC1) or LPS+PGE2 (DC2). DC0, DC1 and DC2 were incubated for 3 h in medium or infected with R5-HIV-1BaL (1 ng/ml of p24) and further incubated in medium for 21 h. HMGB1 quantification in culture supernatants was performed. The mean±sd of three independent experiments is shown. (g) Immunofluorescence analysis of HMGB1 expression in conjugates of aNK cells and uninfected (upper panel) or HIV-1-infected DCs (lower panel) in a 24 h coculture. DCs are $DC-SIGN^+$ and both aNK cells and DCs express HMGB1 in these conjugates. Pictures from one representative experiment out of three conducted with different primary cell preparations are shown.
Figure 2B:
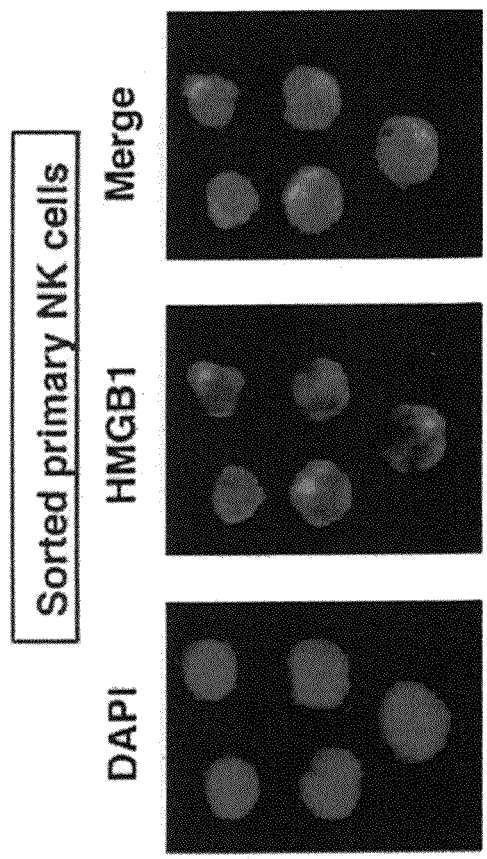
Figure 2C:
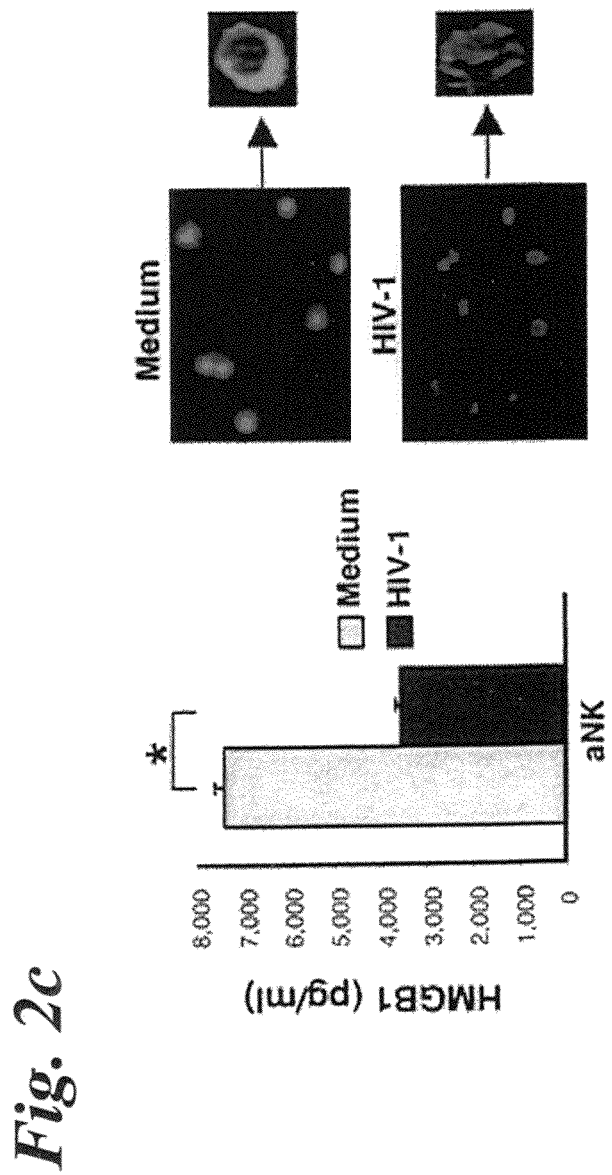
Figure 2D:
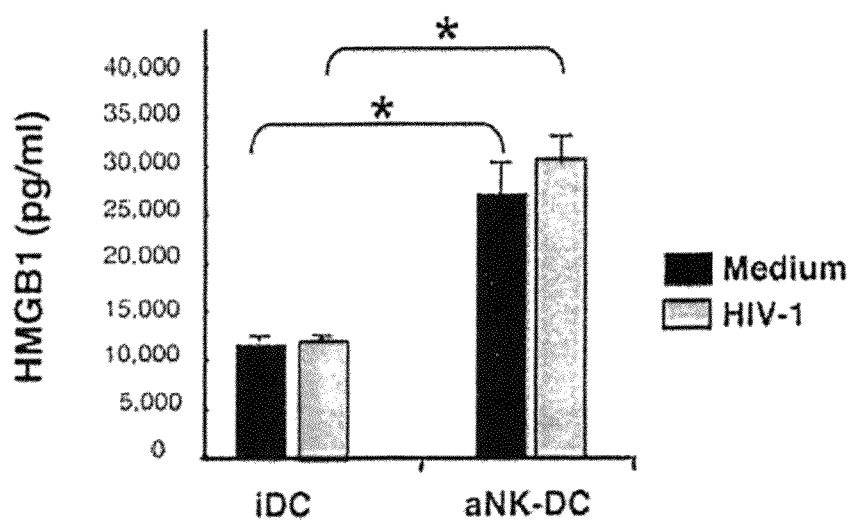
Figure 2E:
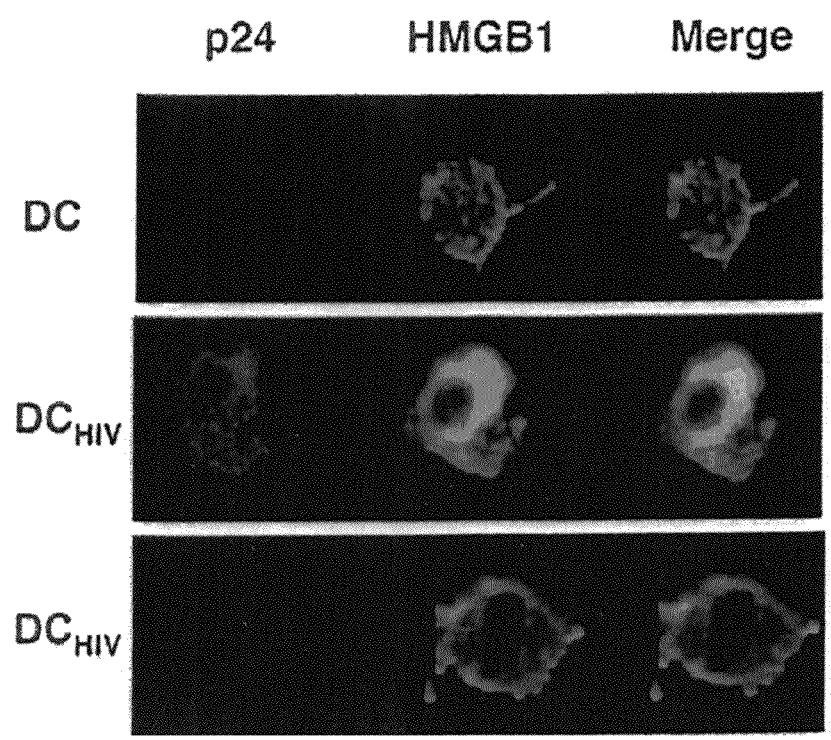
Figure 2F:
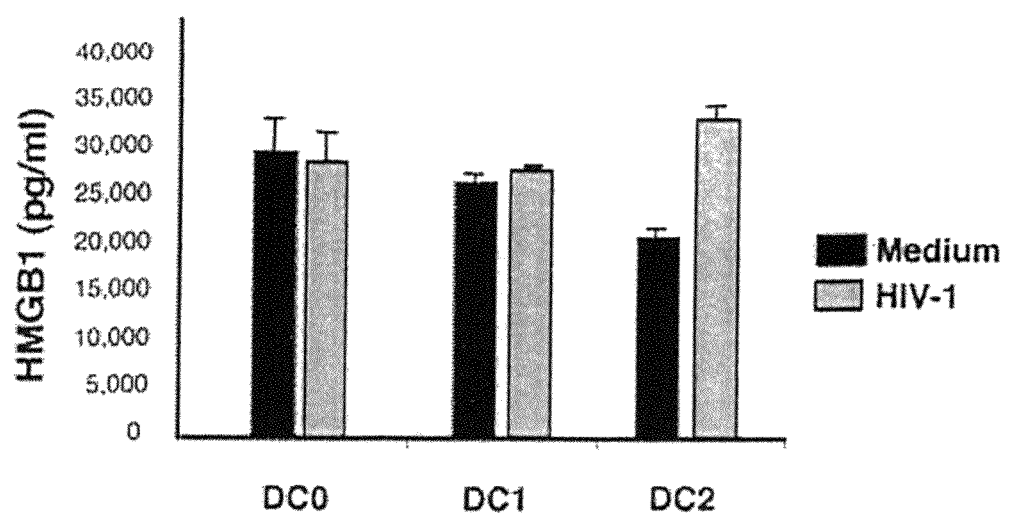
Figure 2G:
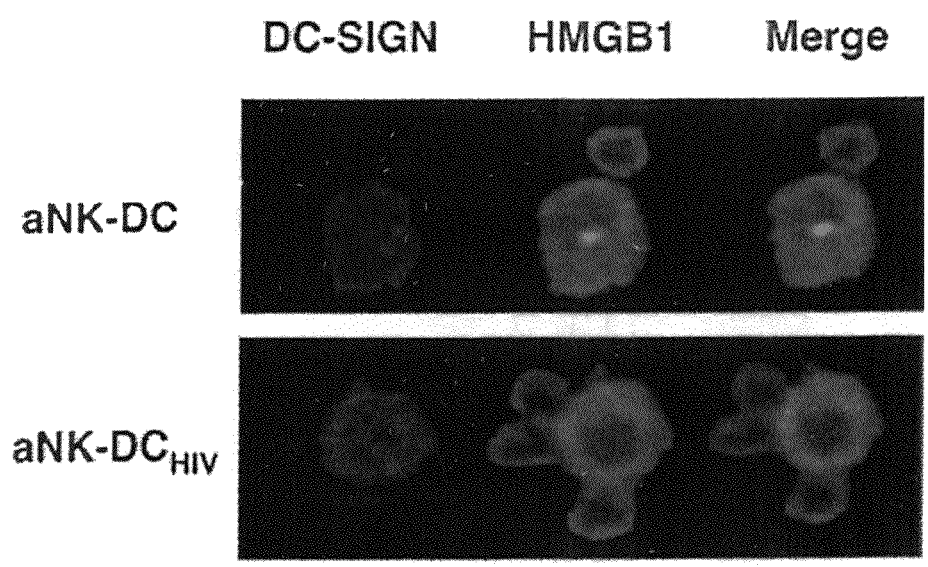

In order to identify the molecules involved in aNK-dependent maturation of iDC, a multianalyte profiling (MAP) was employed to map the key cytokines produced in 24 h culture of iDC, NK cells and aNK:iDC. iDC released low amounts of IL-1β, IL-6 and IL-12, and they did not produce IL-10 or TNF-α. Following their coculture with aNK cells, a proinflammatory cytokine profile was induced, with a high increase in IL-12 secretion, significant levels of TNF-α and IFN-γ, both □ derived from NK□ cells, and no production of IL-10 (FIG. 2a). Interestingly, high levels of HMGB1 were detected in those culture supernatants, originating both from iDC and NK cells, and aNK:iDC cocultures resulted in a strong enhancement of HMGB1 concentration in culture supernatants (FIG. 2a). It was confirmed that at the single cell level, by confocal microscopy, that NK cells were able to produce HMGB1, detected in the nucleus of freshly isolated NK cells (FIG. 2b), and further translocated to the cytoplasm in aNK cells (FIG. 2c). Following 3 h incubation with HIV-1, aNK cells showed a strong decrease in HMGB1 expression, detected both in culture supernatants and by confocal microscopy (FIG. 2c). HMGB1 level reached then a level comparable to that of rNK cells (FIG. 2a). The inventors verified that NK cells were not able to replicate HIV-1, as shown by the lack of p24 detection in culture supernatant and the lack of intracellular p24 staining (detected by FACS) in NK cells (data not shown). HMGB1 was also secreted by iDCs and, once infected, they still produced comparable amount of the cytokine in culture supernatants (FIG. 2d). HMGB1 was mostly detected in the cytoplasm of iDCs, whether infected by HIV-1 or not (FIG. 2e), and p24 expression in infected DCs did not alter HMGB1 expression, as shown by dual intracellular staining for p24 and HMGB1 (FIG. 2e). When iDCs were cocultured with aNK cells, a strong induction of HMGB1 secretion in culture supernatants was observed (FIG. 2d), reaching levels comparable to those produced by mature DCs, i.e. DC0, DC1 and DC2 (FIG. 2f). Strikingly, HIV-1 infection of iDC did not affect the amount of HMGB1 produced in NK-DC cocultures (FIG. 2d) and in cultures of mature DCs (FIG. 2f). Confocal microscopy analysis showed the formation of conjugates between aNK cells and iDCs, which were also observed when aNK cells were cocultured with HIV-1-infected DCs, and both cells expressed HMGB1, whatever the infected status of DCs (FIG. 2g). These results demonstrate that HMGB1 is expressed both by NK cells and iDCs during NK-DC cross-talk, and this process is not altered by HIV-1 infection of iDCs.

Figure 3A:
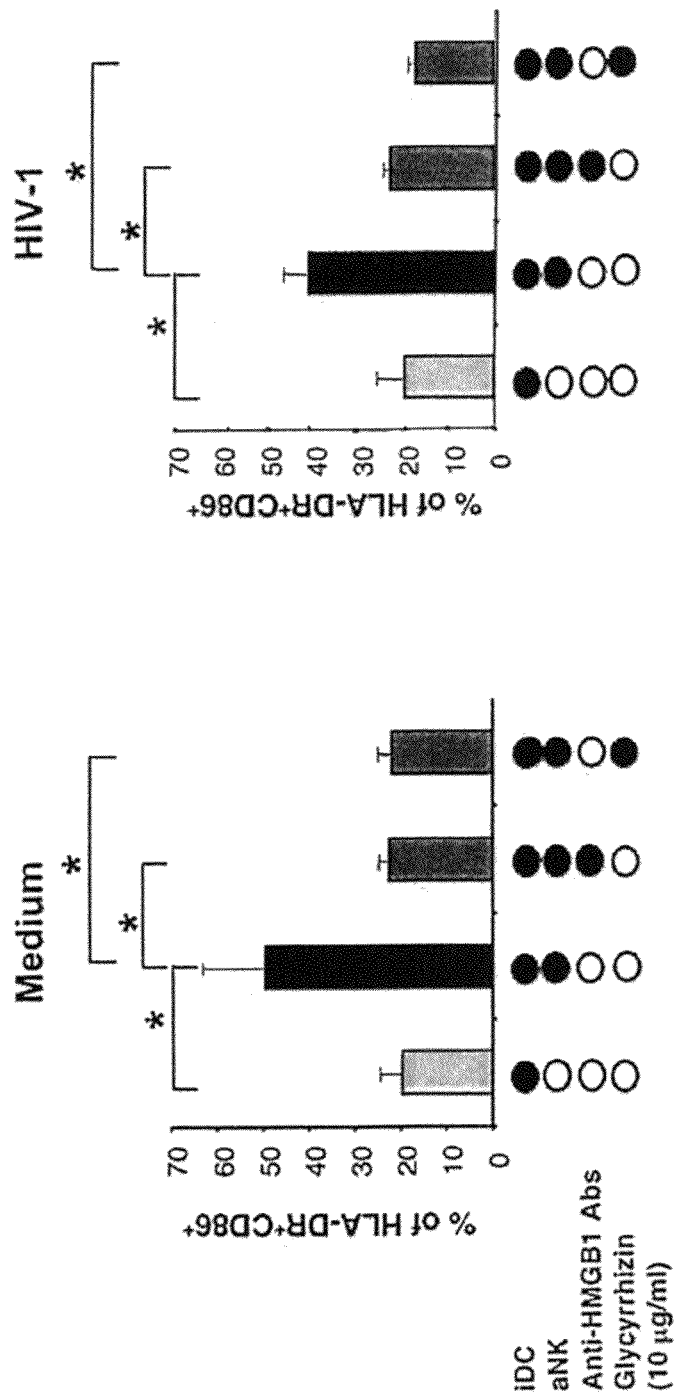
FIG. 3 (a)-(e). aNK-dependent maturation of HIV-1-infected iDCs is mediated by HMGB1 and involves RAGE. (a) Left panel: iDCs were cultured for 24 h either alone or with aNK cells, in the presence of blocking anti-HMGB1 antibodies (10 µg/ml) or glycyrrhizin (10 µg/ml). The maturation status of DCs was determined by flow cytometry with CD86 and HLA-DR—specific antibodies. Right panel: same experiment, but performed with HIV-1 infected iDCs. Data represent mean±sd of at least three independent experiments, and statistical comparisons were made with the non parametric Mann-Whitney test. * p<0.05. (b) iDC ($10^6$ cells/ml) were cultured for 48 h with increasing concentrations (1-10 µg/ml) of rh-HMGB1. Cells were then stained with anti-CD86, -HLA-DR, -CD80, -CD83, DC-LAMP and -CD40 antibodies and analyzed by flow cytometry. (c) Influence of rh-HMGB1 on cytokine and chemokine production (determined by MAP) by DCs. iDCs ($10^6$ cells/ml) were incubated for 48 h in medium or in presence of rh-HMGB1 (1 or 10 µg/ml). As a positive control, iDCs were stimulated with LPS (DC0). (d) Flow cytometry detection of surface expression of RAGE by iDCs, DC0, or iDCs incubated with rh-HMGB1 (1 µg/ml). iDCs were either non infected or infected with HIV-1 (1 ng/ml p24 for 3 h). (e) iDC, DC0, uninfected or HIV-1-infected iDC cocultured for 24 h with aNK cells, were incubated with rh-HMGB1 (1 µg/ml) and subsequently stained with anti-RAGE antibodies and analyzed by flow cytometry. NK cells were excluded from the analysis through the co-staining with CD3- and CD56-specific antibodies (CD3⁻CD56⁺).
Figure 3B:
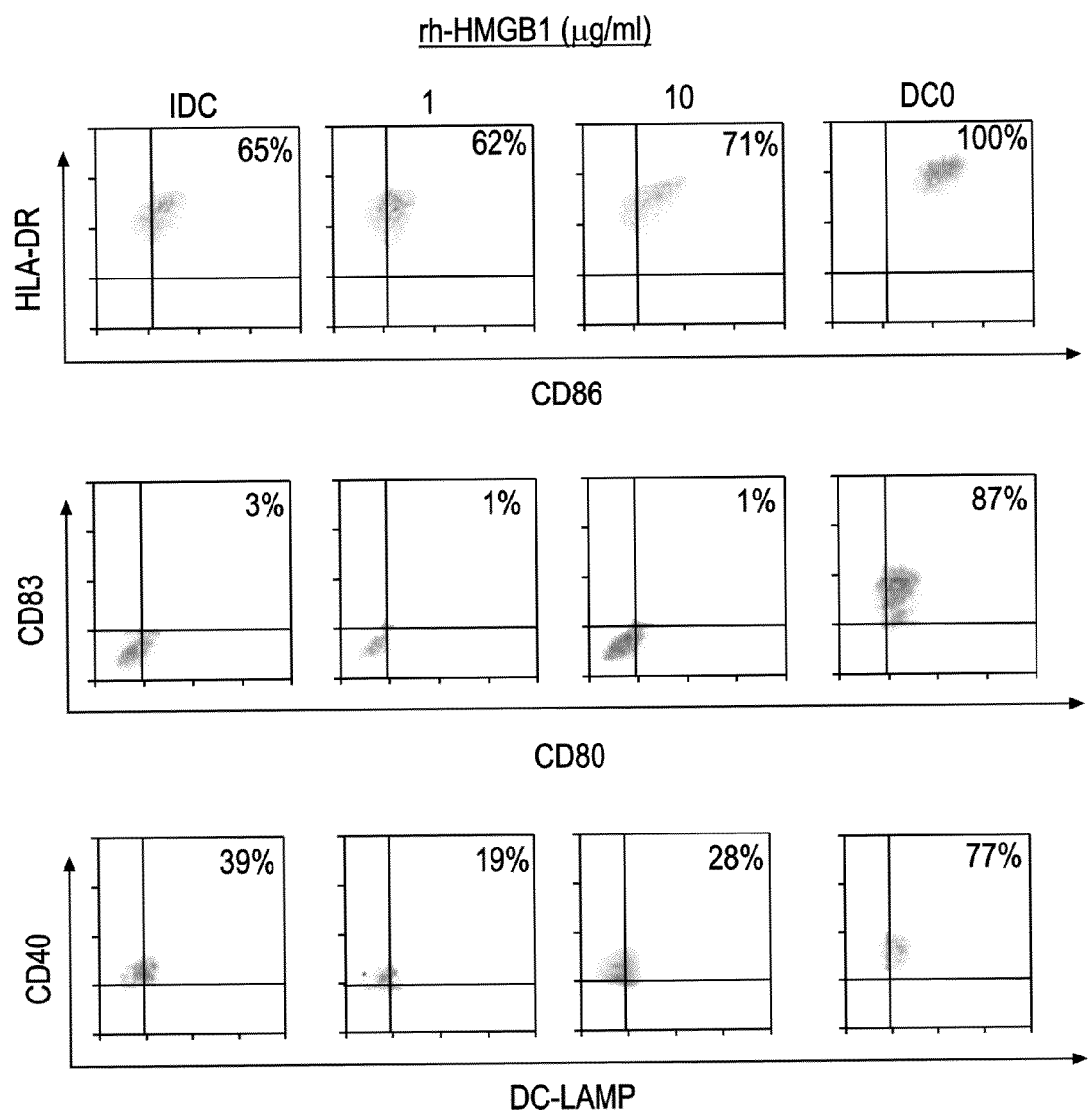
Figure 3C:
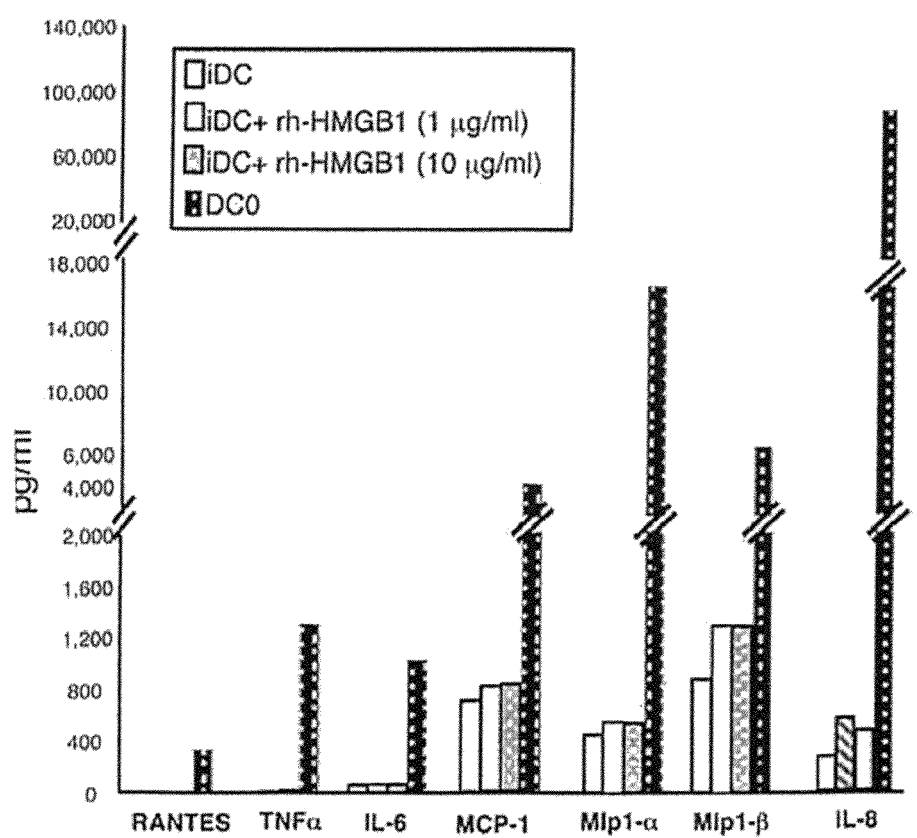
Figure 3D:
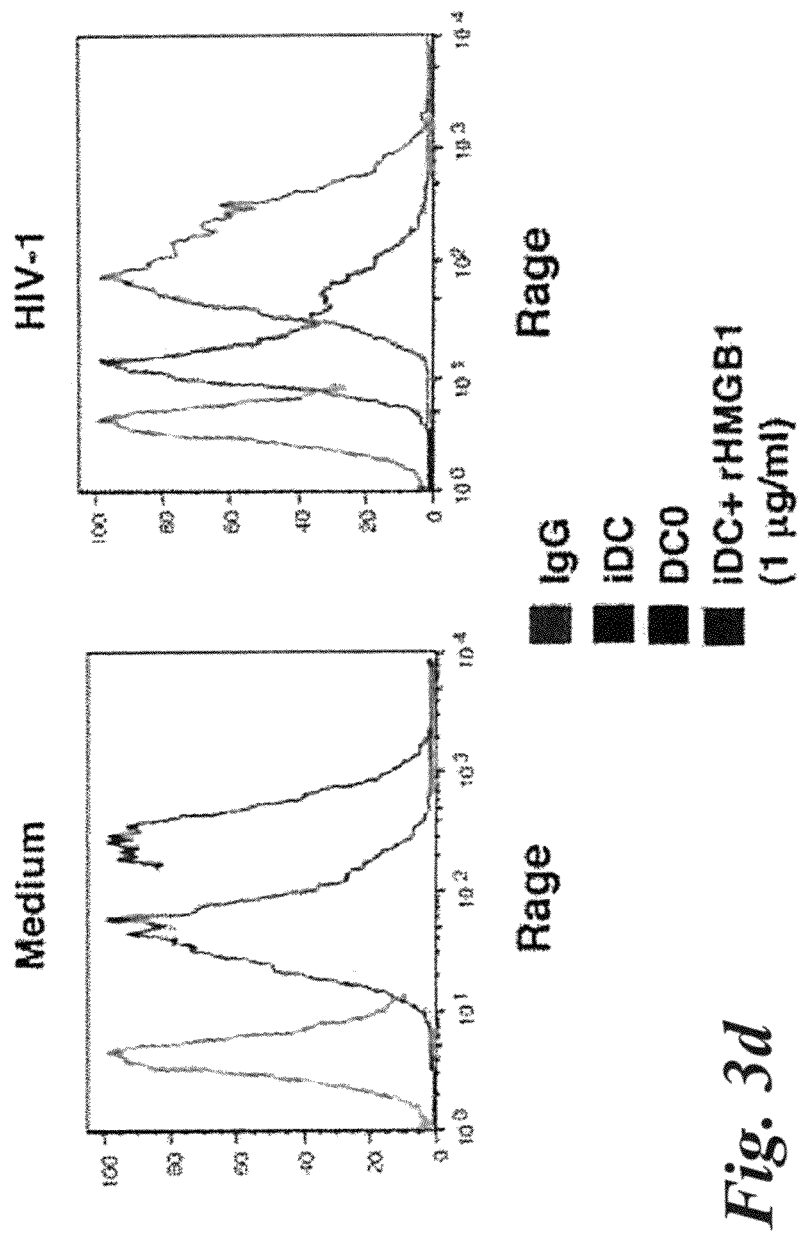
Figure 3E:
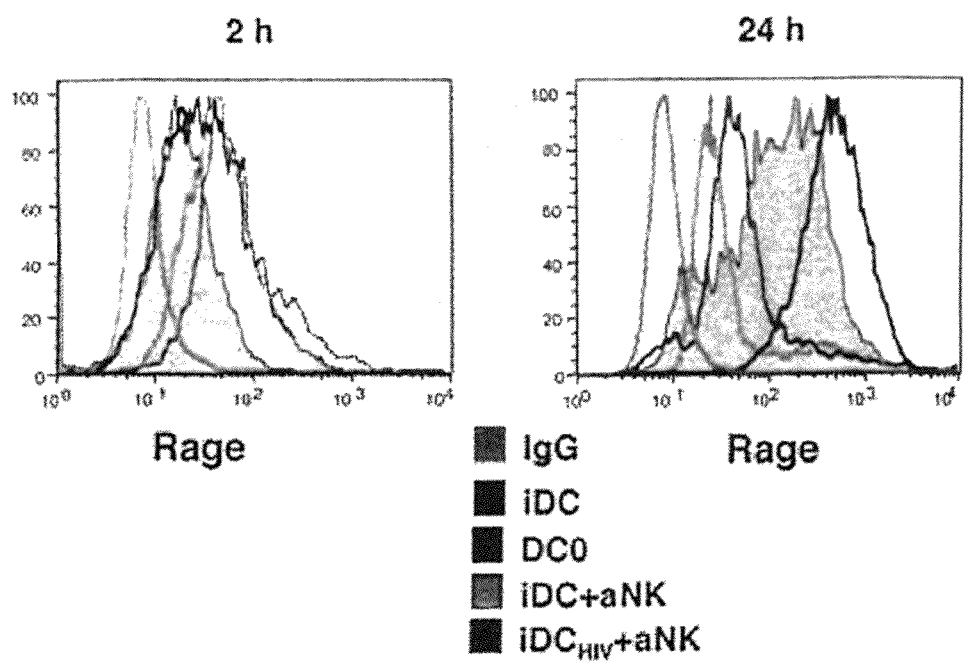

Example 3 aNK-Dependent Maturation of HIV-1-Infected iDCs is Mediated by HMGB1 and Involves RAGE To determine the possible involvement of HMGB1 in NK-dependent DC maturation, glycyrrhizin, which is known to interact specifically with soluble HMGB1 molecule31, was used as well as anti-HMGB1 antibodies (FIG. 3a). These inhibitors, added at the initiation of the 24 h aNKiDC coculture, reduced the proportions of mature DCs (identified as CD86brightHLA-DRbright) to the baseline level observed without aNK cells (FIG. 3a). Similar effect was obtained with infected DCs (FIG. 3a). rh-HMGB1 by itself did not induce phenotypic maturation of iDC, when treated for 24 h with 1 to 10 μg/ml rh-HMGB1, and similar data were obtained at 48 h of culture (FIG. 3b). Indeed, while spontaneous maturation of iDCs was observed after 48 h of culture in medium, as shown by the high percentage of CD86bright HLA-DRbright DCs, 10 μg/ml rh-HMGB1 only weakly increased from 65% to 71% the percentage of these cells. Interestingly, rh-HMGB1-treated DCs were not fully mature, as assessed by the lack of expression of CD80, CD83 and the weak expression of DC-lamp, all fully expressed in mDC (DC0) (FIG. 3b). However, these partially mature DCs were functionally susceptible to rh-HMGB1 as shown by the increased release of the chemokines, MCP1, MIP-1α, MIP-1β and IL-8 by hr-HMGB1-treated DCs (FIG. 3c). HMGB1 receptors include RAGE32, 33 TLR-2 and TLR-434. RAGE was the first identified receptor for HMGB1, it is expressed by a variety of immune cells including T cells, monocytes, macrophages and DCs35, and it is used by maturing DCs for in vivo homing to lymph nodes36. While TLR-2 and TLR-4 were hardly detected on iDC (not shown), RAGE was fully expressed on DCs, as shown by flow-cytometry, and its expression was even higher on mature DC0 (FIG. 3d). Following incubation of iDCs with 1 μg/ml of HMGB1, down-regulation of RAGE was observed, strongly suggesting that this receptor was used by these cells (FIG. 3d). Following DC infection with HIV-1, no change in RAGE levels was detected on iDC and DC0. Incubation of infected DCs with HMGB1 induced similar down-regulation of RAGE (FIG. 3d). The possible involvement of RAGE during NK-DC cross-talk was evaluated with the same approach, comparing RAGE expression on DCs cocultured with aNK cells and DC cultured alone. After 2 h of coculture with aNK cells, DCs showed an up-regulation of RAGE expression, followed by a down-regulation at 24 h (FIG. 3e). Very similar observations were made with HIV-1-infected DCs (FIG. 3e). Thus, HMGB1 is an important factor for the maturation of both uninfected and HIV-1-infected iDCs during NK-DC cross talk, and it involves RAGE, whose expression on iDC is not altered following their productive infection.

Example 4

Figure 4G:
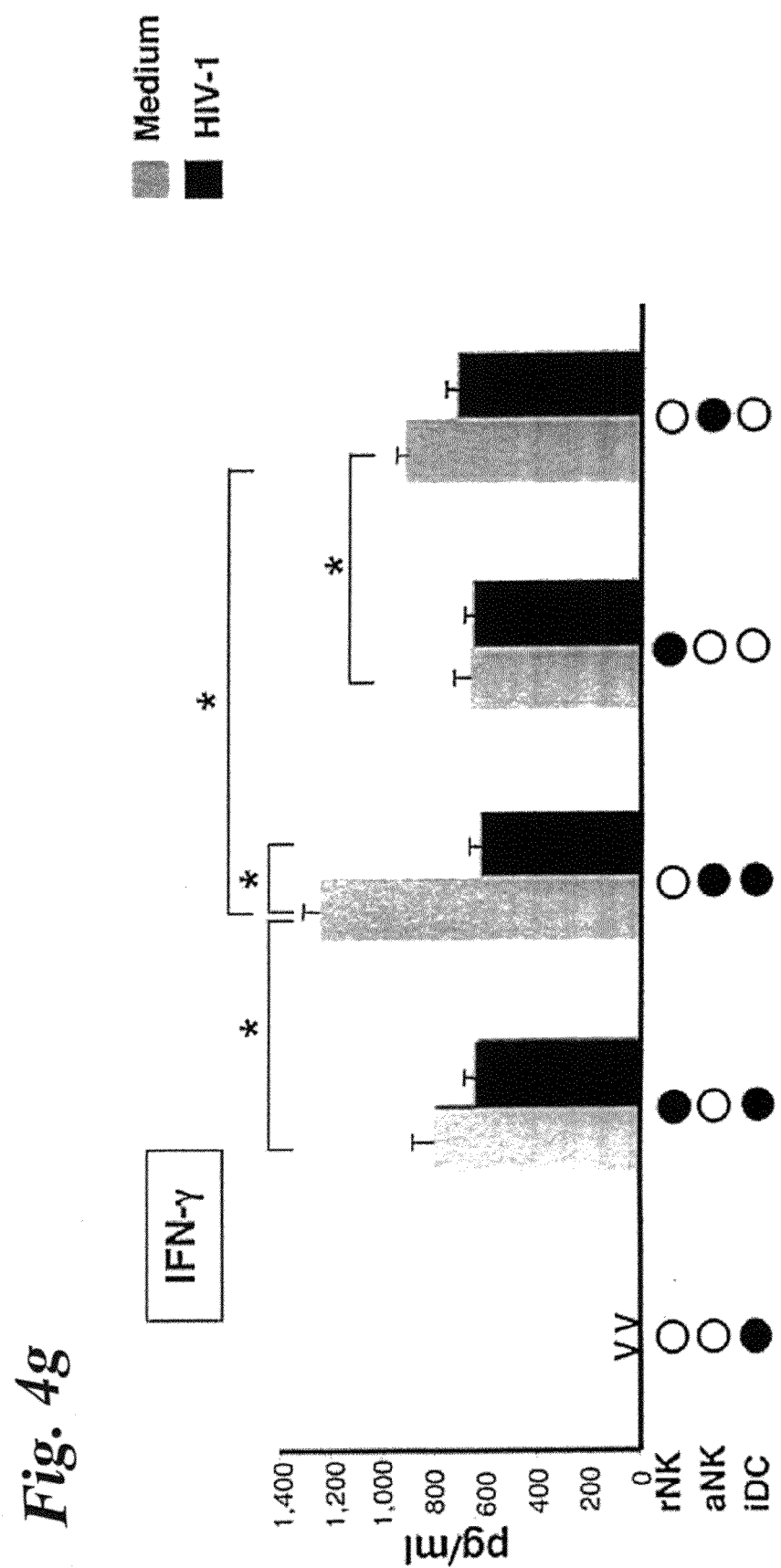
FIG. 4 (a)-(g). Impairment of NK-triggered Th1 polarization by DCs following HIV-1 infection is associated to altered IL-12 and IL-18 production. (a) Th1 polarization by DCs triggered by NK cells was tested by incubating iDC ($10^6$/ml) for 30 mn in the presence of rNK or aNK cells ($2 \times 10^5$/ml). Naïve CD4 T cells ($10^6$/ml) were added to the cocultures and the frequency of T cells producing IFN-γ or IL-4 was determined by flow cytometry 8 days later. The experiment was performed with either uninfected iDCs (b) or HIV-1 infected iDCs (c), or HIV-1 infected iDC in the presence of AZT (1 mM) (d). Culture supernatants of indicated cultures were tested for IL-12 (e), IL-18 (f), and IFN-g (g) content. Data represent the mean±sd of five independent experiments. Statistical comparisons were made with the nonparametric Mann-Whitney test. * p<0.05, **p=0.03.

Impairment of Th1 Polarization by HIV-Infected DCs as a Consequence of a Defective NK-DC Cross-Talk The interaction of NK cells with iDCs results in the induction of type-1 polarized DCs that serve as carriers of the NK cell-derived help for the induction of Th1 responses37. To assess the capacity of DCs, whether infected or uninfected, to polarize a Th1 response following their cross-talk with aNK cells, naïve CD4+CD45RO− T cells were cocultured for 8 days in the presence of DCs and aNK cells, and Th1 polarization was determined by the detection in T cells of the intracellular production of IFN-γ and IL-4, measured by FACS (FIG. 4a). Coculture of naïve T cells with iDCs did not increase the proportion of IFN-γ positive T cells, and similar data were obtained in coculture of naïve T cells with iDCs and rNK cells. In contrast, cocultures of naïve T cells with iDC in the presence of aNK cells induced a significant increase of IFN-γ T cell response (FIG. 4b), suggesting that aNK:iDC cross-talk is essential for Th1 polarization. When the same experiment was performed with HIV-1-infected DC, no Th1 polarization was observed (FIG. 4c). The contribution of HIV-1 replication to the inhibition of Th1 polarization was shown by the addition of AZT, which restored the increased IFN-γ T cell response induced by infected DCs cocultured with aNK cells (FIG. 4d). AZT was used at a concentration inhibiting viral replication in these conditions, as assessed by the dosage of p24 antigen in the supernatants (data not shown). IL-12 and IL-18 are critical cytokines produced by DCs and involved in Th1 polarization. This addressed the question of the impact of aNK-DC cross-talk on the release of these cytokines by DCs. It was found that aNK-DC cross talk triggers both IL-12 and IL-18 secretion by non infected DCs. Importantly, the production of both cytokines was not detected anymore in cocultures of aNK cells and infected DCs (FIG. 4e, f). In addition, the triggering of IFN-γ production by NK cells during aNK-DC cross talk was not detected anymore when the coculture was performed with HIV-1 infected DC (FIG. 4g). Thus, the priming of DCs for Th1 polarization occurs during aNK-iDC cross-talk, though the induction of cytokines such as IL-12 and IL-18 released by DCs, and IFN-γ released by NK cells. Following their infection with HIV-1, iDCs cannot be polarized anymore by aNK cells, due to a defective NK-DC cross-talk. Consequently HIV-1 infected DCs are impaired in their capacity to induce Th1 polarization.

Example 5

Figure 5A:
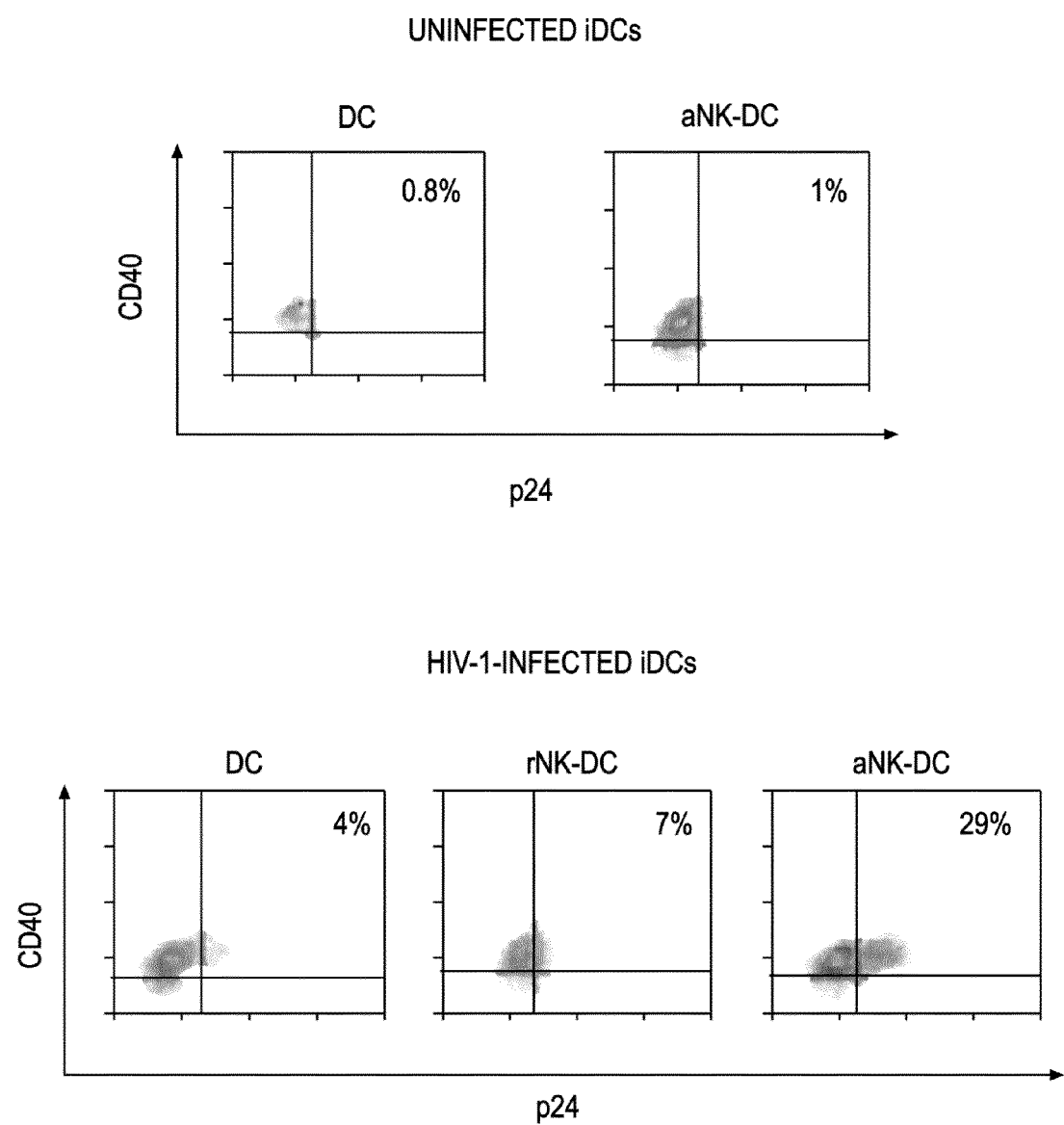
FIGS. 5 (a)-(g). HMGB1-dependent triggering of HIV replication in DC as a consequence of NKDC cross talk. (a) Flow cytometry analysis of p24 intracellular expression in HIV-1-infected (lower panel) or uninfected (upper panel) iDCs (CD40⁺) ($10^6$/ml) following 3 day-incubation, either alone, or in the presence of rNK or aNK cells ($2 \times 10^5$/ml). (b) p24 concentration in culture supernatants of same cultures. Mean±sd of three independent experiments. *p<0.05, non parametric Mann-Whitney test (c) Immunofluorescence analysis of intracellular p24 expression in HIV-1-infected iDCs cultured for 3 days either alone or in the presence of aNK cells. Nuclei are stained with DAPI. (d) Flow cytometry intracellular p24 expression in HIV-1-infected DC0 ($10^6$/ml) cultured either alone or in the presence of aNK cells for 6 days. (e) HIV-1 proviral DNA levels, determined by light cycle analysis on cells from indicated cultures. (f) and (g) p24 concentration in culture supernatants of HIV-1-infected mature DCs cultured either alone or in the presence of rNK or aNK cells for 6 days. Mean±sd of three independent experiments. Statistical comparisons were made with the non parametric Mann-Whitney test. * p<0.05. One representative experiment out of three conducted with different primary cells preparations is shown.
Figure 5B:
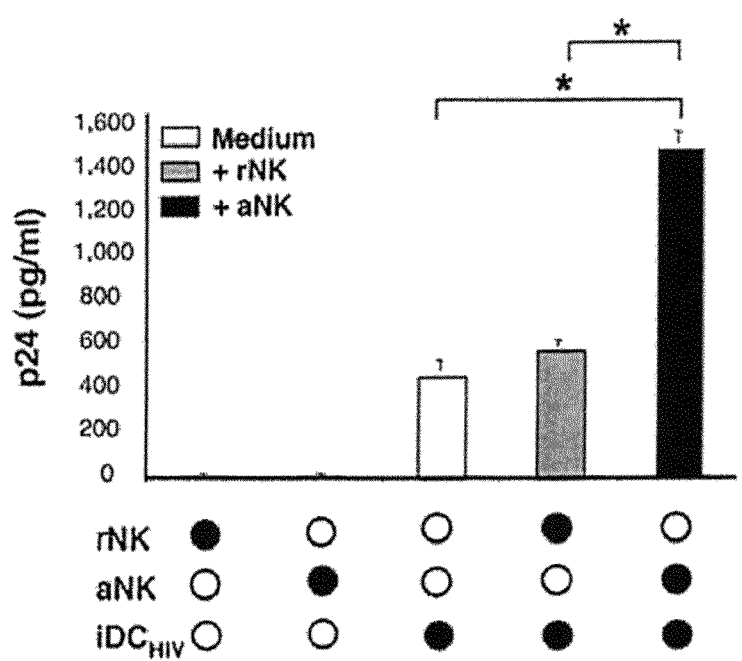
Figure 5C:
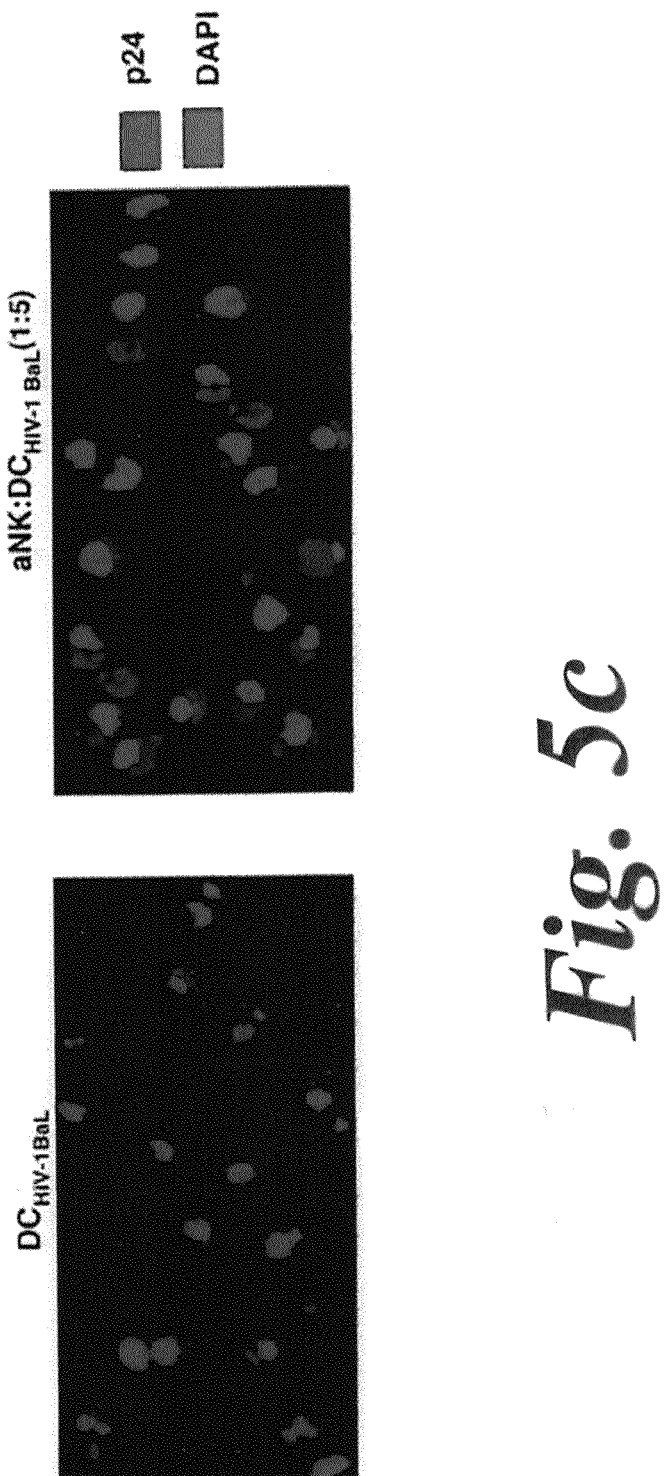
Figure 5D:
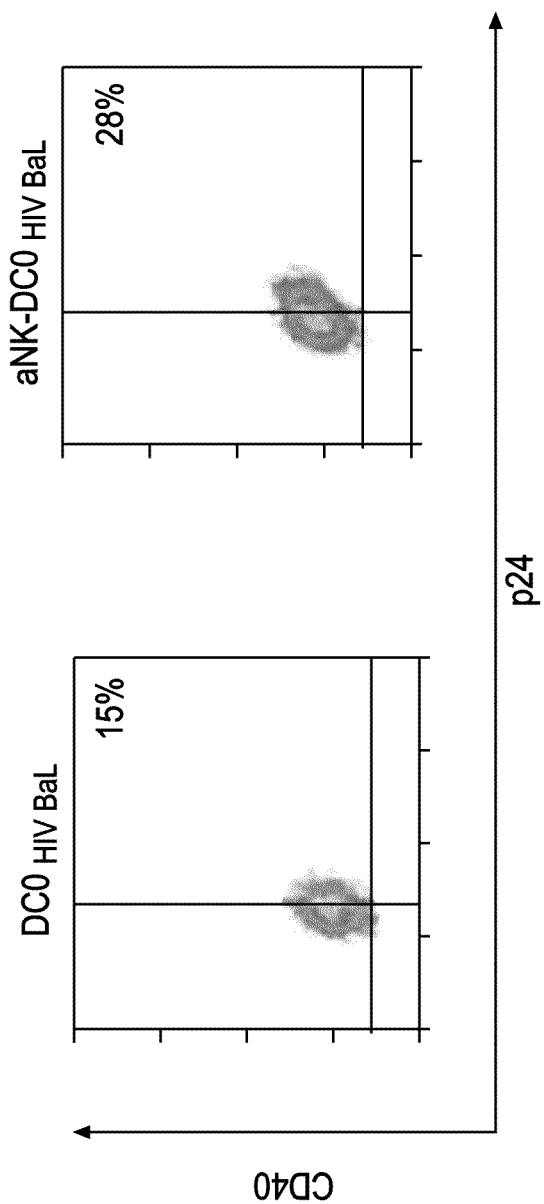
Figure 5E:
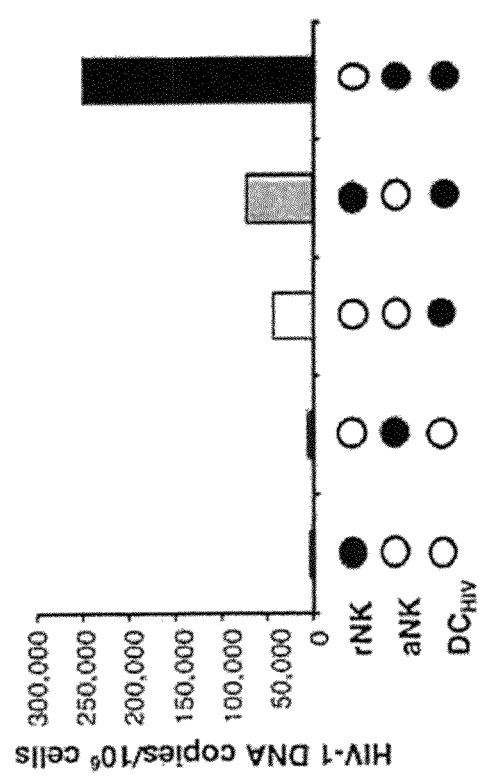
Figure 5F:
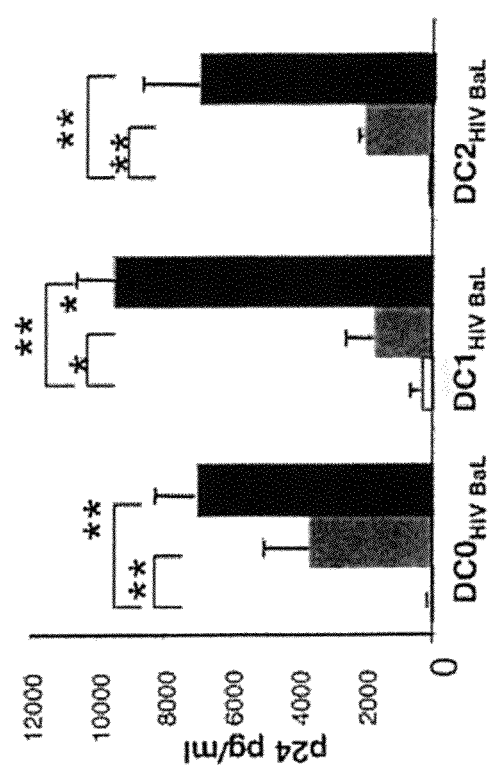
Figure 5G:
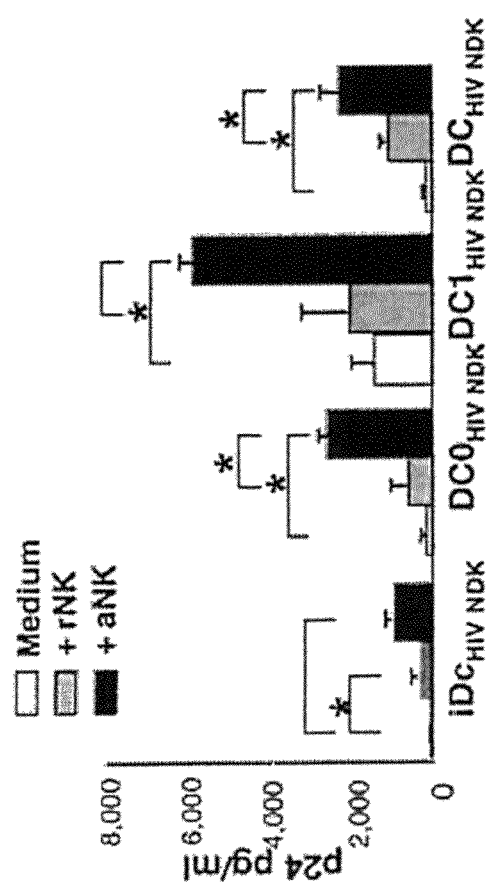

Pivotal Role of HMGB1 in NK-DC Dependent Triggering of HIV-1 Replication and Persistence in iDCs Since it was shown that the impairment of Th1 polarization by NK-sensitized HIV-1 infected DCs was dependent on HIV-1 replication (FIG. 4d), the inventors tested whether aNK-iDC interaction could trigger HIV-1 replication in iDCs. iDCs were infected for 3 h with HIV-1 (1 ng/ml of p24) and further cultured either alone or in the presence of rNK or aNK for 18 h, and the frequency of DCs with intracellular expression of p24 was determined by flow cytometry. While the percentage of p24$^+$ DCs was quite low when infected iDCs were cultured alone, it significantly increased following their interaction with aNK cells, the p24$^+$ DCs representing almost one third of all DCs as compared to only 4% in the absence of NK cells (FIG. 5a). Under the same conditions, rNK cells had no effect on HIV replication in iDCs (FIG. 5a). aNK-dependent increased HIV replication in infected DCs was confirmed by p24 antigen detection in culture supernatants, and a statistically significant increase of p24 production was detected in cocultures of aNK with HIV-1-iDC as compared to infected iDCs cultured alone or with rNK cells (FIG. 5b). The dramatic effect of NK-DC interaction on the frequency of p24-expressing DCs was confirmed by confocal microscopy with p24-specific antibodies. While very rare DCs were stained for intracellular p24 on the day following their infection, a high number of p24$^+$ DC were observed after their culture with aNK cells (FIG. 5c). Interestingly, the positive influence of aNK cells on HIV replication in iDCs was similarly observed on mature DCs. An increased frequency of p24$^+$ DCs, detected by FACS, was found in HIV-1-infected DC0 cocultured during 24 h with aNK cells as compared to DC0 cultured alone (FIG. 5d), and p24 detection in culture supernatants from HIV-1-infected mature DC0, DC1 and DC2, cocultured with aNK cells, confirmed the significant stimulating effect of aNK cells on HIV-1 replication in mature DCs (FIG. 5e). Of note, rNK cells had no significant impact on HIV-1 replication in mature infected-DCs (FIG. 5e). The inventors then tested whether aNK cells had an influence on the expression of proviral DNA in iDCs. Data in FIG. 5(f) show that a very high increase in the number of HIV-1 proviral DNA copies was detected in cultures of infected iDCs with aNK cells, as compared with that of infected iDCs with rNK cells or infected iDCs alone.

Figure 6:
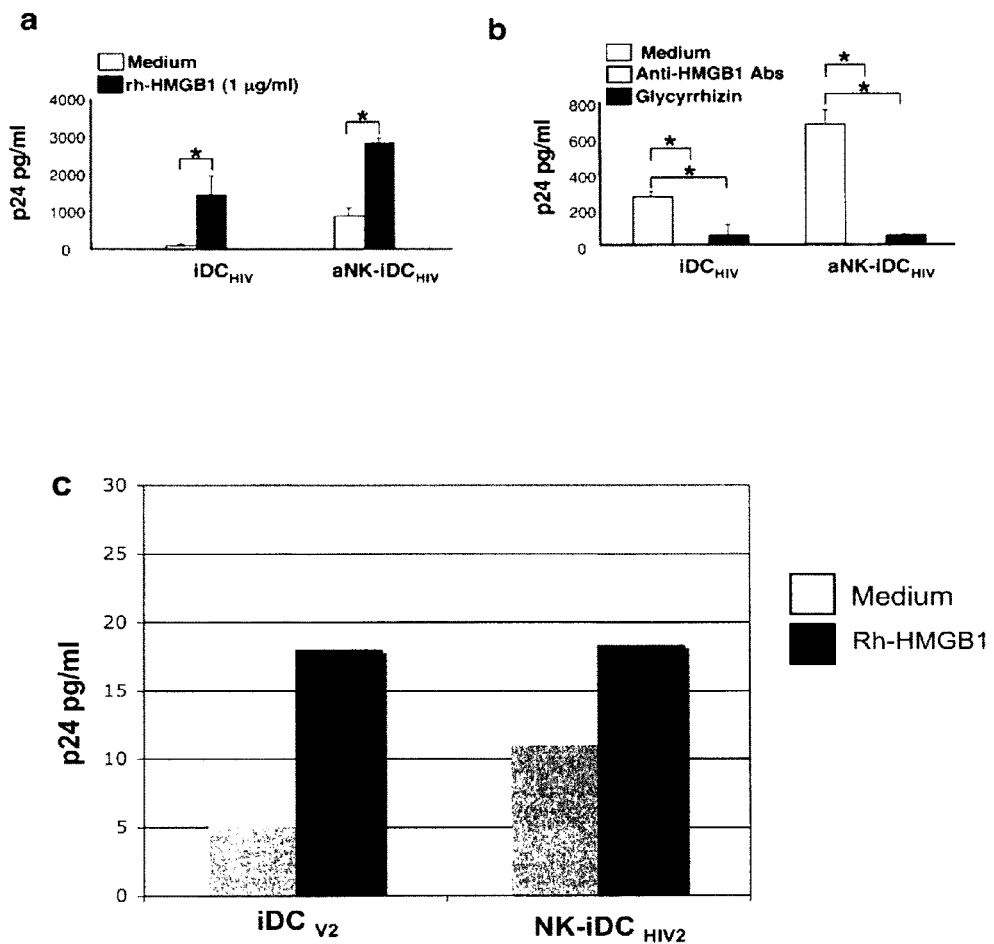
FIGS. 6 (a), (b) and (c). Exogenous rh-HMGB1 triggers HIV-1 and HIV-2 replication in iDC. (a) HIV-1-infected iDC were cultured alone or in the presence of aNK cells for 3 days. Rh-HMGB1 (1 µg/ml) was added in some cultures. HIV replication was measured by p24 quantification in culture supernatant (b) HIV1-infected iDC were cultured alone or in the presence of aNK cells for 3 days. Blocking anti-HMGB1 antibodies (10 µg/ml) or glycyrrhizin (10 µg/ml) were added at culture initiation. HIV replication was measured by p24 quantification in culture supernatant. The mean±sd of three independent experiments is shown. Statistical comparisons were made with the non parametric Mann-Whitney test. * p<0.05; (c) HIV-2-infected iDC were cultured alone or in the presence of aNK cells for 3 days. Rh-HMGB1 (1 µg/ml) was added in some cultures. HIV replication was measured by p24 quantification in culture supernatant.

Exogenous HMGB1 was recently reported to increase HIV-1 replication in infected monocytic cell lines38, and to induce in vitro the reactivation of HIV-1 in PBMCs from HIV-1-infected patients under antiretroviral therapy39. Therefore, the question of the role of HMGB1 in the NK-dependent triggering of HIV replication in DCs was addressed. It was found that exogenous rh-HMGB1 had a direct effect on HIV-1-infected iDC, enhancing dramatically the production of p24 in culture supernatants (FIG. 6a). rh-HMGB1 had also a significant stimulatory effect on p24 production by HIV-1-infected iDC cocultured with a NK cells (FIG. 6a). To investigate the influence of HMGB1 in the triggering of HIV-1 replication in infected-iDC-aNK cocultures, HMGB1-specific neutralizing antibodies or glycyrrhizin were added to these cocultures and p24 production was measured in the supernatant. Both HMGB1 inhibitors abrogated HIV-1 production by infected DC cocultured with aNK cells or cultured alone (FIG. 6b). These results indicate that exogenous HMGB1 is able to trigger HIV-1 replication by infected iDC. They also indicate that aNK cell-dependent stimulation of HIV-1 replication in iDCs is mediated by HMGB1.

Example 6

Isolation and Separation of Primary Cells

Peripheral blood mononuclear cells (PBMCs) were separated from the blood of healthy donors (EFS Cabanel, Paris, France) on a Ficoll-Hypaque density gradient. CD14+ monocytes were isolated from PBMCs by positive selection using CD14-specific immunomagnetic beads (Miltenyi Biotech, Auburn, Calif.). To generate iDCs, purified CD14+ monocytes were cultured for 6 days ($1\times10^6$ cells/ml) in RPMI 1640 medium supplemented with 2 mM glutamine, 10% FCS, penicillin (100 U/ml) and streptomycin (100 μg/ml), in the presence of 10 ng/ml of recombinant human (rhu) GM-CSF and 10 ng/ml rhIL-4☐ (Peprotech INC, Rockyhill, USA) as described[53]. Culture medium was replaced every 2 days. NK cells were isolated by negative selection from PBMCs depleted of monocytes using a depletion cocktail of antibodies directed to CD3, CD4, CD14, CD19, CD20, CD36, CD123, CD66b, Glycophorin A (StemCell Technologies). The NK cell content of the enriched fraction, determined by flow cytometry (FACScalibur, Becton Dickinson) as CD3− CD56+ cells with FITC-conjugated anti-CD3 and APC-conjugated anti-CD56 antibodies, ranged from 85 to 95% in the different experiments. Contamination with myeloid cells, evaluated with FITC-conjugated anti-CD14 antibodies was consistently less than 1%. Naïve CD4 T cells (CD4+ CD45RA+) were isolated from PBMCs by positive selection, using CD4- and CD45RA-specific immunomagnetic beads (Miltenyi Biotech, Auburn, Calif.). Cell purity of isolated naïve CD4 T cells was routinely more than 90%.

Example 7

Activation and Infection of NK Cells

Purified NK cells were cultured at 106 cells/ml either in the presence of suboptimal concentration of IL-2 (100 ng/ml) (Peprotech) to maintain them alive (referred as rNK) or were activated by a combination of PHA (10 μg/ml) (Sigma) and IL-2 (10 μg/ml) (referred as aNK cells). In some experiments, aNK cells (106 cells/ml) were incubated during 3 h in the presence of HIV-1 (1 ng/ml p24) and further cultured for 21 h. Under those conditions, no productive infection could be observed. Culture supernatants were then tested for cytokine and chemokine detection (see below).

Example 8

Maturation and Phenotypic Analysis of Dendritic Cells

After 6 days of culture in the presence of IL-4 and GM-CSF, iDCs (106 cells/ml) were either non stimulated, or stimulated during 48 h with 10 μg/ml LPS (*E. coli* serotype 026-B6, Sigma-Aldrich) to obtain DC0 cells, or 500 ng/ml of trimeric CD40L (Sigma-Aldrich) to obtain DC1 cells, or 10 μg/ml of LPS and 1 μg/ml PGE2 (Sigma-Aldrich) to obtain DC2 cells. Phenotypic analysis of DCs and characterization of their maturation stage was performed by flow cytometry. DCs were stained for 20 min at 4° C. with antibodies specific for CD80, CD83, CD86, HLA-DR, CD40, DC-LAMP or DC-SIGN (all antibodies from BD Biosciences, San Jose, Calif.) diluted in 100 μl of PBS/10% FCS/0.1% NaN3. In some experiments, antibody specific for HMGB1-receptor, RAGE (Abcam), was used to stain DCs. After two washings, cells were fixed in 1% PFA, immediately acquired on a FACScalibur (Becton Dickinson) and analyzed with Flow Jo software.

Example 9

Infection of Dendritic Cells with HIV-1

Virus stock preparation was prepared by amplification of R5-HIV-1Ba-L on MDM from healthy donors. Viral stock was then clarified by centrifugation prior to determination of HIV1 p24 concentration. iDCs were plated in 96-well culture plates at 200,000 cells/well and incubated for 3 hours at 37° C. in a 5% CO2 atmosphere with R5-HIV-1BAL at various concentrations (0.001 to 10 ng p24/ml). Cells were harvested, washed four times with media containing 10% FCS and, when indicated, rNK or aNK cells were added at a NK:DC ratio of 1:5, unless otherwise indicated. NK-DC cocultures lasted 24 h before analysis of the maturation stage of DCs and/or quantification of viral production. In some experiments (FIG. 6), HIV-1 infected iDCs were incubated alone or with aNK cells for 3 days, in the presence of rh-HMGB1 (1 μg/ml) (R&DSystems), and in some cultures in the presence of rabbit antiHMGB1 Abs (10 μg/ml) (Abcam, Cambridge, UK) or Glycyrrhizin (10 μg/ml).

Example 10

Quantification of HIV-1 Viral Production, Proviral Load and of the Frequency of Infected DCs The concentration of HIV-1 in the supernatant of infected cell cultures was determined by measuring the amount of p24 protein by ELISA (Ingen, Belgium). DNA from cells was extracted using the GIAamp DNA Blood Mini Kit (Qiagen, Basel, Switzerland) and quantified HIV-1 proviral load by RT-PCR as described previously[54]. The frequency of HIV-1-infected cells was determined by flow cytometry to detect intracellular p24 molecule. Cells were surface stained with antibodies specific for CD40 (BD Biosciences, San Jose, Calif.) to target DC and intracellular stained with p24-specific antibodies (Coulter). Stained cells were fixed in 1% PFA, immediately acquired on a FACScalibur (Becton Dickinson) and analyzed with FlowJo software. In some experiments infected DCs were imaged, after immunofluorescence, by laser scanning confocal microscopy.

Example 11

Cocultures of iDCs with NK Cells rNK or aNK were cocultured during 24 h with iDCs or mDCs at a ratio of 1:5 ($2\times105$ NK+$10\times105$ DC/1 ml), unless otherwise indicated. DC survival was determined with the 7-AAD assay, as described previously[55]. Briefly, cultured cells were stained with 20 μg/mL nuclear dye 7-amino-actinomycin D (7-AAD; St. Quentin-Fallavier, Sigma-Aldrich) for 30 minutes at 4° C., and co-stained with CD56-specific antibody (BD Biosciences, San Jose, Calif.). Surviving DC were identified as CD56-7-AAD− cells. When phenotypic characterization of DCs was performed in NK-DC cocultures, NK cells were always excluded from the FACS analysis through their staining with CD56-specific antibodies.

Example 12

Measurement of Cytokine and Chemokine Production

Cell-free culture supernatants were prepared by incubating for 24 h iDCs at $10^6$ cells/ml, rNK or aNK cells at $2\cdot10^5$ cells/ml or aNK and iDC cells at the ration of 1:5. Chemokines and cytokines were measured by Luminex (24 plex kits; Biosource) following the manufacturer's instructions. In brief, 50 μl of supernatant or standard was incubated with antibody-linked beads for 2 h, washed twice with wash solution, and incubated for 1 h with biotinylated secondary antibodies. A final incubation of 30 min with streptavidin-PE preceded the acquisition on the Luminex 100IS. At least 100 events were acquired for each analyte. Values above or below the standard curves were replaced by the lowest or the highest concentrations measured. Quantification of HMGB1 in cell free culture supernatants was performed with an ELISA kit (IBL, Hamburg). In experiments testing Th1 polarization of naïve CD4 T cells by NK-triggered DCs (FIG. 4), quantification of IL-12, IFN-γ and IL-18 in culture supernatants was performed with ELISA kits (IL-12 and IFN-γ kits from R&D Systems, IL-18 kit from MBL).

Example 13

Th1 Polarization Assay

Naïve CD4 T cells (106/ml) were cocultured for 8 days in the presence of uninfected or HIV-1-infected iDC (106/ml) and resting or activated NK cells (2×105/ml) and tested for Th1 polarization by flow cytometry, as previously reported 56. Briefly, brefeldine A (10 μg/ml) (Sigma Aldrich) was added during the last 16 h of the culture to inhibit protein secretion. Surface staining was performed with PerCP-conjugated CD8 antibodies and FITC-conjugated CD3 antibodies (BD Biosciences, San Jose, Calif.), followed by cell fixation for 15 minutes at 4° C. with 1% PFA and permeabilization with saponin buffer (PBS-BSA 0.2%-NaN3 0.01%-saponin 0.5%), and intracellular staining was performed with APC-conjugated IFNγ- or IL-4-specific antibodies (BD Biosciences, San Jose, Calif.). Stained cells were immediately acquired on a FACScalibur (Becton Dickinson) and analyzed with Flow Jo software. In order to analyze the influence of HIV-1 replication on Th1 polarization, AZT 1 mM was added at the initiation of the culture of naïve CD4 T cells incubated alone, or in the presence of HIV-1 infected iDCs+/−rNK or aNK cells. AZT was left until the end of the coculture. HIV-1-infection of iDCs was performed as described above, in the absence of AZT.

Example 14

Statistical Analysis

Statistical analyses were made with the non parametric Mann-Whitney test. The P value of significant differences is reported. Plotted data represent mean±standard deviation (s.d.).

Example 15

HIV-1-Infected Dendritic Cells are Resistant to NK-Induced Apoptosis Through an hmgb1-Dependent Mechanism Dendritic cells (DCs) and natural killer (NK) cells are key innate effectors playing a critical role in early defenses against infections. Evidence of an NK-DC crosstalk has emerged recently. This crosstalk is bidirectional and it may lead to both NK cell activation and differentiation into killer cells, DC maturation or apoptosis, depending on the activation state of both cell types. DCs are required for the priming of helper CD4$^+$ T cells into Th1 effectors, and the chronic expression of uncontrolled viruses, such as HIV, may induce impaired maturation and destruction of DCs. In this study, we addressed the question of the impact of NK-DC interaction on the destruction of DCs, and the influence of HIV on this crosstalk.

Immature DCs (iDCs) were prepared from sorted monocytes from healthy donors, cultured for 6 days in the presence of IL-4 and GM-CSF. In some experiments, iDCs were infected with R5-HIV-1 (1 ng/ml of p24). Coculture experiments with autologous purified aNK cells (activated by PHA+IL-2) were performed at various NK:DC ratios. The influence of NK-DC interaction on DC's maturation and apoptosis was analyzed using multiparametric flow cytometry, combining 7-AAD staining with membrane and intracellular staining with mAbs specific for HLA-DR, DC-SIGN, CD83, CD86, DR4, mTRAIL, etc.

Figure 7A:
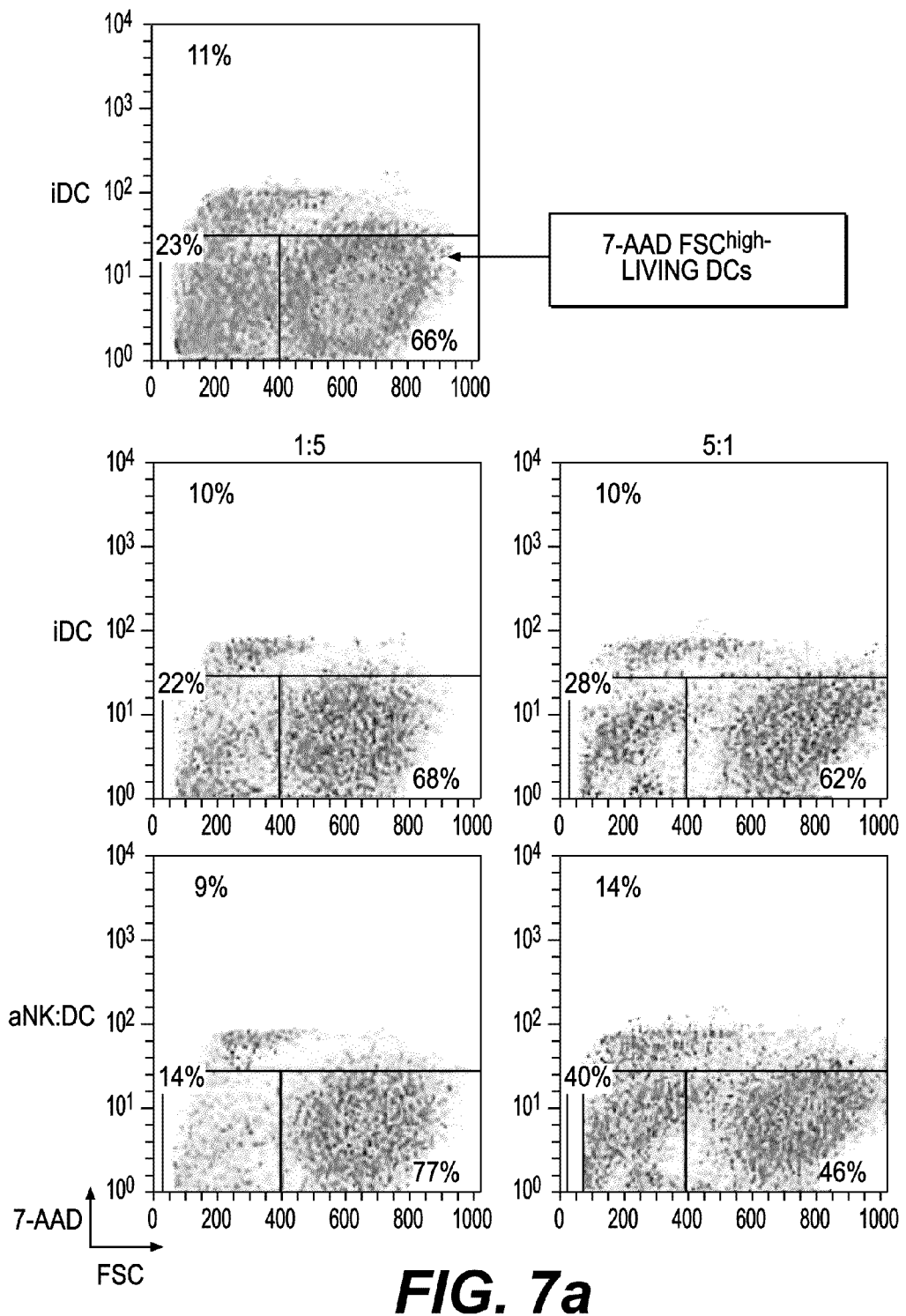
FIGS. 7 (a)-(c). Activated NK cells (aNK) rapidly induce apoptosis of immature dendritic cells (iDCs) at NK:DC ratio of 5:1. (a) iDCs, generated from purified CD14⁺ monocytes from healthy donors in the presence of IL-4 and GM-CSF, were cocultured during 24 h with resting NK cells (rNK) or aNK cells at two different NK:DC ratios (1:5 and 5:1). DCs survival was determined by flow cytometry using the 7-AAD assay. NK cells were excluded from the analysis by gating the CD56⁻ population. Surviving DCs are 7-AAD⁻ FSC$^{high}$ cells. Data represent three independent experiments. (b) Live video microscopy of apoptosis of iDCs induced by aNK cells. Pictures from one representative experiment out of three conducted with different primary cell preparations are shown. (c) Kinetics of iDCs killing by aNK cells, assessed by the proportion of surviving DCs in cocultures. These experiments have been performed on primary cells from a number of healthy donors, and representative data from three of them are shown.
Figure 7B:
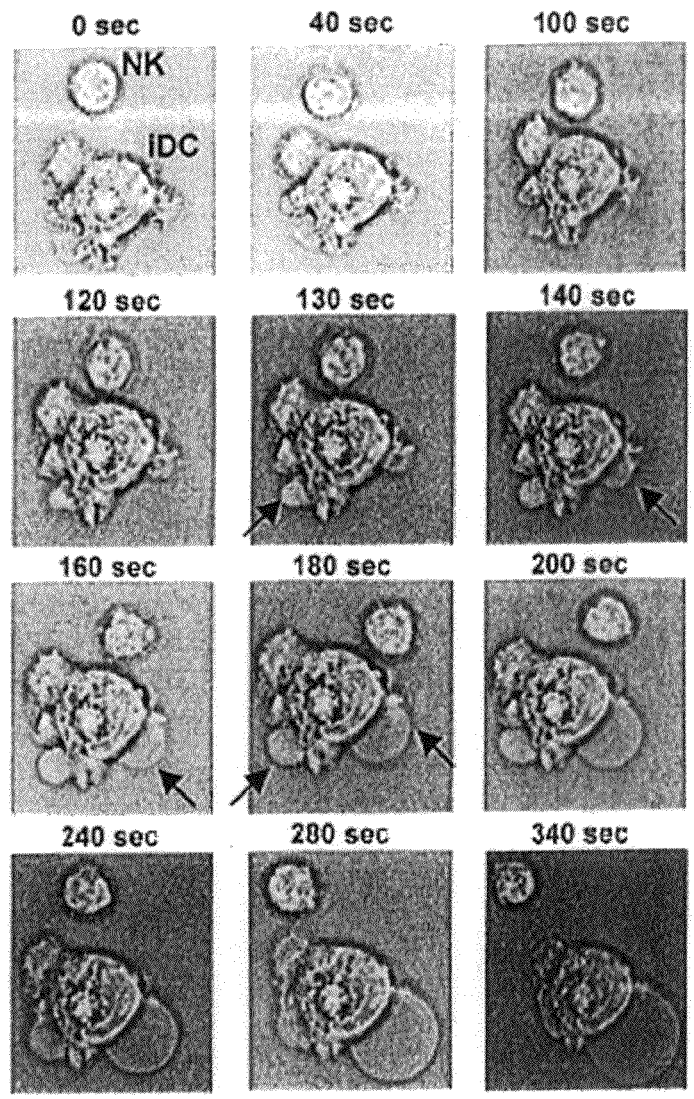
Figure 7C:
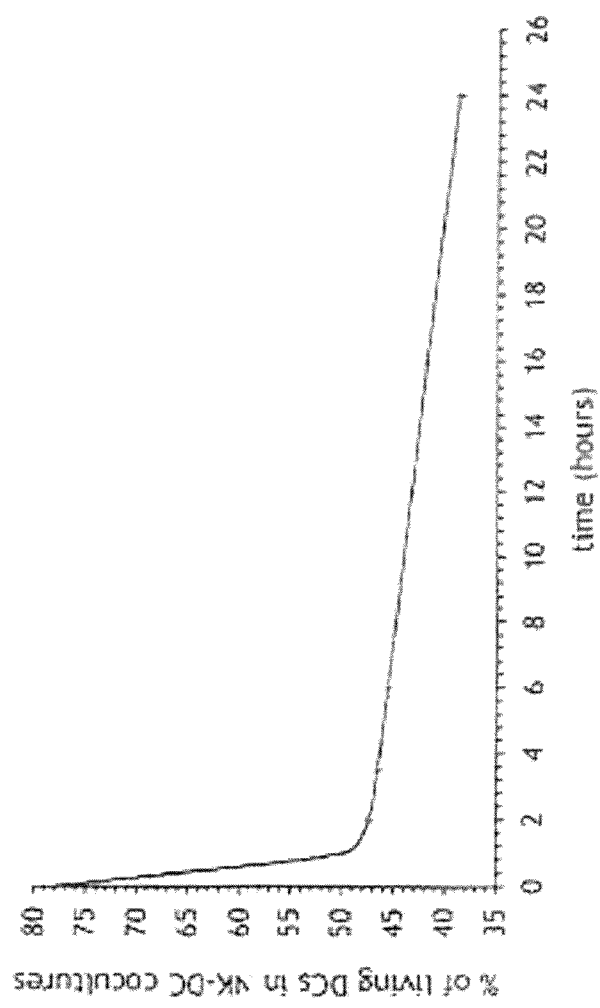
Figure 8A:
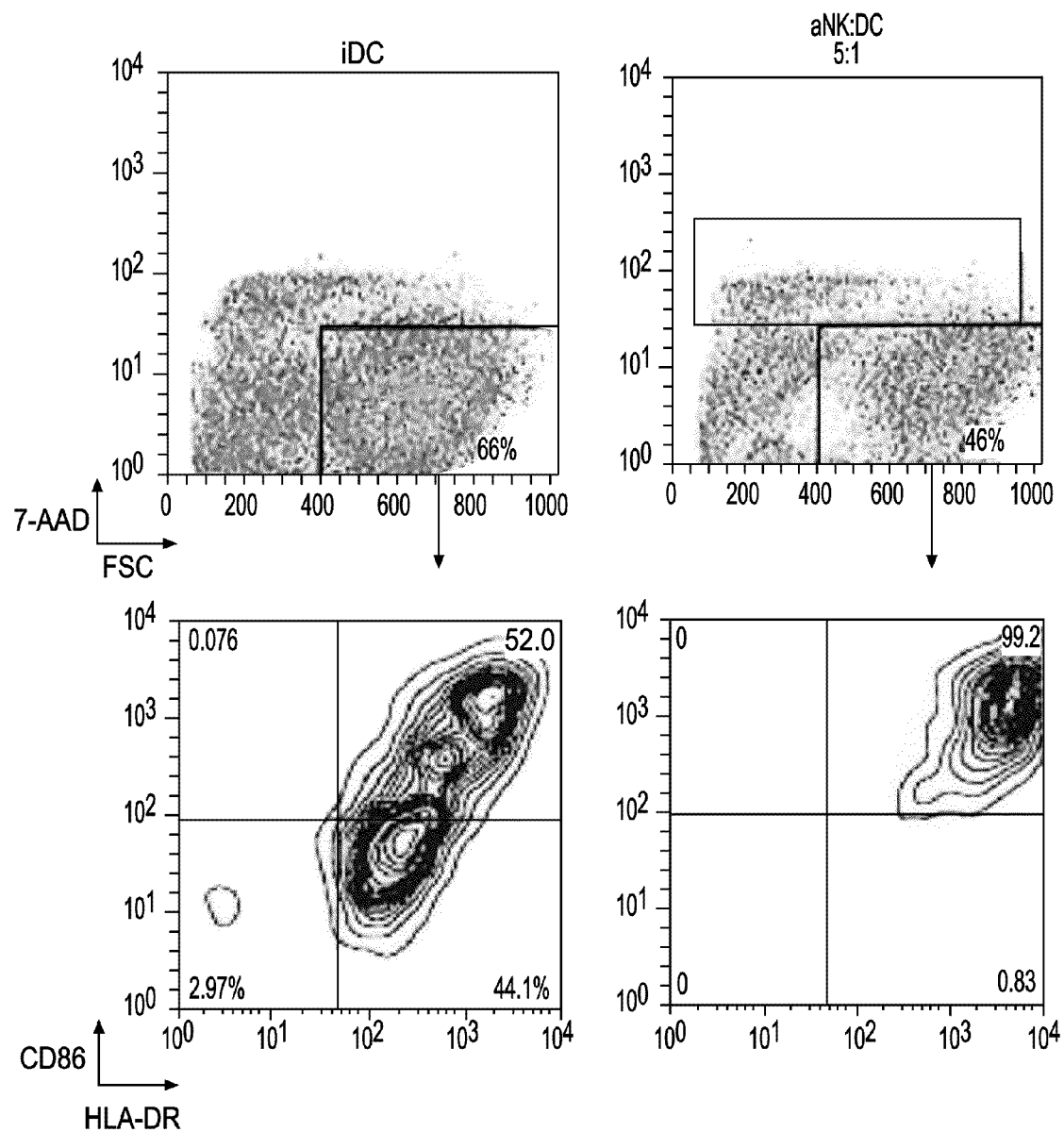
FIGS. 8(a)-(b). DCs that are resistant to killing by aNK cells exhibit a mature phenotype. (a) iDCs, generated from purified CD14⁺ monocytes in the presence of IL-4 and GM-CSF, were cocultured during 24 h with aNK cells at the NK:DC ratio of 5:1. DCs survival was determined by flow cytometry with the 7-AAD assay. NK cells were excluded from the analysis by gating the CD56⁻ population. Surviving DCs are 7-AAD⁻ FSC$^{high}$ cells. In addition to apoptosis, aNK cells induced the maturation of iDCs. Co-staining with HLA-DR and CD86 specific antibodies allowed the identification of mature DCs (CD86$^{bright}$ HLA-DR$^{bright}$) As a positive control, mature DCs were generated by 48 h stimulation of iDCs with LPS (DC0). Data from a representative experiment out of three independent experiments are shown. (b) iDCs cultured alone or cocultured with aNK cells at the NK:DC ratio of 5:1 were stained with anti-CD83 and -DC-SIGN antibodies and analyzed by flow cytometry. The positive expression of both markers demonstrates the mature phenotype of iDCs. Data represent one of three independent experiments.
Figure 8B:
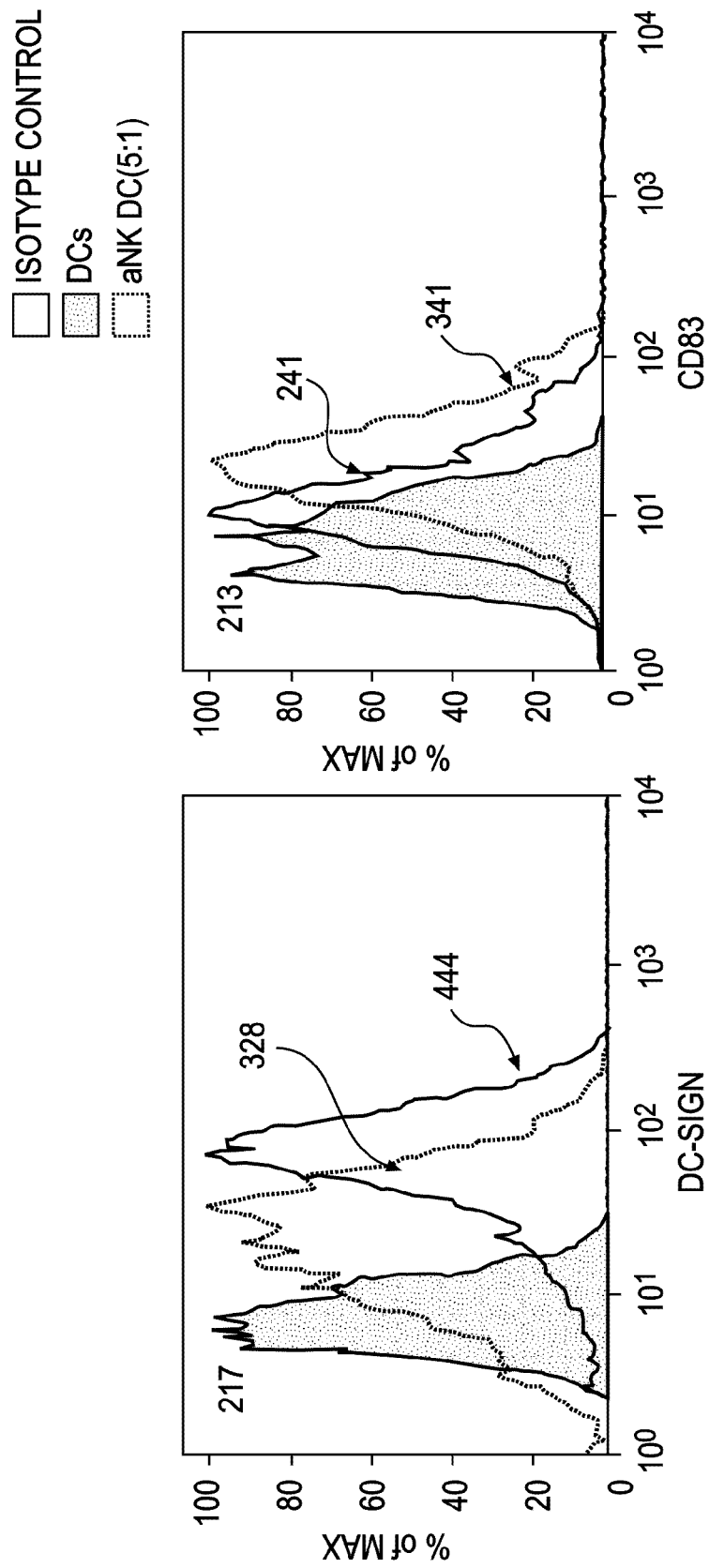
Figure 9A:
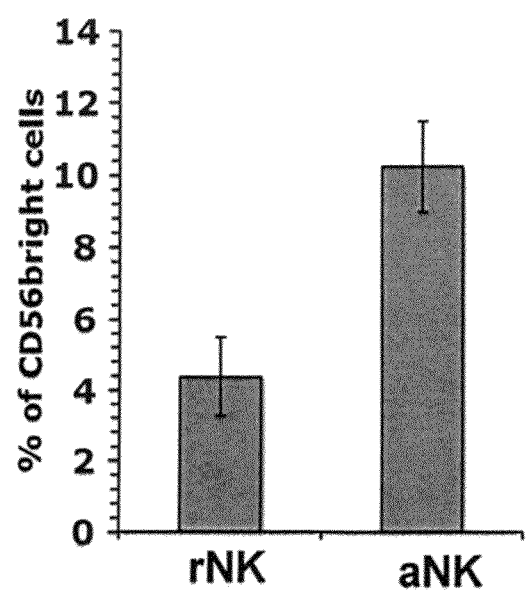
FIGS. 9(a)-(g). aNK-dependent apoptosis of iDCs is TNF-related apoptosis-inducing ligand (TRAIL)-dependent and involves the DR4 receptor. (a) CD56⁺ NK cells were purified from the blood of healthy donors. NK cells were maintained in culture with suboptimal concentrations of interleukin-2 (IL-2) (100 ng/ml) (rNK cells) or activated (aNK cells) by the addition PHA (10 µg/ml) and IL-2 (10 µg/ml) to cultures. The intensity of staining with anti-CD56 antibodies allows the distinction between two NK cell populations expressing CD56 highly (CD56$^{bright}$ cells) and weakly (CD56$^{dim}$ cells). Data represent the mean±sd of three independent experiments. (b) Membrane TRAIL (mTRAIL) expression by NK cells is determined by flow cytometry with anti-CD56 and -mTRAIL specific antibodies. Data represent one of three independent experiments. (c) aNK cells were co-stained with anti-CD56 and -mTRAIL antibodies. The proportions of mTRAIL-expressing aNK cells among CD56$^{bright}$ and CD56$^{dim}$ populations were determined. Data represent the mean±sd of three independent experiments. (d) Detection of TRAIL receptor DR4 expression on the surface iDCs by flow cytometry. In some cases, iDCs were cocultured with aNK cells at the NK:DC ratio of 5:1. DR4 expression at the DCs surface is analyzed after 1, 2, 3.5, 6 and 24 h of NK-DC coculture. These experiments have been performed on three donors, and representative data from one of them are shown. (e) iDCs ($10^6$ cells/ml) were cultured for 24 h with increasing concentrations (1-1000 ng/ml) of recombinant human soluble TRAIL (rhs-TRAIL). Cell death was then quantified with the 7-AAD assay. Data represent the mean±sd of three independent experiments. (f) 24 h cell-free culture supernatants of iDCs, rNK cells, aNK cells ($10^6$/ml), or cocultures of aNK cells and iDCs (ratio 5:1) were tested for soluble TRAIL (sTRAIL) content. sTRAIL was quantified by ELISA. Data represent the mean±sd of three independent experiments. (g) iDCs were cultured for 24 h either alone or with aNK cells (NK:DC ratio of 5:1), in the absence or presence of blocking anti-DR4 antibodies (250 ng/ml). The viability status of DCs was determined by flow cytometry with the 7-AAD assay. Data represent one of three independent experiments.
Figure 9B:
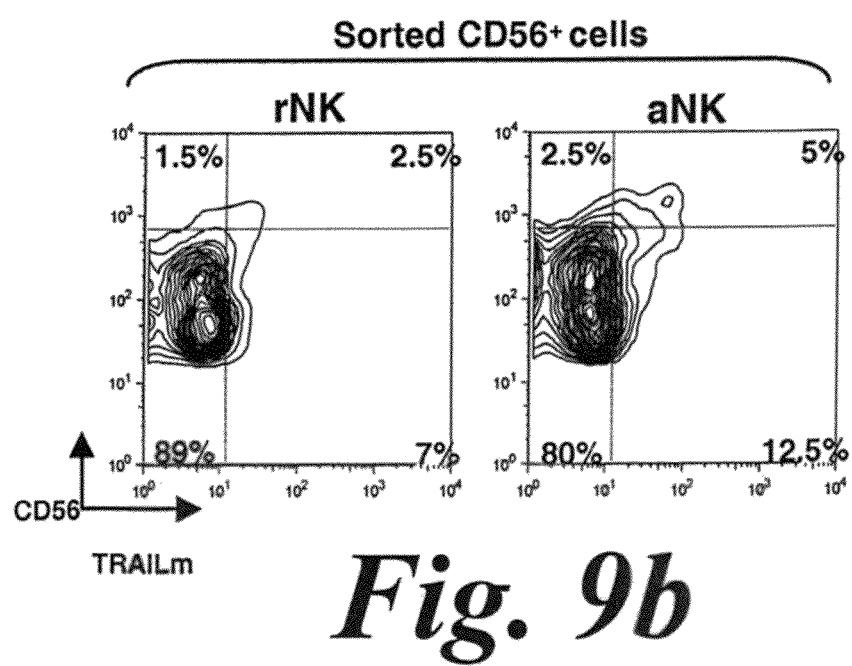
Figure 9C:
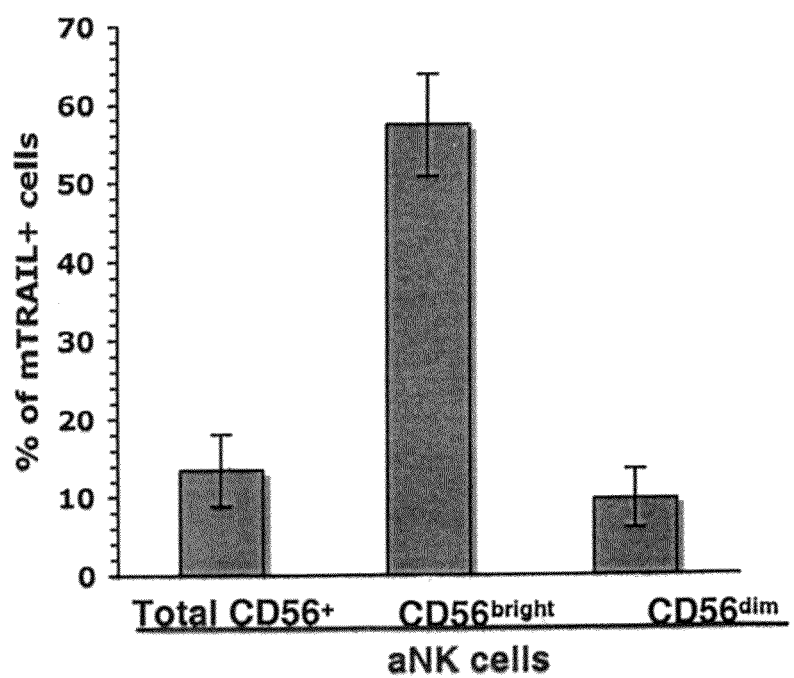
Figure 9D:
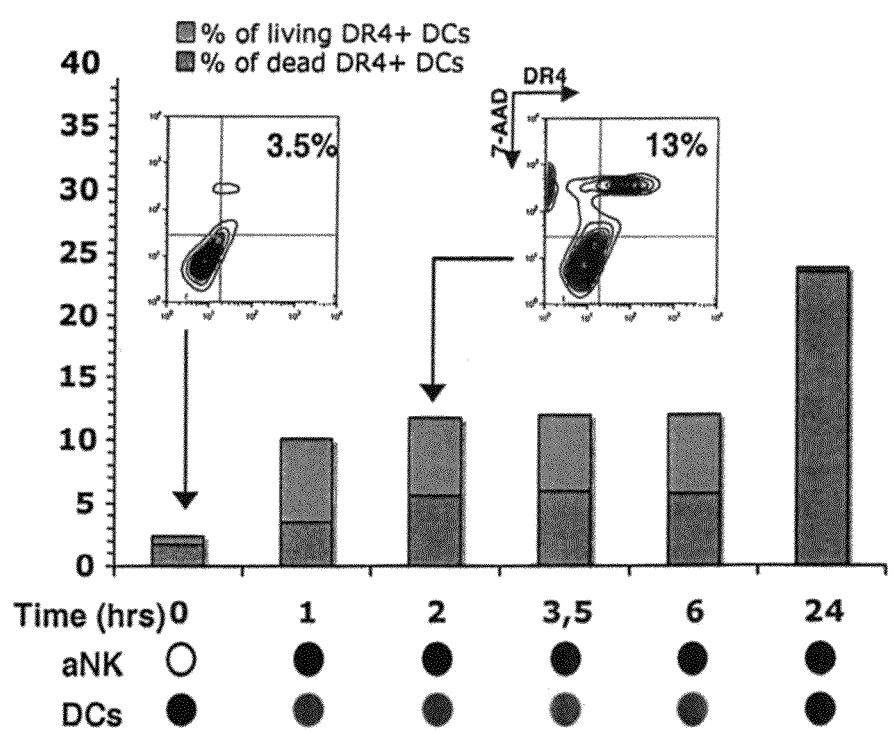
Figure 9E:
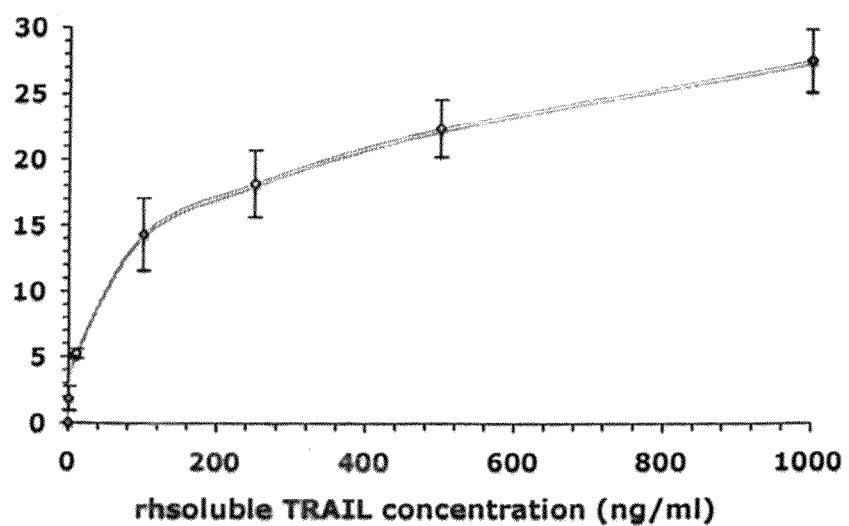
Figure 9F:
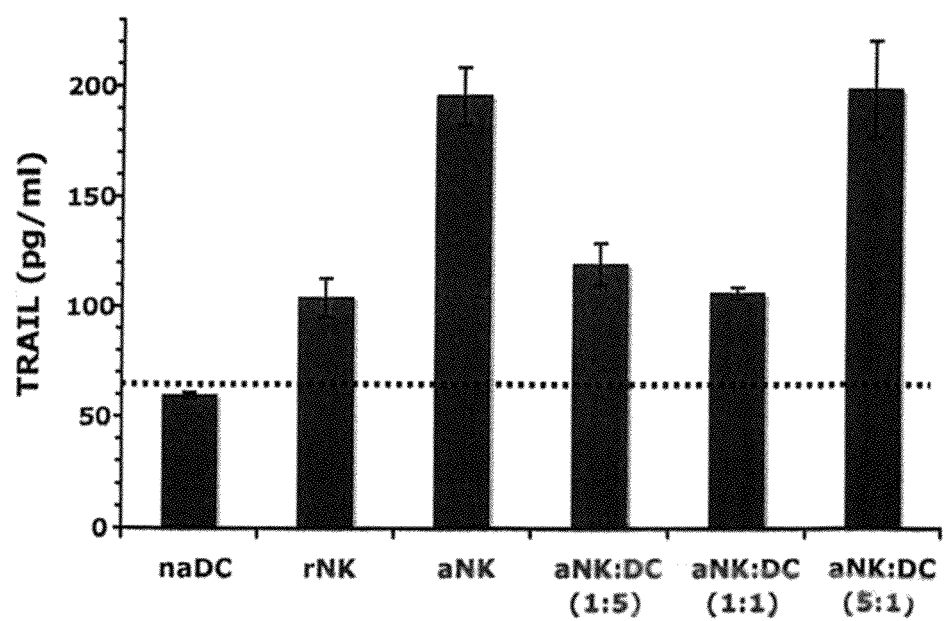
Figure 9G:
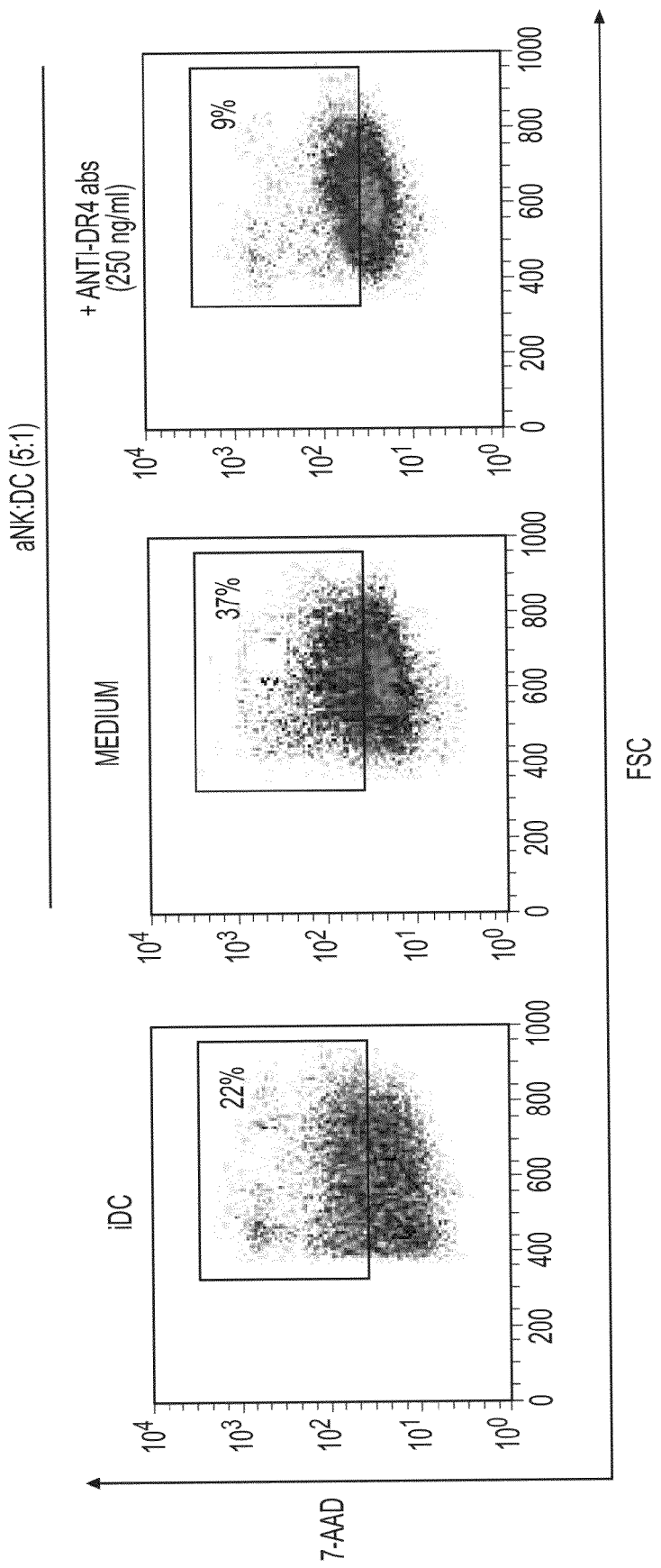
Figure 10A:
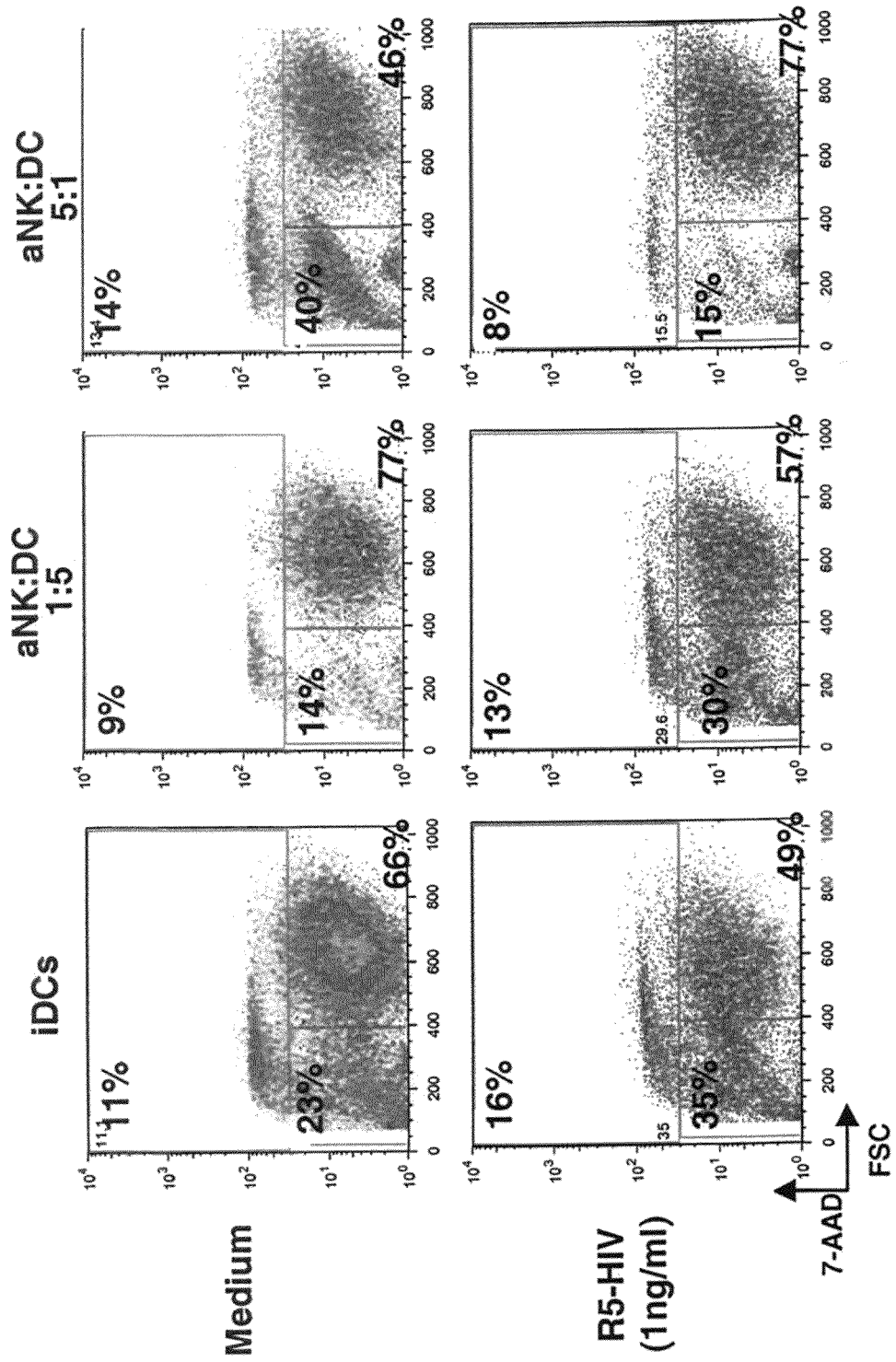
FIGS. 10(a)-(d). R5-HIV-infected DCs are resistant to killing by aNK cells, although TRAIL secretion persists in the presence of HIV-1 (a) iDCs were either infected with R5-HIV-1$_{BaL}$ (1 ng/ml of p24) for 24 h or uninfected, and after several washes, they were incubated with aNK cells at the ratios of 1:5 and 5:1. iDCs viability was assayed with the 7-AAD test by flow cytometry. Living cells are 7-AAA$^-$, apoptotic cells 7-AAD$^+$, and apoptotic debris are 7-AAD$^-$ FSC$^{low}$. Dot plots represent one of at least three independent experiments. (b) R5-HIV does not induce iDC maturation. DCs were uninfected (iDCs), infected with R5-HIV-1 at 1 ng/ml of p24 (HIV-DCs) or stimulated with LPS for 48 h. Cells were then stained with CD86 and HLA-DR. Data represent one of at least three independent experiments. (c) TRAIL secretion is not affected by HIV infection of iDCs. 24 h cell-free culture supernatants of iDCs, HIV-infected DCs ($10^6$/ml), aNK cells-iDCs cocultures (ratio 5:1) and aNK cells-HIV-infected DCs cocultures (ratio 5:1) were tested for soluble TRAIL (sTRAIL) content by ELISA. Data represent the mean±sd of three independent experiments. (d) HIV-1-infected DCs are still susceptible to TRAIL-induced apoptosis. iDCs and HIV-infected DCs ($10^6$ cells/ml) were cultured for 24 h with increasing concentrations (1-1000 ng/ml) of rhs-TRAIL. Cell death was then quantified with the 7-AAD assay. The mean±sd of three independent experiments was presented.
Figure 10B:
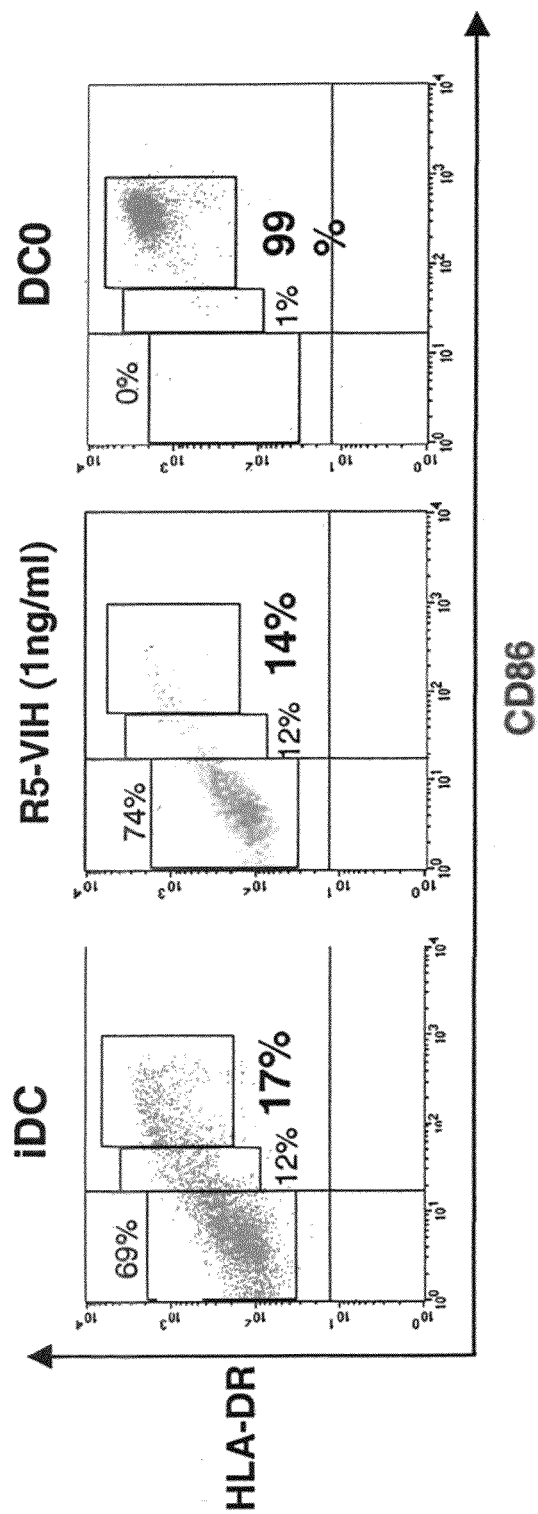
Figure 10C:
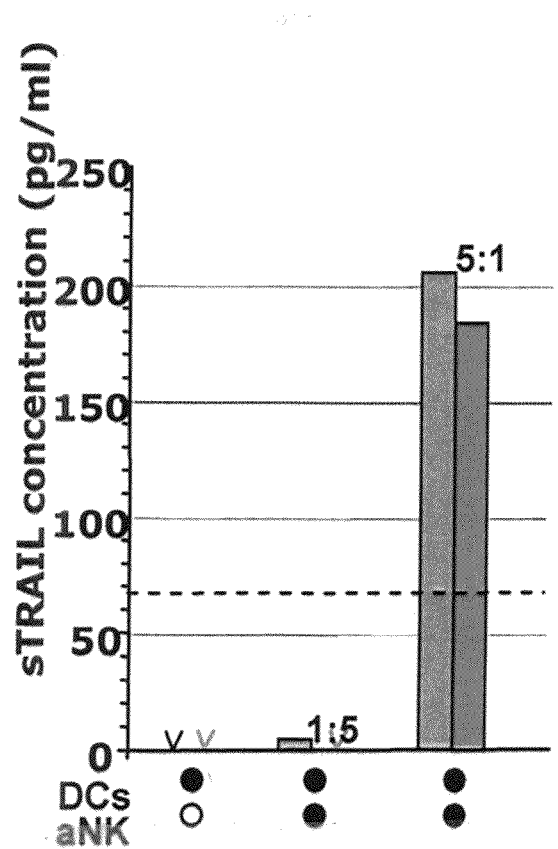
Figure 10D:
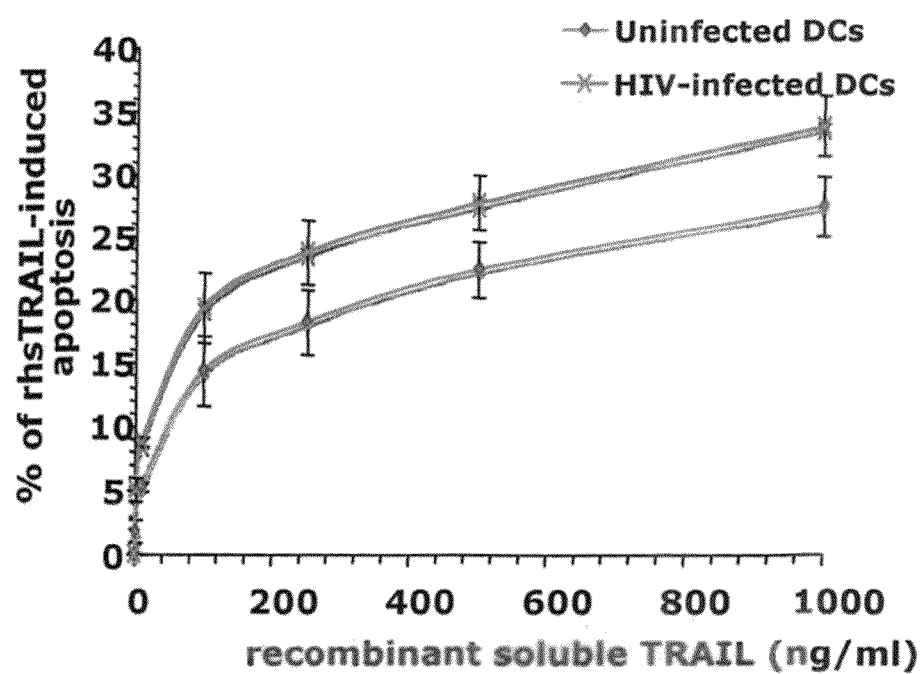

It was found that aNK cells rapidly (within 1-2 h) induce apoptosis of uninfected iDCs at the NK:DC ratio of 5:1. Live videomicroscopy of NK-DC cocultures confirmed that directly after an NK-DC contact, DCs show a typical apoptotic phenotype (increase in cell's volume and bubbling) (FIG. 7). Surviving DCs exhibit the phenotype of mature cells (FIG. 8). iDC apoptosis involves TNF-related apoptosis induced ligand (TRAIL) produced by aNK cells, and it is mediated by the interaction between CD56$^{bright}$ NK cells expressing TRAIL at their membrane level and DCs expressing the TRAIL's receptor DR4. NK-dependent iDCs apoptosis is completely abrogated by neutralizing anti-DR4 antibodies, highlighting the important role of the TRAIL-dependent pathway in this process (FIG. 9). However, the addition of Concanamycin A (an inhibitor of granules' dependant cytotoxicity) to NK-DC cocultures has no effect on NK-dependent DCs apoptosis, excluding the implication of the perforin pathway in DC apoptosis.

Figure 11A:
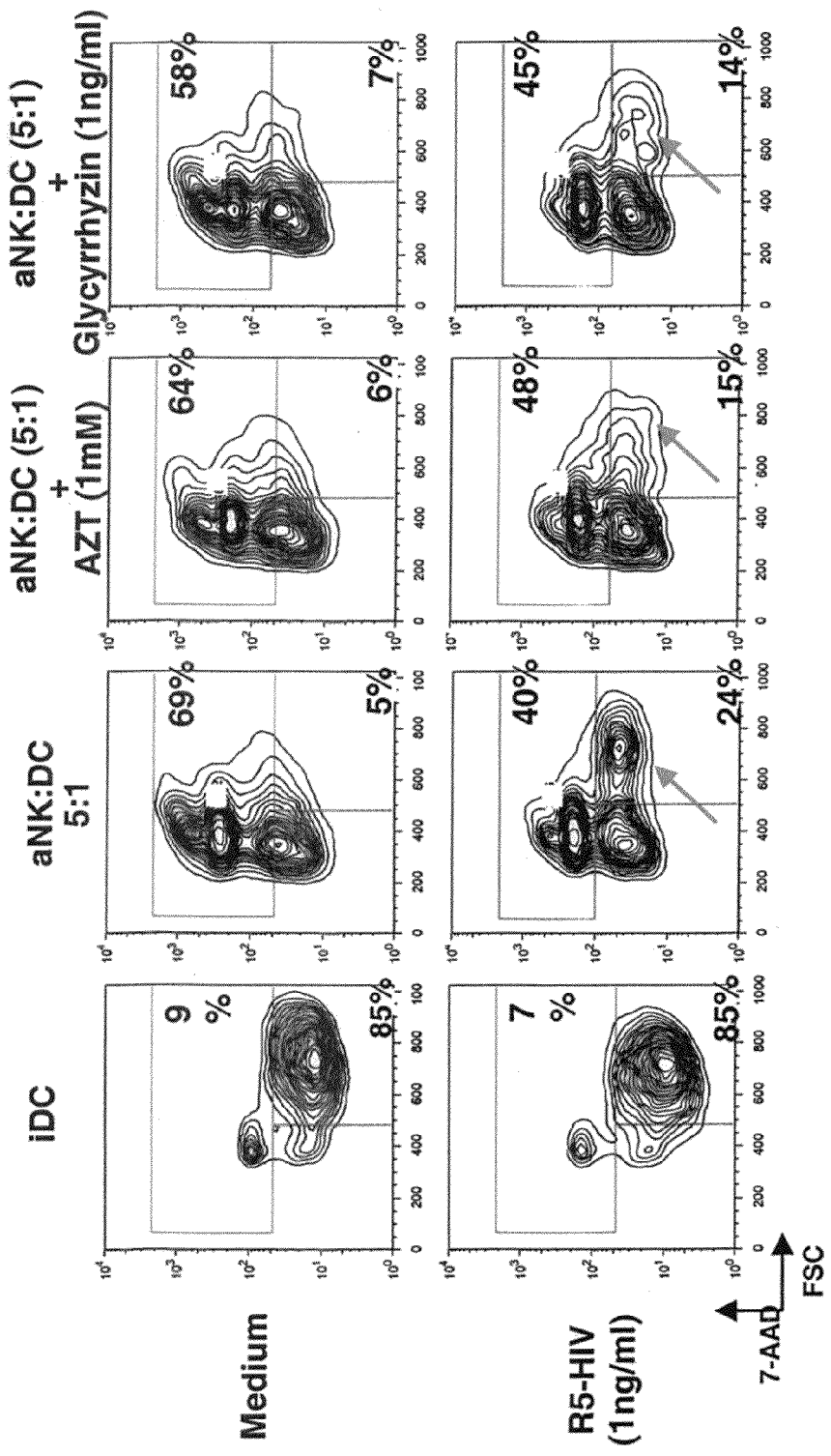
FIGS. 11(a)-(b). High-mobility group box 1 (HMGB1) is involved in resistance of HIV-1-infected iDCs to NK-induced DC apoptosis. (a) iDCs or HIV-1-infected iDCs were cultured alone or in the presence of aNK cells (NK:DC ratio of 5:1). In some experiments, azidothymidine (AZT) was added at the time of HIV infection; in others glycyrrhizin (10 ng/ml) was added at coculture initiation. Cell death was then quantified with the 7-AAD assay. (b) Same experiments were performed in the presence of blocking anti-HMGB1 antibodies (10 and 15 µg/ml). One representative experiment out of three conducted is shown.
Figure 11B:
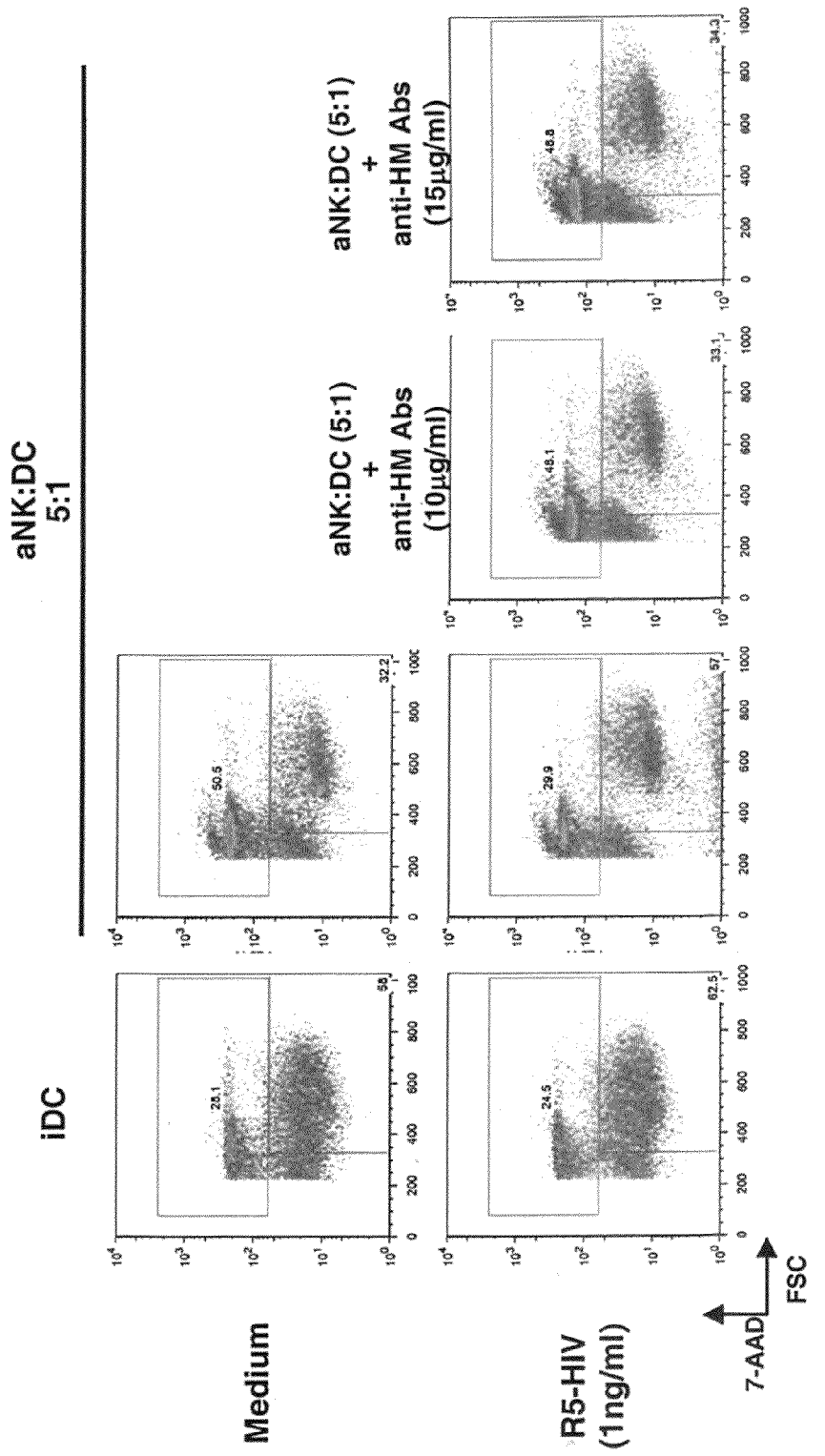

To investigate the impact of HIV on aNK-induced iDCs' apoptosis, iDCs were infected with R5-HIV-1 (1 ng of p24/ml). Following HIV infection, iDCs became resistant to aNK-dependent apoptosis. HIV-1 did not induce by itself the maturation of iDCs, as shown by CD86/HLA-DR co-staining of infected iDCs (FIG. 10). TRAIL secretion by aNK cells was not affected by HIV infection of iDCs, and HIV-1-infected DCs were still susceptible to TRAIL-induced apoptosis (FIG. 10). Resistance of HIV-1-infected iDCs to aNK-induced apoptosis was found dependent on HMGB1, as shown by inhibition assays in the presence of glycyrrhizin or blocking anti-HMGB1 antibodies (FIG. 11). Resistance of HIV-1-infected iDCs to aNK-induced apoptosis was also found dependent on HIV-1 replication in DCs, as demonstrated by the addition of azidothymidine (AZT) at the time of iDC infection (FIG. 11). Altogether, these results show that HIV-1 infection of iDCs induces resistance of infected iDCs to aNK-induced apoptosis, involving the proinflammatory cytokine HMGB1.

The inventors previously recognized that the cross-talk between aNK cells and HIV-1-infected iDCs resulted in a dramatic increase in viral replication and proviral DNA expression in DCs, and this process was mainly triggered by HMGB1. The results in this Example show the critical involvement of HMGB1 as a key mediator in the survival of HIV-1 infected-DCs, highlighting then the role of HMGB1 in viral persistence and establishment of HIV reservoirs. These results show how HIV 'hijacks' DCs to promote efficiently viral dissemination and how this property can be used to treat HIV infection.

Example 16 aNK-DC Cocultures Experiments in the Presence of HIV-2

The question of the susceptibility of HIV-2-infected DCs on NK-dependent triggering of viral replication was addressed, similarly to HIV-1. The influence of HMGB1 in that process was evaluated.

1—Infection of DCs with HIV-2: iDCs were plated in 96-well culture plates at 500,000 cells/well and incubated for 3 hours at 37° C. in a 5% CO2 atmosphere with HIV-2 (20 ng p24/ml).

2—NK-DC cocultures: cells were harvested, washed three times with RPMI containing 10% FCS and, when indicated, aNK cells were added at a NK:DC ratio of 1:5. When indicated, recombinant HMGB1 was added at 10 µg/ml (R&D Systems), or rabbit anti-HMGB1 Abs (1 µg/ml) (Abcam, Cambridge, UK). NK-DC cocultures lasted 3 to 7 days before quantification of viral production in culture supernatants.

3—Quantification of HIV-2 viral production: the concentration of HIV-2 particles in the supernatants was determined with the p24 ELISA kit (Ingen, Belgium).

As shown on FIG. 6C, a very low level of HIV-2 production was detected after three days of infection, whether infected DCs were cultured alone or in the presence of aNK cells. rh-HMGB1 induced a slight increase in viral replication. As observed in our previous studies with HIV-1, day 3 of infection of DCS is too early to detect significant viral replication. These coculture supernatants will be tested again at day 7.

Example 17

Detection of HMGB1 Protein and Anti-HMGB1 Antibodies in Human Sera/Association with Disease Activity in Patients Infected with HIV The concentration of HMGB1 protein in sera from HIV-infected patients was quantitated, according to the ELISA kit Shino Test (IBL).

Moreover, a specific Elisa assay for the detection of total anti-HMGB1-specific antibodies was develop. Considering that autoantibodies specific for HMGB1 can be found in SLE (Systemic lupus erythematosus) (Hayashi et al., 2009), it was asked whether anti-HMGB1 antibodies were detected in HIV-infected patients and if their levels were correlated with HIV infection.

ELISA Assay for the Detection of Anti-HMGB1 Antibodies

The assay was developed in two steps:

(1) In a first step, rabbit polyclonal antibodies specific for human HMGB1 were used, to define the conditions for titration of antibodies on coated HMGB1 or BOX B. Since anti-HMGB1 antibodies were suspected to be found as immune complexes, in serums (Urbonaviciute et al. *Factors masking HMGB1 in human serum and plasma. J Leukoc Biol.* 2007 81:67-74), a method to dissociate these complexes before titration of antibodies was develop.

(2) In a second step, human samples from several groups of donors (sera from either healthy donors, septic choc patients or HIV+ patients before and after antiretroviral treatment) were used.

The following Reagents were used:

Rabbit primary polyclonal antibodies to human HMGB1 (Adcam ab18256) are directed against a KLH-conjugated synthetic peptide derived from residues 150 to C-terminus of human HMGB1.

Recombinant HMGB1 (HMGBiotech, HM-115) produced in *E. Coli* from an expression plasmid coding for rat HMGB1, 99% identical to the human HMGB1.

Recombinant BOXB from HMGB1 (HMGBiotech HM-051) produced in *E. Coli* from an expression plasmid coding for the mammalian sequence, which is totally identical in human and mouse.

Control rabbit serum (Sigma; Ref: R9133)

anti-rabbit IgG or IgM conjugated to phosphatase alkaline (PAL), substrate p-nitrophenyl phosphate tablets (pNPP), calibrators: human IgG from serum (Sigma; ref 12511) and Human IgM from serum (Sigma; ref 18260)

Anti-human IgG (Fc specific)-alkaline phosphatase antibody produced in goat (Sigma; Ref A9544), anti-human IgM (µ-chain specific)-alkaline phosphatase antibody produced in goat (Sigma; ref A3437)

The following assay was carried out:

Coating of 96-well plates was performed overnight at 4° C. with either 3 µg/ml of HMGB1 or 0.5 µg/ml of BOXB in DPBS. Simultaneously, coating of the calibrator was performed with serial dilutions in DPBS of corresponding isotypes (only for ELISA assay carried out with human samples). Plates were washed four times with DPBS/0.05% (v/v) Tween® 20, using a microplate washer (Atlantis; Oasys). Similar washings were performed after each step of the ELISA assay. Unbound sites were blocked at 4° C. for 2 hours with PBS/2% (w/v) BSA. 100 µl aliquots of serum sample diluted in DPBS/0.05% (v/v) Tween®/1% (W/V) BSA were added to coated and uncoated wells and incubated for 1 hour at 37° C. All serum samples have been tested either untreated or treated with 1.5M Glycine (v/v, pH 1.85) for 30 mn at 25° C. in a water bath, and further kept on ice and diluted with 1.5M Tris, v/v, pH 9.0. Samples were then immediately diluted (from 1/10 to 1/1000) and distributed on coated plates. Anti-rabbit IgG alkaline phosphatase-conjugated antibodies (ratio 1/10000), or goat anti-human IgG (ratio 1/2000), or IgM (ratio 1/2000) alkaline phosphatase-conjugated antibodies diluted in DPBS/0.05% (v/v) Tween®/ 1% (WN) BSA were added for 1 hour at 37° C. Detection of antigen-specific antibodies was performed after 30 mn of incubation at 37° C. with 100 µl pNPP substrate and the reaction was stopped by addition of 100 µl NaOH 3M. Concentration of HMGB1- or BOXB-specific antibodies has been calculated according to the standard curve obtained from standard immunoglobulin solution absorbance by Ascent software, ThermoElectrocorp, as we previously reported in an Elisa specific for *Shigella* LPS (Launay et al. *Vaccine* 2009, 27:1184-1191). The data are expressed in µg/ml of antibodies detected.

Figure 13A:
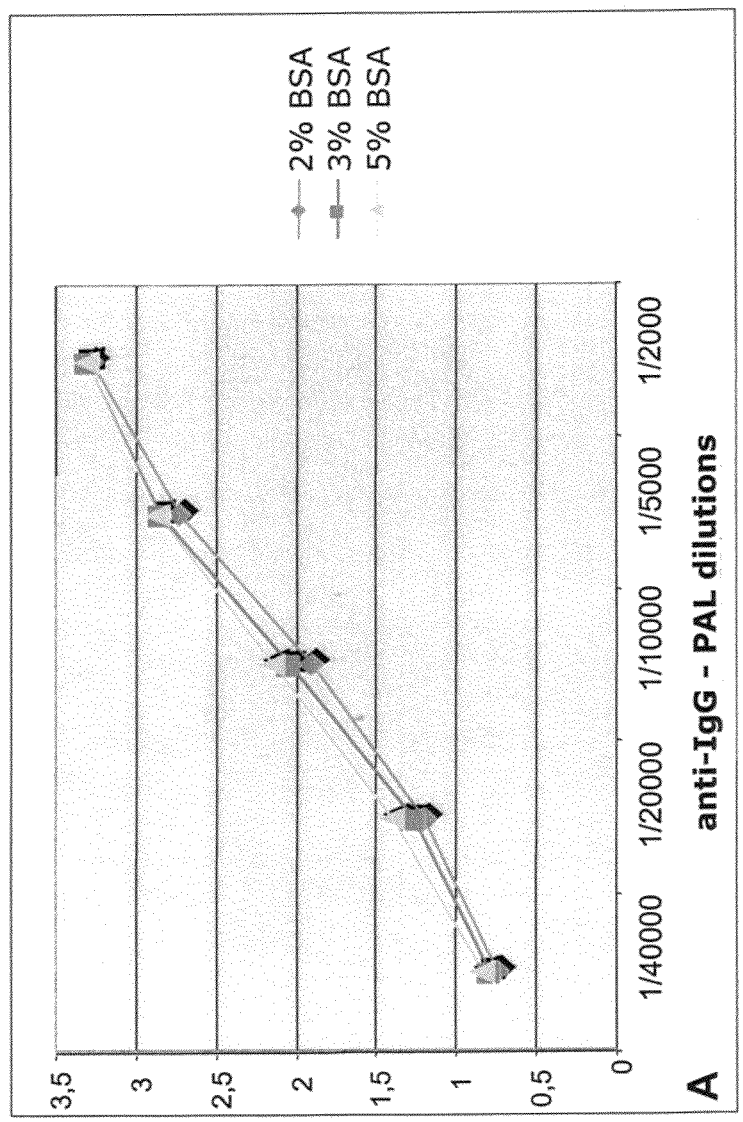
FIG. 13 (A)-(E). Determination of conditions for the ELISA assay for anti-HMGB1 antibodies (A): Determination of BSA concentration to saturate wells coated with HMGB1. (B): Determination of anti-IgG-PAL antibody concentration (secondary antibody) to reveal bound anti-HMGB1 antibodies. (C): Determination of HMGB1 concentration for coating the wells. (D): Determination of purified anti-HMGB1 antibody concentration for elaboration of the standard curve. (E): Specificity of the assay.
Figure 13B:
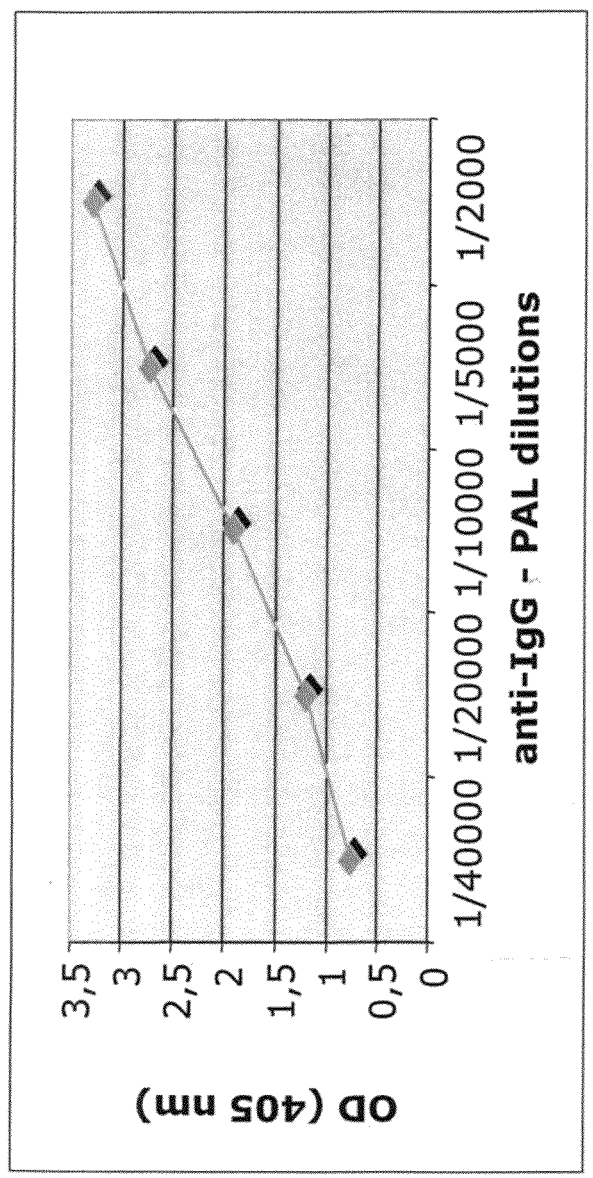
Figure 13C:
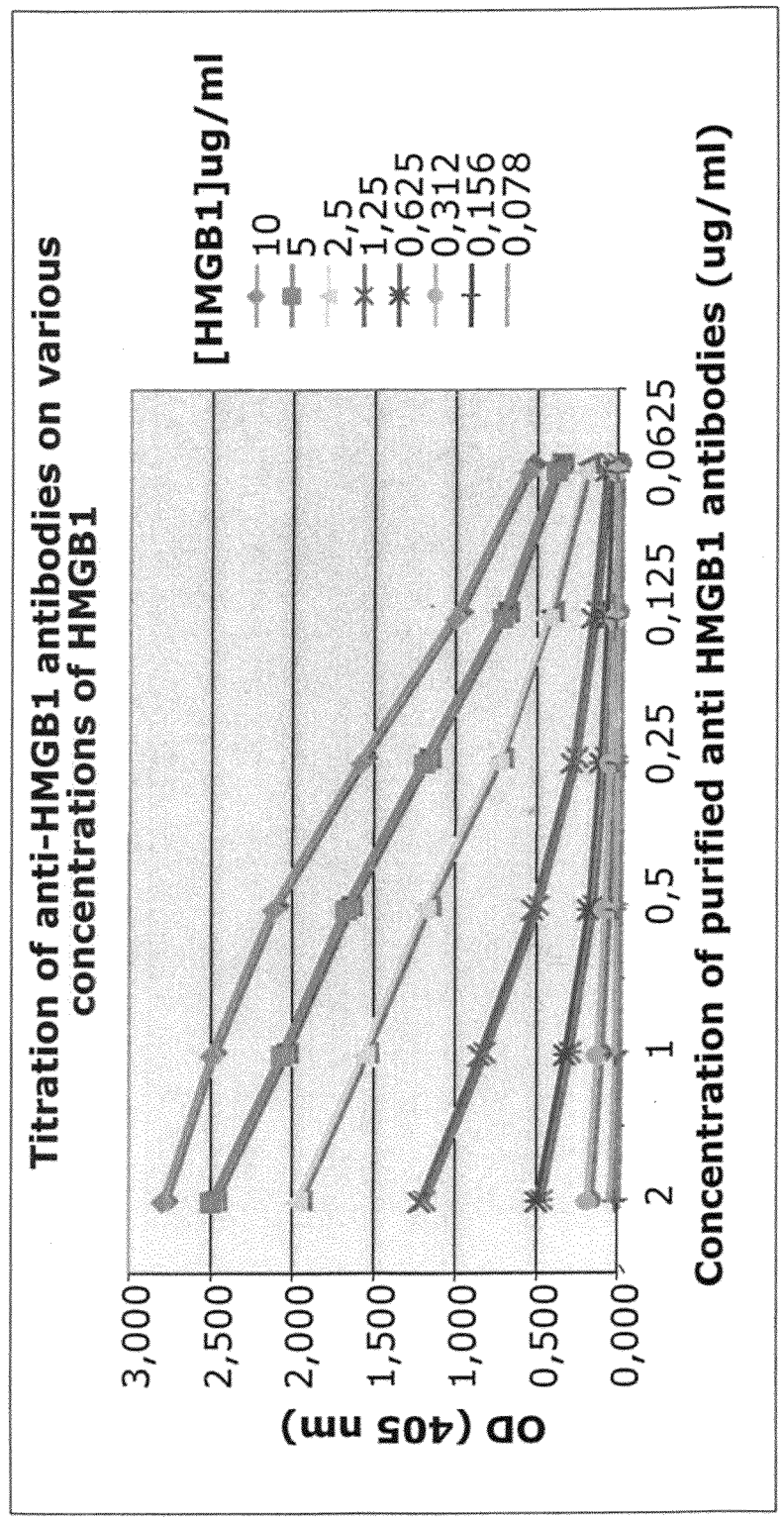
Figure 13D:
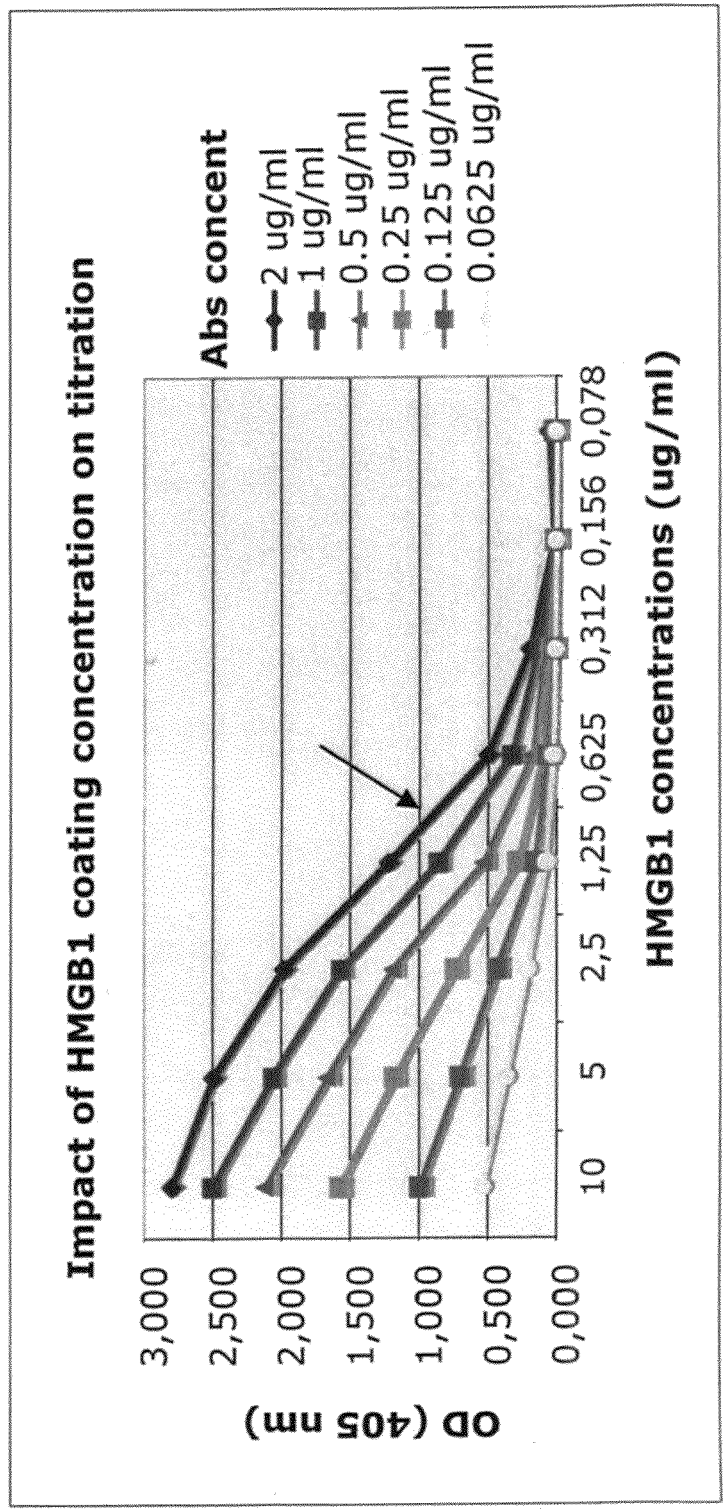
Figure 13:
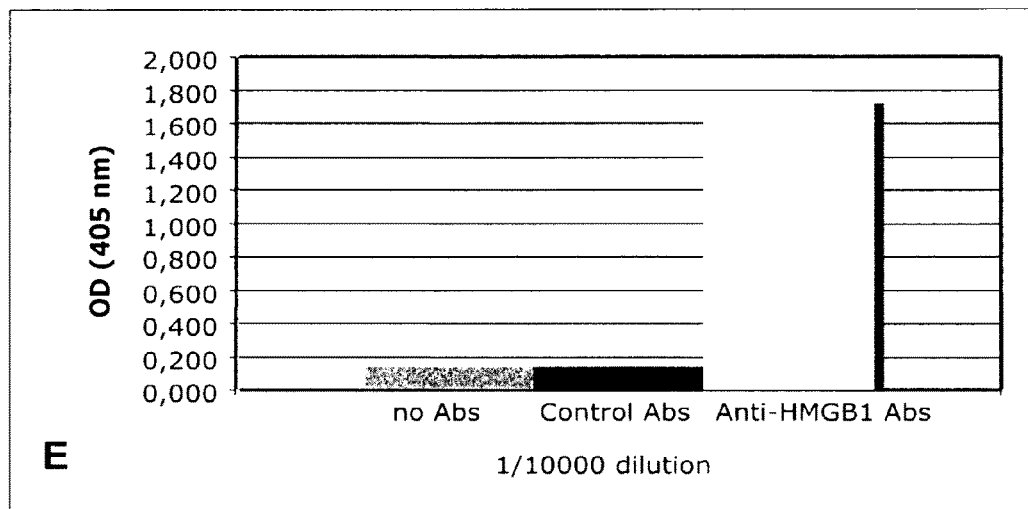
Figure 14:
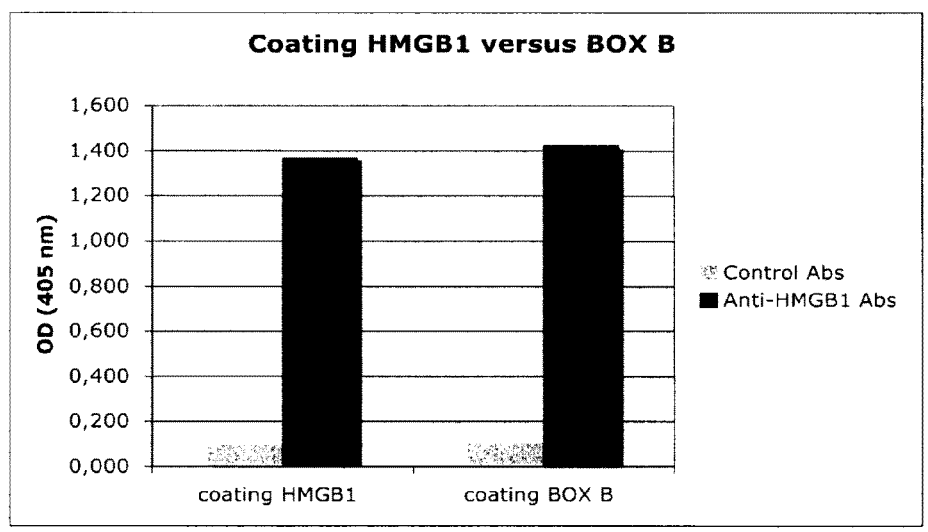
FIG. 14. anti-HBG1 titration with coating of the HMGB1 protein or of the BOXB.

To develop this assay, a number of parameters have been tested, using either HMGB1 or BOXB coated plates to titrate rabbit anti-human antibodies. The results obtained are the following:

a 2% to 5% BSA concentration is equally efficient (FIG. 13 A);

a 1/10 000 dilution of the anti-IgG-PAL antibody has been chosen as being in the linear part of the titration curve for purified anti-HMGB1 antibodies, shown by the arrows (FIG. 13B);

concentrations from 2.5 to 5 µg/ml of HMGB1 for coating the wells were the most appropriate as shown by the linearity of the titration curves for purified anti-HMGB1 antibodies (FIG. 13C);

a concentration of purified anti-HMGB1 antibody of 0.5 µg/ml was chosen (FIG. 13D);

the test was specific since there is no reactivity of non immune rabbit antibodies as compared with rabbit anti-HMGB1 antibodies (FIG. 13E); and comparable data were obtained when purified rabbit anti-human antibodies were tested on either HMGB1 or Box B-coated plates. Box B (the main immunogenic part of HMGB1) was further chosen (FIG. 14).

Acidic Treatment for the Detection of Complexed Anti-HMGB1 Antibodies in Human Samples To determine the assay conditions required for testing human biological samples, a series of human sera have been titrated for the presence of HMGB1-specific antibodies, and assuming that [HMGB1 anti-HMGB1 Ab] complexes were present in biological samples, the influence of pretreatment with Glycine 1.5M, pH1.85 to dissociate these immune complexes has been analyzed. All serum samples have been tested either being untreated or treated with 1.5M Glycine (v/v, pH 1.85) for 30 mn at 25° C. in a water bath, and further kept on ice and diluted with 1.5M Tris, v/v, pH 9.0. Samples were then immediately diluted and distributed on coated plates and tested as described above.

Figure 15:
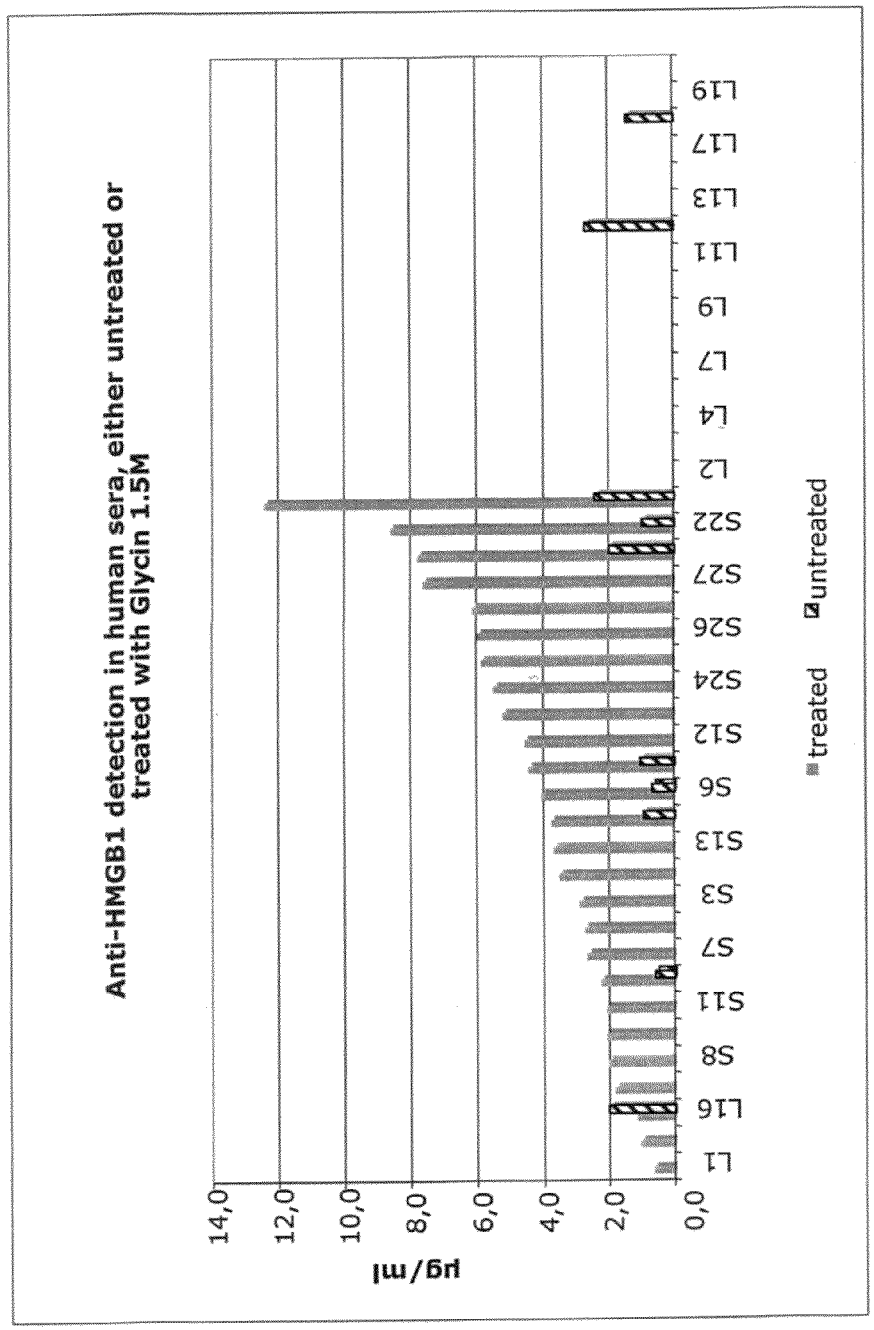
FIG. 15. Human sera, either untreated or treated with Glycin 1.5M, were titrated for the presence of anti-HMGB1 IgG antibodies. Circulating (Free) anti-HMGB1 antibodies were hachured represented, while complexed anti-HMGB1 antibodies were represented in grey.

The data presented in FIG. 15 show that anti-HMGB1 antibodies were hardly detected in human sera, unless they were treated with Glycin 1.5M to dissociate the immune complexes. Thus, most of the HMGB1-specific antibodies formed complexes with HMGB1, representing a neutralization mechanism for proinflammatory molecules.

Quantification of HMGB1 and Anti-HMGB1 Antibodies in Sera from HIV+ Patients

Circulating HMGB1 and anti-HMGB1 antibodies have been tested in untreated HIV-infected (HIV+) patients at different stages of the disease.

1. HMGB1 Titration in Sera from HIV-Infected Patients

Figure 16:
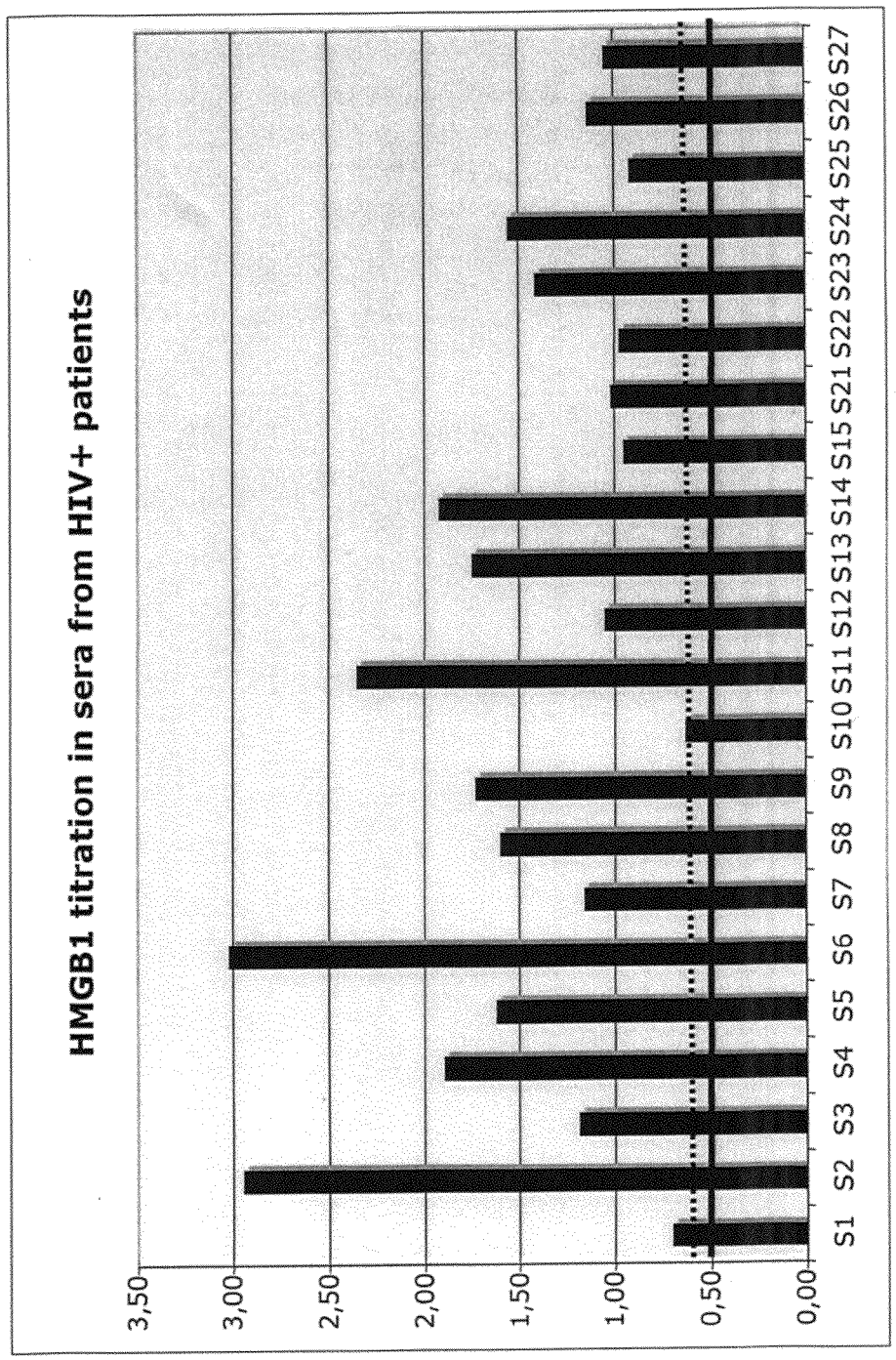
FIG. 16. titration of HMGB1 concentration in sera from HIV+ patients. Each histogram represents a single patient. The plain line indicates the minimal level of detection by the Elisa test, the dashed lines indicates the mean level of HMGB1 in healthy donors.

FIG. 16 shows that increased circulating levels of HMGB1 are detected in HIV+ patients as compared to healthy donors (dashed line).

2. Impact of Potent Antiretroviral Therapy on CD4 Cells, CD8 Cells, Proviral DNA and HIV RNA VL In the course of a one-year clinical follow-up of seven HIV+ patients (with detectable viral load; VL), the immunological effect of a highly active antiretroviral therapy (HAART) composed of a combination of anti-HIV drugs (blocking HIV entry and replication into the host cell), CD4 cells, CD8 cells, proviral DNA and HIV RNA VL were measured at initiation of HAART (M0), and after 1 (M1), 3 (M3), 6 (M6) and 12 (M12) months of HAART. Results are presented in the following Table and in FIG. 17.

|  | PATIENTS | | | | | | |
| --- | --- | --- | --- | --- | --- | --- | --- |
|  | P1 | P2 | P3 | P4 | P5 | P6 | P7 |
| M0 | | | | | | | |
| HIV-RNA ($\log_{10}$ cp/ml) | 6.72 | 4.15 | 3.54 | 5.65 | 4.90 | 6.15 | 3.85 |
| M1 | | | | | | | |
| Δ HIV-RNA ($\log_{10}$ cp/ml) | 3.72 | 2.37 | 1.50 | 3.51 | 2.09 | 2.35 | 1.46 |
| M3 | | | | | | | |
| Δ HIV-RNA ($\log_{10}$ cp/ml) | 3.25 | 2.85 | 1.94 | 3.40 | 2.32 | 2.10 | 2.24 |
| M6 | | | | | | | |
| Δ HIV-RNA ($\log_{10}$ cp/ml) | 4.82 | 2.85 | 1.40 | 3.96 | 2.30 | 0.81 | 2.24 |
| M12 | | | | | | | |
| Δ HIV-RNA ($\log_{10}$ cp/ml) | 4.84 | 2.85 | 2.24 | 2.88 | 3.30 | 2.21 | 2.55 |

This table of patients' characteristics show that HAART induces a significant and rapid suppression of HIV-RNA VL in all the patients (Δ viral load means the difference between VL at a given time point and VL at baseline M0), reaching undetectable levels (50 copies/ml blood). Moreover, HAART induces a significant increase in the number of blood CD4 T cells, while no change was detected at the CD8 T cell level (FIG. 17A). HAART also induces a significant decrease in plasmatic HIV-RNA viral load ($p<0.001$ at M1, M3 and $p<0.05$ at M6 and M12 vs M0. No significant effect on cell associated HIV-DNA was observed (FIG. 17B).

3. Impact of Potent Antiretroviral Therapy on HMGB1 and Anti-HMGB1 Antibodies in these Serum Samples.

Plasma levels of HMGB1 and anti-HMGB1 antibodies were titrated at initiation of HAART (M0), and after 1 (M1), 3 (M3), 6 (M6) and 12 (M12) months of HAART. Antibody titers have been determined by the assay described above, i.e. that patients' sera have been treated with Glycine before titration, and quantitated for anti-HMGB1 antibodies. Results are presented in FIGS. 18 and 19.

Figure 18:
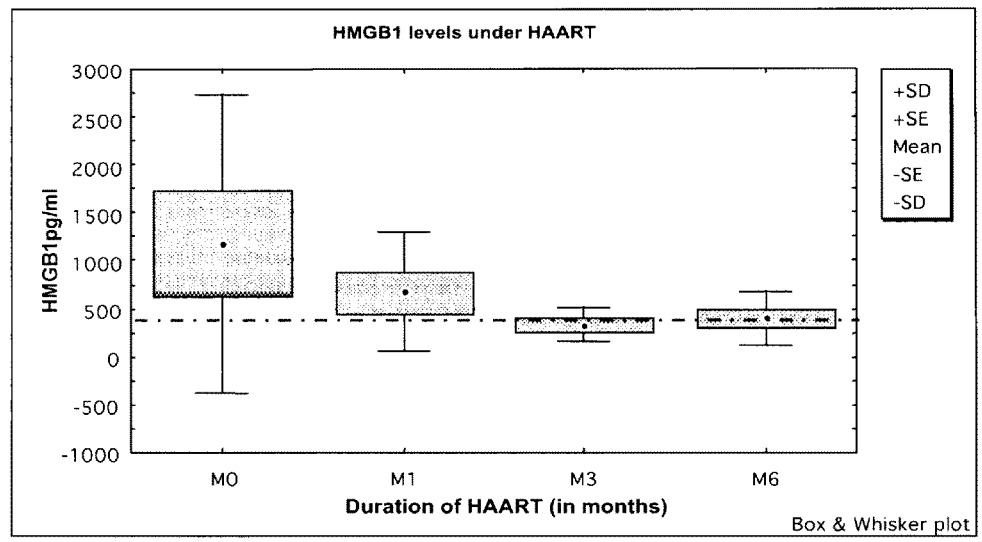
FIG. 18. Titration of HMGB1 in sera from HIV-infected patients receiving HAART at M0. The mean concentration of HMGB1 in healthy donors is shown by the dashed line.

Titration of HMGB1 in serum samples from these patients showed that suppression of HIV-RNA VL under HAART was associated with decreased levels of HMGB1 (FIG. 18). By M6, HMGB1 levels reached those of healthy individuals (dashed line). Thus, the impact of HAART argues for a driving role of HIV upon HMGB1 production.

Figure 19:
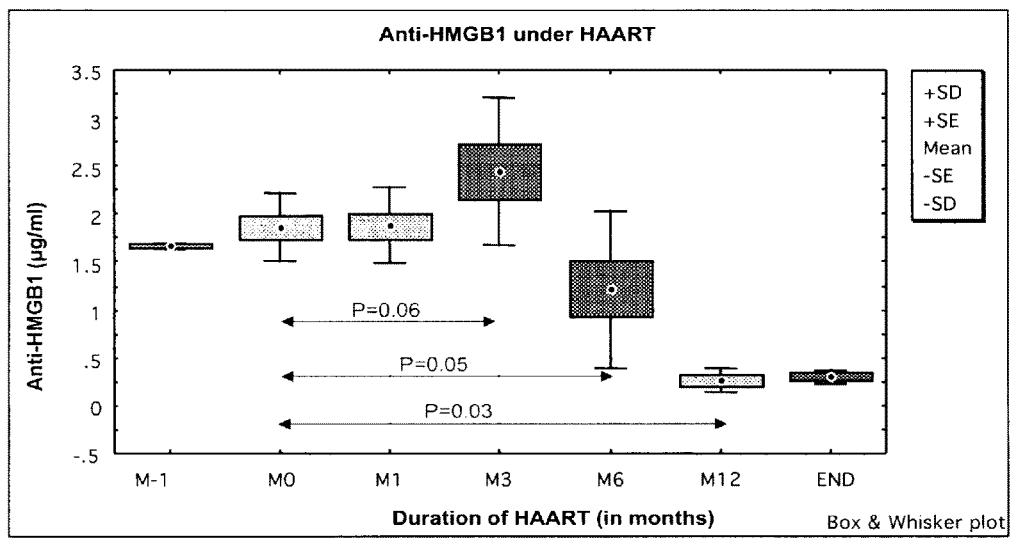
FIG. 19. Titration of anti-HMGB1 antibodies in sera from HIV-infected patients, and impact of antiretroviral therapy. M-1 means serum samples from patients tested 15 to 30 days before enrolment in the clinical trial. M1, M3, M6 and M12 indicate in the different time points following HAART. "Fin" means patients who stopped HAART between M9 and M12.

Data in FIG. 19 show that detectable concentrations of anti-HMGB1 antibodies were found in patients' sera at M0, and antiretroviral therapy induced a drop in anti-HMGB1 concentration by M6, reaching undetectable values at M12. Statistically significant decrease in anti-HMGB1 antibody levels as compared to baseline was detected at M6 ($p=0.05$) and at later time points (M12) as well.

Therefore, the combined measures of HMGB1 and anti-HMGB1 levels indicate that chronic HIV infection triggers the production of HMGB1, which in turn triggers the production of neutralizing antibodies. This is a dynamic process implying a delay between a drop of HMGB1 levels (M3) and a decrease of anti-HMGB1 levels (M6), the levels of both molecules being normalized following potent antiretroviral therapy.

Correlations Between Anti-HMGB1 Levels and HIV Viral Load

Considering the above-mentioned results, an important question was addressed regarding whether circulating levels of HMGB1 and anti-HMGB1 antibodies were correlated with HIV-RNA viral load.

Therefore, serum samples from HIV+ patients were tested, at different stages of the disease, with variable viral load. The results are summarized in the following table (Spearman's correlation test), and in FIG. 20.

|  | HMGB1 | HIV-RNA VL |
| --- | --- | --- |
| Anti-HMGB1 Abs | $r = -0.5$ | $r = -0.49$ |
|  | $P = 0.018$ | $p < 0.0001$ |
|  | $n = 22$ | $n = 61$ | r = coefficient of correlation;
p < 0.05: >95% probability that the two variables are correlated;
n = number of patients in the study As shown on FIG. 20A, there is an inverse correlation between HMGB1 and anti-HMGB1 antibody levels, indicating that HMGB1 production induces the synthesis of anti-HMGB1 antibodies that neutralize HMGB1, as low levels of HMGB1 are associated with high levels of antibodies.

FIG. 20B demonstrates that there is an inverse correlation between anti-HMGB1 antibodies and VL, suggesting that, due to the neutralizing activity of anti-HMGB1 antibodies, the stimulating activity of HMGB1 on viral replication is suppressed by the antibodies.

These data argue for a beneficial effect of anti-HMGB1-based therapy in HIV+ patients, which would lead to HMGB1 neutralization and therefore a decrease in the viral load.

MODIFICATIONS AND OTHER EMBODIMENTS

Various modifications and variations of the disclosed products, compositions, and methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical, immunological, biological, chemical or pharmacological arts or related fields are intended to be within the scope of the following claims.

INCORPORATION BY REFERENCE

Each document, patent, patent application or patent publication cited by or referred to in this disclosure is incorporated by reference in its entirety, especially with respect to the specific subject matter surrounding the citation of the reference in the text. However, no admission is made that any such reference constitutes background art and the right to challenge the accuracy and pertinence of the cited documents is reserved.

REFERENCES

1. Meng, G. et al. Primary intestinal epithelial cells selectively transfer R5 HIV-1 to CCR5+ cells. Nat Med 8, 150-6 (2002).
2. Pope, M. & Haase, A. T. Transmission, acute HIV-1 infection and the quest for strategies to prevent infection. Nat Med 9, 847-52 (2003).
3. Geijtenbeek, T. B. et al. DC-SIGN, a dendritic cell-specific HIV-1-binding protein that enhances trans-infection of T cells. Cell 100, 587-97 (2000).
4. Lee, B. et al. cis Expression of DC-SIGN allows for more efficient entry of human and simian immunodeficiency viruses via CD4 and a coreceptor. J Virol 75, 12028-38 (2001).
5. Gurney, K. B. et al. Binding and transfer of human immunodeficiency virus by DCSIGN+ cells in human rectal mucosa. J Virol 79, 5762-73 (2005).
6. Turville, S. G. et al. Diversity of receptors binding HIV on dendritic cell subsets. Nat Immunol 3, 975-83 (2002).
7. McDonald, D. et al. Recruitment of HIV and its receptors to dendritic cell-T cell junctions. Science 300, 1295-7 (2003).
8. Arrighi, J. F. et al. DC-SIGN-mediated infectious synapse formation enhances X4 HIV-1 transmission from dendritic cells to T cells. J Exp Med 200, 1279-88 (2004).
9. Piguet, V. & Sattentau, Q. Dangerous liaisons at the virological synapse. J Clin Invest 114, 605-10 (2004).
10. Wu, L. & KewalRamani, V. N. Dendritic-cell interactions with HIV: infection and viral dissemination. Nat Rev Immunol 6, 859-68 (2006).
11. Pulendran, B., Palucka, K. & Banchereau, J. Sensing pathogens and tuning immune responses. Science 293, 253-6 (2001).
12. Carbone, E. et al. Recognition of autologous dendritic cells by human NK cells. Eur J Immunol 29, 4022-9 (1999).
13. Fernandez, N. C. et al. Dendritic cells directly trigger NK cell functions: cross-talk relevant in innate anti-tumor immune responses in vivo. Nat Med 5, 405-11 (1999).
14. Piccioli, D., Sbrana, S., Melandri, E. & Valiante, N. M. Contact-dependent stimulation and inhibition of dendritic cells by natural killer cells. J Exp Med 195, 335-41 (2002).
15. Degli-Esposti, M. A. & Smyth, M. J. Close encounters of different kinds: dendritic cells and NK cells take centre stage. Nat Rev Immunol 5, 112-24 (2005).
16. Ferlazzo, G. et al. Distinct roles of IL-12 and IL-15 in human natural killer cell activation by dendritic cells from secondary lymphoid organs. Proc Natl Acad Sci USA 101, 16606-11 (2004).
17. Ferlazzo, G. et al. Human dendritic cells activate resting natural killer (NK) cells and are recognized via the NKp30 receptor by activated NK cells. J Exp Med 195, 343-51 (2002).
18. Borg, C. et al. NK cell activation by dendritic cells (DCs) requires the formation of a synapse leading to IL-12 polarization in DCs. Blood 104, 3267-75 (2004).
19. Marcenaro, E. et al. IL-12 or IL-4 prime human NK cells to mediate functionally divergent interactions with dendritic cells or tumors. J Immunol 174, 3992-8 (2005).
20. Semino, C., Angelini, G., Poggi, A. & Rubartelli, A. NK/iDC interaction results in IL18 secretion by DCs at the synaptic cleft followed by NK cell activation and release of the DC maturation factor HMGB1. Blood 106, 609-16 (2005).
21. Vitale, M. et al. NK-dependent DC maturation is mediated by TNFalpha and IFNgamma released upon engagement of the NKp30 triggering receptor. Blood 106, 566-71 (2005).
22. Della Chiesa, M. et al. The natural killer cell-mediated killing of autologous dendritic cells is confined to a cell subset expressing CD94/NKG2A, but lacking inhibitory killer Ig-like receptors. Eur J Immunol 33, 1657-66 (2003).
23. Park, J. S. et al. Activation of gene expression in human neutrophils by high mobility group box 1 protein. Am J Physiol Cell Physiol 284, C870-9 (2003).
24. Stros, M., Ozaki, T., Bacikova, A., Kageyama, H. & Nakagawara, A. HMGB1 and HMGB2 cell-specifically down-regulate the p53- and p73-dependent sequence-specific transactivation from the human Bax gene promoter. J Biol Chem 277, 715764 (2002).
25. Gardella, S. et al. The nuclear protein HMGB1 is secreted by monocytes via a non-classical, vesicle-mediated secretory pathway. EMBO Rep 3, 995-1001 (2002).
26. Zeh, H. J., 3rd & Lotze, M. T. Addicted to death: invasive cancer and the immune response to unscheduled cell death. J Immunother 28, 1-9 (2005).
27. Lotze, M. T. & Tracey, K. J. High-mobility group box 1 protein (HMGB1): nuclear weapon in the immune arsenal. Nat Rev Immunol 5, 331-42 (2005).
28. Bianchi, M. E. & Manfredi, A. A. High-mobility group box 1 (HMGB1) protein at the crossroads between innate and adaptive immunity. Immunol Rev 220, 35-46 (2007).
29. Andoniou, C. E. et al. Interaction between conventional dendritic cells and natural killer cells is integral to the activation of effective antiviral immunity. Nat Immunol 6, 1011-9 (2005).
30. Mavilio, D. et al. Characterization of the defective interaction between a subset of natural killer cells and dendritic cells in HIV-1 infection. J Exp Med 203, 2339-50 (2006).
31. Mollica, L. et al. Glycyrrhizin binds to high-mobility group box 1 protein and inhibits its cytokine activities. Chem Biol 14, 431-41 (2007).
32. Moser, B., Herold, K. C. & Schmidt, A. M. Receptor for advanced glycation end products and its ligands: initiators or amplifiers of joint inflammation—a bit of both? Arthritis Rheum 54, 14-8 (2006).
33. Bierhaus, A. et al. Understanding RAGE, the receptor for advanced glycation end products. J Mol Med 83, 876-86 (2005).

34. Yu, M. et al. HMGB1 signals through toll-like receptor (TLR) 4 and TLR2. Shock 26, 174-9 (2006).
35. Clynes, R. et al. Receptor for AGE (RAGE): weaving tangled webs within the inflammatory response. Curr Mol Med 7, 743-51 (2007).
36. Manfredi, A. A. et al. Maturing dendritic cells depend on RAGE for in vivo homing to lymph nodes. J Immunol 180, 2270-5 (2008).
37. Mailliard, R. B. et al. Dendritic cells mediate NK cell help for Th1 and CTL responses: two-signal requirement for the induction of NK cell helper function. J Immunol 171, 2366-73 (2003).
38. Nowak, P. et al. HMGB1 activates replication of latent HIV-1 in a monocytic cell-line, but inhibits HIV-1 replication in primary macrophages. Cytokine 34, 17-23 (2006).
39. Thierry, S. et al. High-mobility group box 1 protein induces HIV-1 expression from persistently infected cells. Aids 21, 283-92 (2007).
40. Granelli-Piperno, A., Delgado, E., Finkel, V., Paxton, W. & Steinman, R. M. Immature dendritic cells selectively replicate macrophagetropic (M-tropic) human immunodeficiency virus type 1, while mature cells efficiently transmit both M- and T-tropic virus to T cells. J Virol 72, 2733-7 (1998).
41. Canque, B. et al. The susceptibility to X4 and R5 human immunodeficiency virus-1 strains of dendritic cells derived in vitro from CD34(+) hematopoietic progenitor cells is primarily determined by their maturation stage. Blood 93, 3866-75 (1999).
42. Turville, S. G. et al. Immunodeficiency virus uptake, turnover, and 2-phase transfer in human dendritic cells. Blood 103, 2170-9 (2004).
43. Nobile, C. et al. Covert human immunodeficiency virus replication in dendritic cells and in DC-SIGN-expressing cells promotes long-term transmission to lymphocytes. J Virol 79, 5386-99 (2005).
44. Burleigh, L. et al. Infection of dendritic cells (DCs), not DC-SIGN-mediated internalization of human immunodeficiency virus, is required for long-term transfer of virus to T cells. J Virol 80, 2949-57 (2006).
45. Yang, D. et al. High mobility group box-1 protein induces the migration and activation of human dendritic cells and acts as an alarmin. J Leukoc Biol 81, 59-66 (2007).
46. Dumitriu, I. E., Bianchi, M. E., Bacci, M., Manfredi, A. A. & Rovere-Querini, P. The secretion of HMGB1 is required for the migration of maturing dendritic cells. J Leukoc Biol 81, 84-91 (2007).
47. Nowak, P., Barqasho, B. & Sonnerborg, A. Elevated plasma levels of high mobility group box protein 1 in patients with HIV-1 infection. Aids 21, 869-71 (2007).
48. Dumitriu, I. E. et al. Release of high mobility group box 1 by dendritic cells controls T cell activation via the receptor for advanced glycation end products. J Immunol 174, 7506-15 (2005).
49. Fehniger, T. A. et al. Differential cytokine and chemokine gene expression by human NK cells following activation with IL-18 or IL-15 in combination with IL-12: implications for the innate immune response. J Immunol 162, 4511-20 (1999).
50. Agaugue, S., Marcenaro, E., Ferranti, B., Moretta, L. & Moretta, A. Human natural killer cells exposed to IL-2, IL-12, IL-18 or IL-4 differently modulate priming of naive T cells by monocyte-derived dendritic cells. Blood (2008).
51. Donaghy, H., Gazzard, B., Gotch, F. & Patterson, S. Dysfunction and infection of freshly isolated blood myeloid and plasmacytoid dendritic cells in patients infected with HIV-1. Blood 101, 4505-11 (2003).
52. Smed-Sorensen, A., Lore, K., Walther-Jallow, L., Andersson, J. & Spetz, A. L. HIV-1 infected dendritic cells up-regulate cell surface markers but fail to produce IL-12 p70 in response to CD40 ligand stimulation. Blood 104, 2810-7 (2004).
53. Kiertscher, S. M. & Roth, M. D. Human CD14+ leukocytes acquire the phenotype and function of antigen-presenting dendritic cells when cultured in GM-CSF and IL-4. J Leukoc Biol 59, 208-18 (1996).
54. Saidi, H. et al. Pre-clinical development as microbicide of zinc tetra-ascorbo-camphorate, a novel terpenoid derivative: Potent in vitro inhibitory activity against both R5- and X4-tropic HIV-1 strains without significant in vivo mucosal toxicity. AIDS Res Ther 5, 10 (2008).
55. Lecoeur, H., Melki, M. T., Saidi, H. & Gougeon, M. L. Analysis of Apoptotic Pathways by Multiparametric Flow Cytometry: Application to HIV Infection. Methods Enzymol 442, 51-82 (2008).
56. Ledru, E. et al. A nonsecreted variant of interleukin-4 is associated with apoptosis: implication for the T helper-2 polarization in HIV infection. Blood 101, 3102-5 (2003).

The invention claimed is:

1. A method for the quantitation of high mobility group box 1 (HMGB1) protein in a patient infected with human immunodeficiency virus type 1 (HIV-1) comprising:
   obtaining a biological sample from the HIV-1 infected patient;
   treating the biological sample with acid to dissociate immune complexes in the biological sample;
   neutralizing the acid; and
   quantitating HMGB1 protein in the biological sample.

2. The method of claim 1, wherein the biological sample is blood, plasma, serum, saliva, or peripheral blood mononuclear cells.

3. The method of claim 1, wherein the biological sample is serum.

4. The method of claim 1, wherein the biological sample is plasma.

5. The method of claim 1, further comprising measuring the viral RNA load in the biological sample.

6. The method of claim 1, wherein the patient is undergoing an antiviral treatment.

7. The method of claim 1, further comprising quantitating High mobility group box 1 (HMGB1) protein in a biological sample from the patient at multiple timepoints.

8. The method of claim 1, wherein the quantitation of High mobility group box 1 (HMGB1) protein is performed by ELISA.

9. The method of claim 1, wherein the HMGB1 protein is quantitated during primary or acute infection of the patient.

10. The method of claim 1, wherein the HMGB1 protein is quantitated during chronic infection of the patient.

11. The method of claim 1, wherein the biological sample is treated with Glycine.

12. The method of claim 11, wherein the biological sample is treated with 1.5M Glycine.

13. A kit to quantitate human High mobility group box 1 protein (HMGB1) in a sample, comprising:
   a) an antibody or fragment thereof specific for High mobility group box 1 (HMGB1);
   b) an acidic dissociation solution that dissociates immunological HMGB1/anti-HMGB1 antibody complexes in the sample; and
   c) a neutralization buffer.

14. The kit of claim 13, wherein the acidic dissociation solution comprises glycine.

15. The kit of claim 13, wherein the glycine is at a concentration of 1.5M.

16. The kit of claim 13, wherein the acidic dissociation solution has a pH between pH1 and pH3.

17. The kit of claim 13, wherein the neutralization buffer comprises Tris.

18. The kit of claim 13, wherein the Tris is at a concentration of 1.5M and a pH of 9.0.

19. The kit of claim 13, further comprising secondary antibodies that bind to the HMGB1/antibody complex.

* * * * *